United States Patent [19]
McMurry et al.

[11] Patent Number: 6,043,228
[45] Date of Patent: Mar. 28, 2000

[54] O⁶-SUBSTITUTED GUANINE DERIVATIVES, A PROCESS FOR THEIR PREPARATION AND THEIR USE IN TREATING TUMOR CELLS

[75] Inventors: Thomas Brian McMurry; Robert Stanley McBlhinney; Joan Elizabeth McCormick, all of Dublin, Ireland; Rhoderick Hugh Elder, Manchester, United Kingdom; Jane Kelly, Manchester, United Kingdom; Geoffrey Margison, Manchester, United Kingdom; Joseph Anthony Rafferty, Manchester, United Kingdom; Amanda Jean Watson, Manchester, United Kingdom; Mark Andrew Willington, Manchester, United Kingdom; Dorothy Josephine Donnelly, Dublin, Ireland

[73] Assignee: Cancer Research Campaign Technology Limited, Regent's Park, United Kingdom

[21] Appl. No.: 08/568,576

[22] Filed: Dec. 7, 1995

Related U.S. Application Data

[63] Continuation-in-part of application No. PCT/IE94/00031, Jun. 8, 1994.

[30] Foreign Application Priority Data

Jun. 8, 1993 [IE] Ireland ...................................... 930432
May 23, 1994 [GB] United Kingdom ................... 9410421

[51] Int. Cl.⁷ .......................... A61K 31/70; A01N 43/54; A01N 43/90
[52] U.S. Cl. ........................... 514/45; 514/261; 514/264; 514/276; 514/277; 536/27.81; 544/264; 544/265; 544/268; 544/269; 544/270
[58] Field of Search .............................. 514/45, 262, 276, 514/261, 264, 277; 536/27.81; 544/264, 265, 268, 269, 270

[56] References Cited

U.S. PATENT DOCUMENTS

| | | | |
|---|---|---|---|
| 4,772,606 | 9/1988 | Sircar et al. ............................. | 514/562 |
| 5,091,430 | 2/1992 | Moschel et al. ........................ | 514/565 |
| 5,260,291 | 11/1993 | Lunt et al. . | |
| 5,353,669 | 10/1994 | Moschel et al. ........................... | 514/45 |
| 5,525,606 | 6/1996 | Moschel et al. . | |

FOREIGN PATENT DOCUMENTS

| | | |
|---|---|---|
| 184 473 A1 | 6/1986 | European Pat. Off. . |
| 2139107 | 2/1973 | Germany . |
| 91/13898 | 9/1991 | WIPO . |
| 94/29312 | 12/1994 | WIPO . |

OTHER PUBLICATIONS

J.F. Bunnett et al., "The Relative Reactivities of Methanol and Methoxide Ion in Addition to 4–Chloroenzyme," *Organic Chemistry*, vol. 34, No. 7, p. 2035, Jul. 1969.
*Chemical Abstracts*, vol. 101, No. 25, pp. 765–766, Dec. 17, 1985.
Dolan, M.E., et al., Cancer Research (1986), vol. 46, pp. 4500–4504.
Dolan, M.E., et al., Cancer Chemother. Pharmacol. (1989), vol. 25, pp. 103–108.
Pegg, A.E., Biochemistry (1993), vol. 32, pp. 11998–12006.
Arris, C.E., Anti–Cancer Drug Design (1994), vol. 9, pp. 401–408.
Marathi, U.K., et al., Biochemical Pharmacology (1994), vol. 48, pp. 2127–2134.
Wibley, J.E.A., et al., Anti–Cancer Drug Design (1995), vol. 10, pp. 75–95.
Pegg, A.E., Biochemical Pharmacology (1995), vol. 50, pp. 1141–1148.
Berg, S.L., et al., Cancer Research (1995), vol. 55, pp. 4606–4610.
Cancer Research (1994), vol. 54, pp. 5123–5130.
J. Med. Chem. (1995), vol. 38, pp. 359–365.
Cancer Research (1995), vol. 55, pp. 2853–2857.
Proc. Nat'l Acad. Sci. USA (1990), vol. 87, pp. 5368–5372.
Cancer Communications (1990), vol. 2, pp. 371–377.
J. Med. Chem. (1994), vol. 37, pp. 342–347.
J. Med. Chem. (1977), vol. 20, pp. 341–344.
J. Med. Chem. (1975), vol. 18, pp. 968–973.
J. Med. Chem. (1992), vol. 35, pp. 4486–4491.
Tetrahedron Letters (1985), vol. 26, pp. 1815–1818.

*Primary Examiner*—James O. Wilson
*Attorney, Agent, or Firm*—Smith, Gambrell & Russell

[57] ABSTRACT

O⁶-hetarylalkyl- or naphthylalkylguanine derivatives of the formula

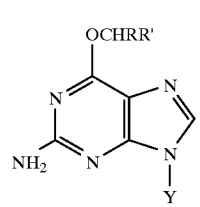

(I)

wherein
  Y is H, ribosyl, deoxyribosyl, or R"XCHR',
    wherein X is O or S, R" and R'" are alkyl, or substituted derivatives thereof,
  R' is H, or alkyl or hydroxyalkyl
  R is
    (i) a cyclic group having at least one 5- or 6-membered heterocyclic ring, optionally with a carbocyclic or heterocyclic ring fused thereto, the or each heterocyclic ring having at least one hereto atom chosen from O, N, or S, or a substituted derivative thereof; or
    (ii) naphthyl or a substituted derivative thereof
and pharmaceutically acceptable salts thereof, exhibit the ability to deplete O⁶-alkylguanine-DNA alkyltransferase (ATase) activity.

A process for preparation of the compounds is described. The compounds have utility in combination with alkylating agents in the chemotherapeutic treatment of tumour cells.

35 Claims, 37 Drawing Sheets

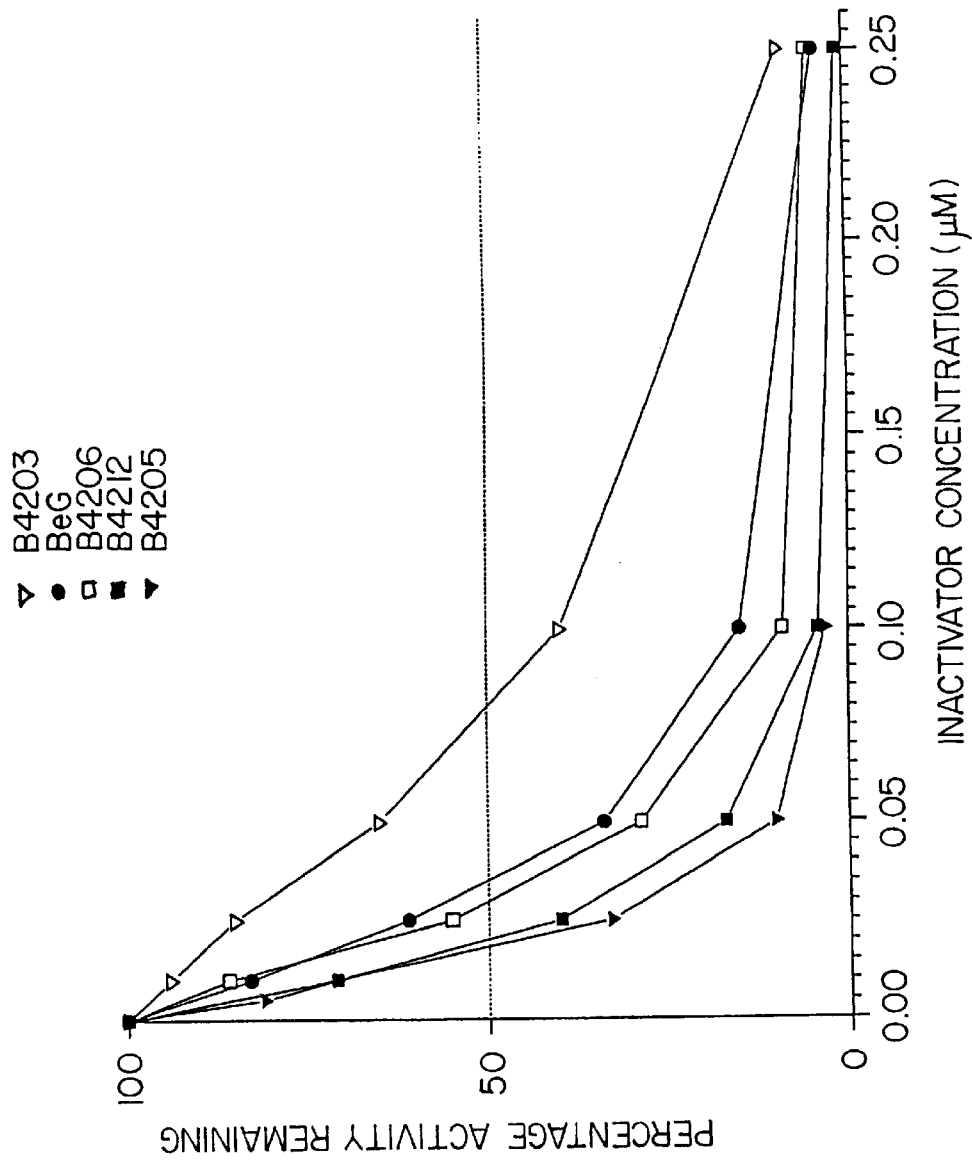

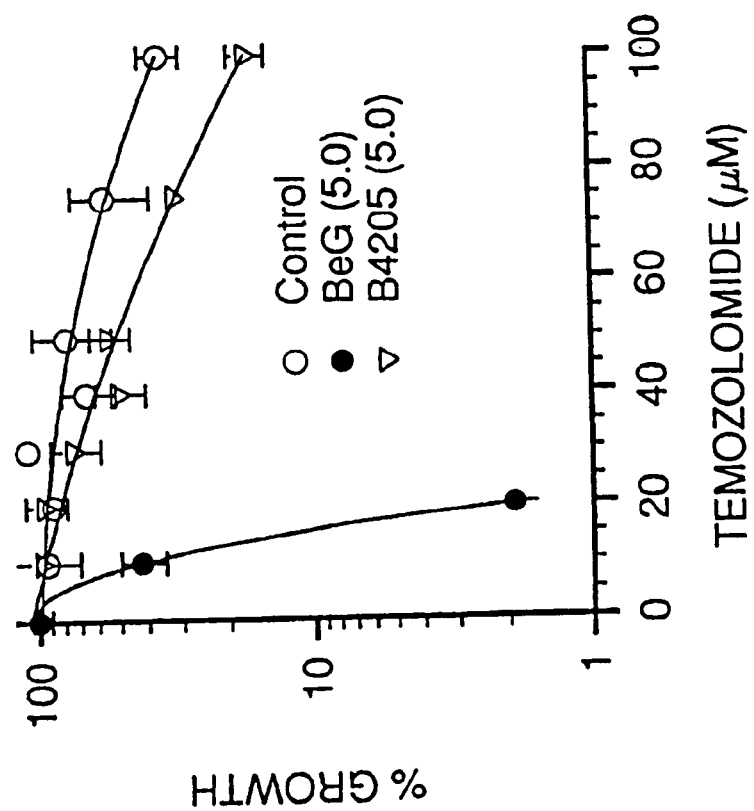
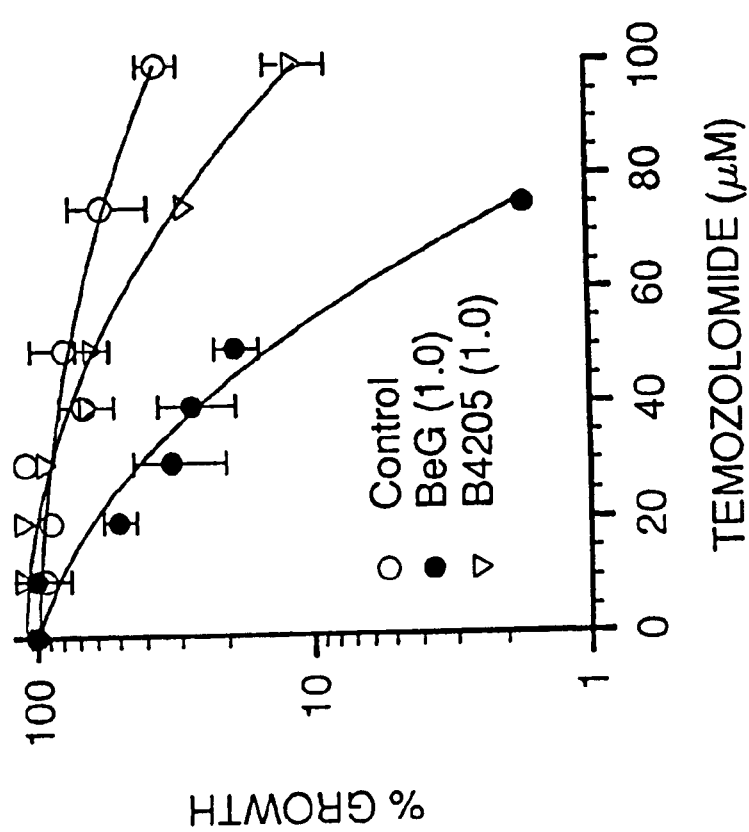

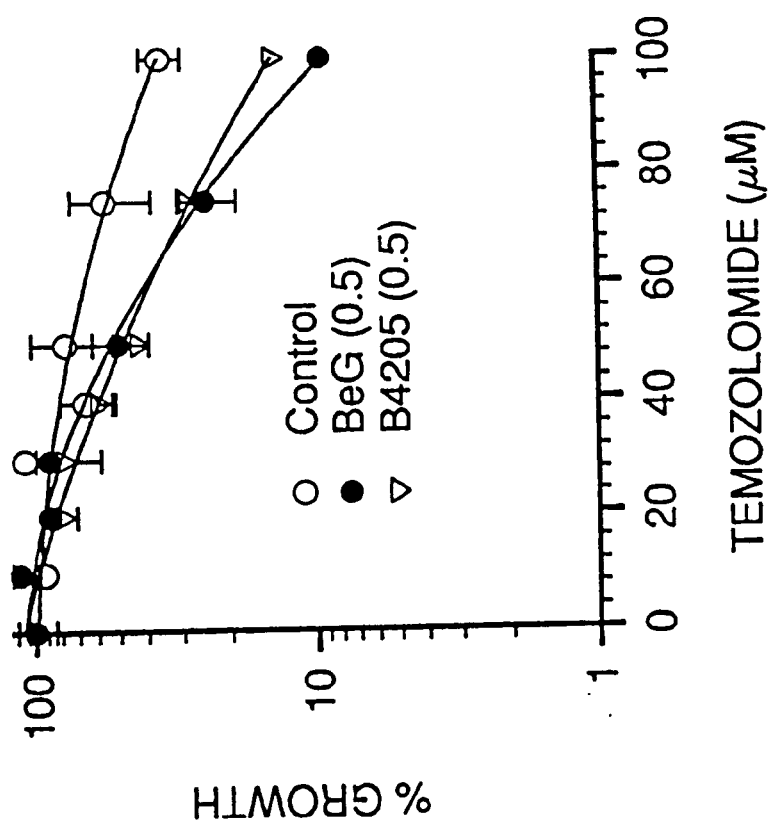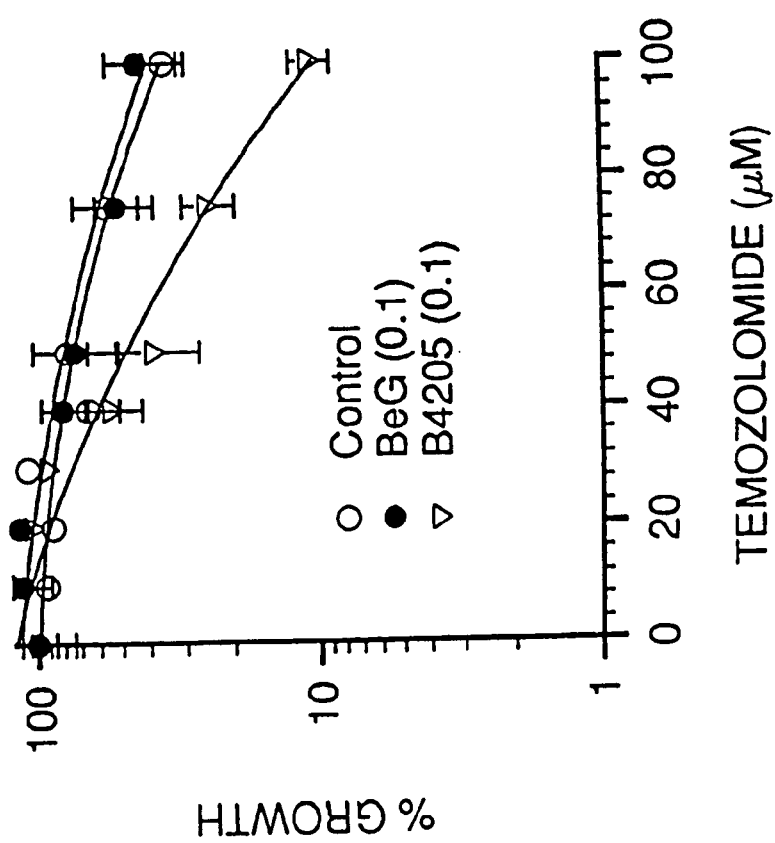

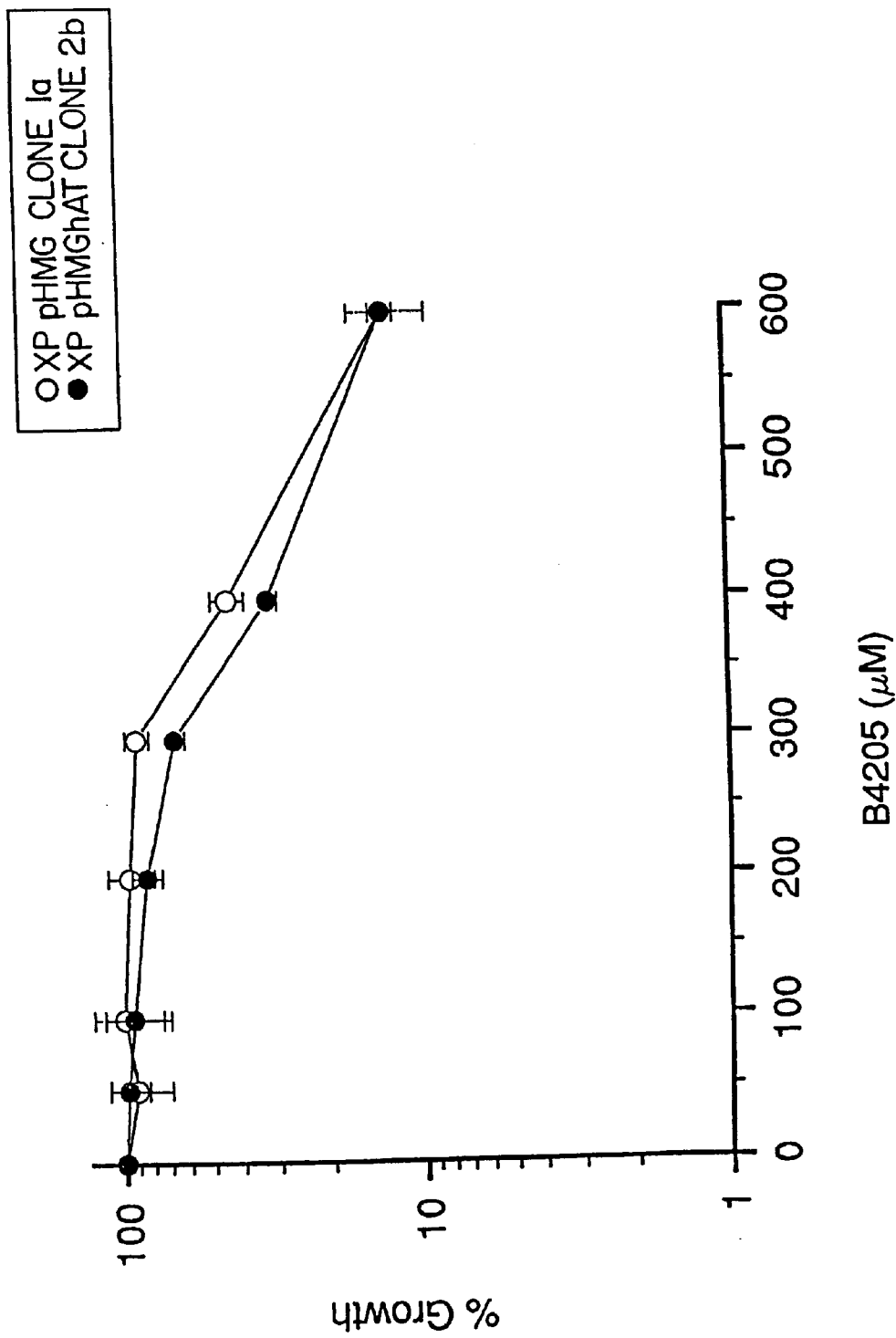

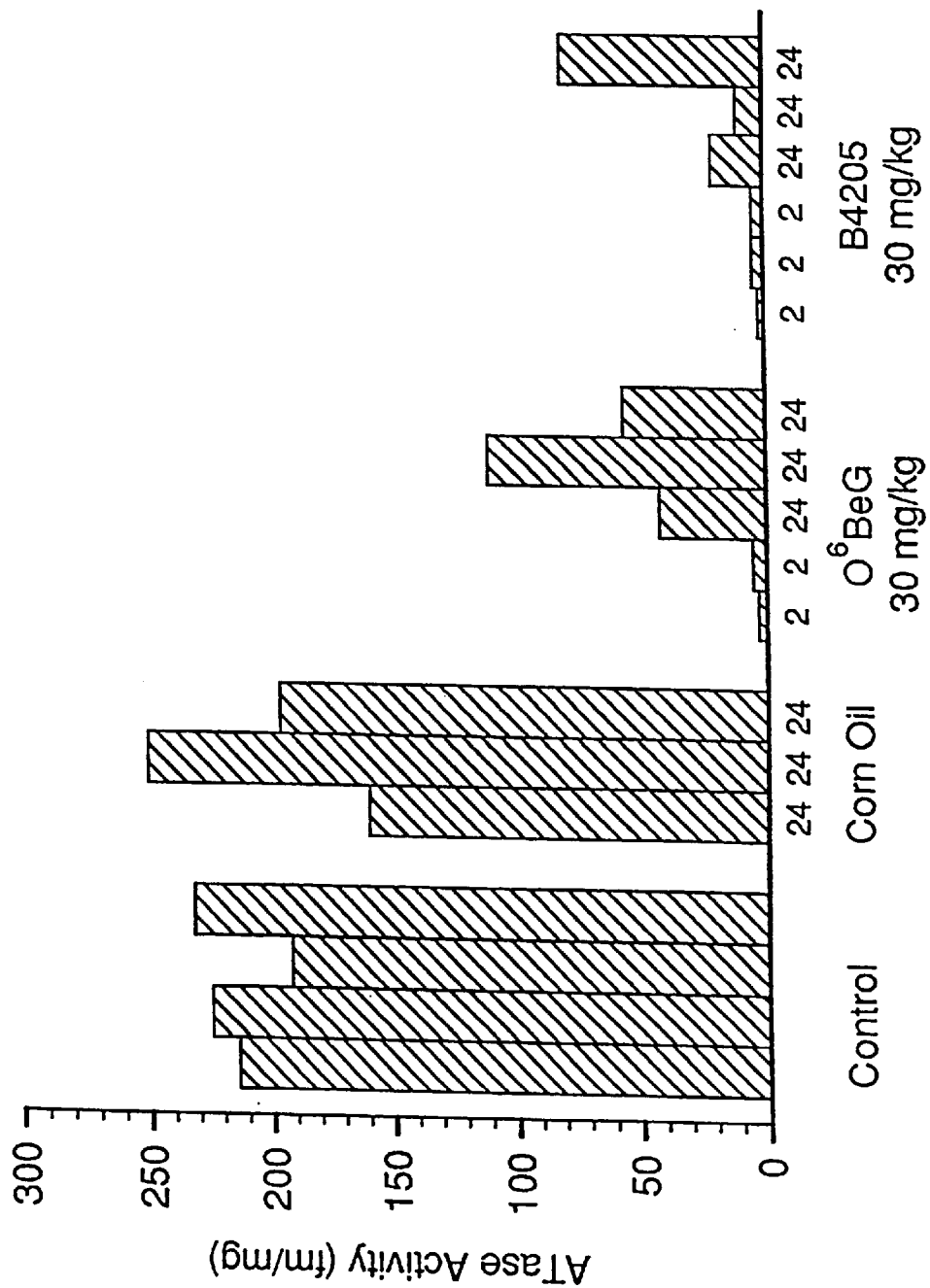

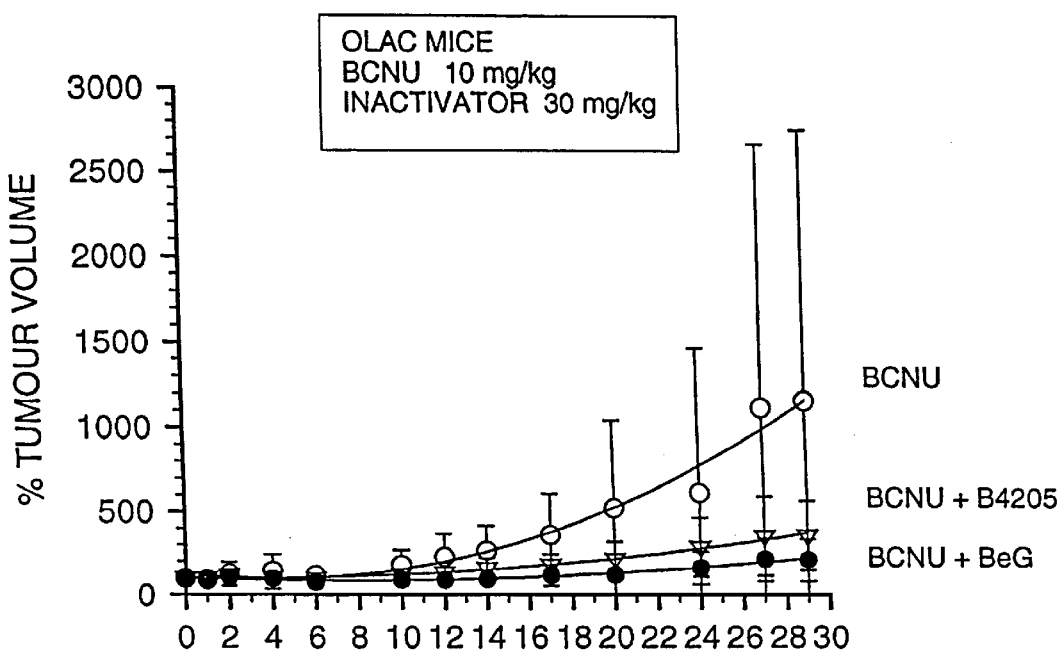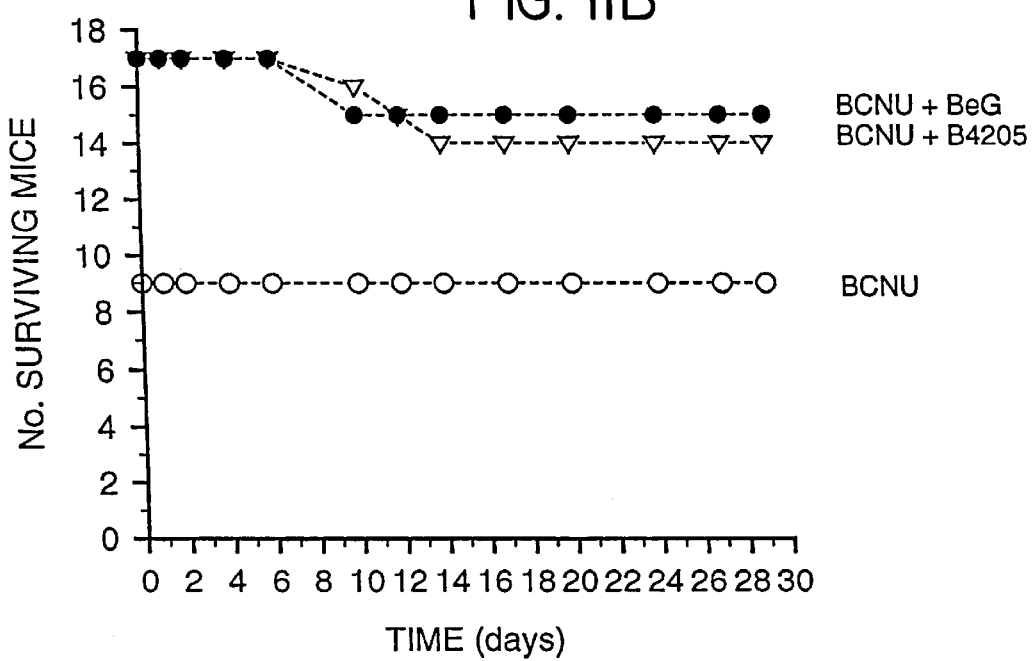

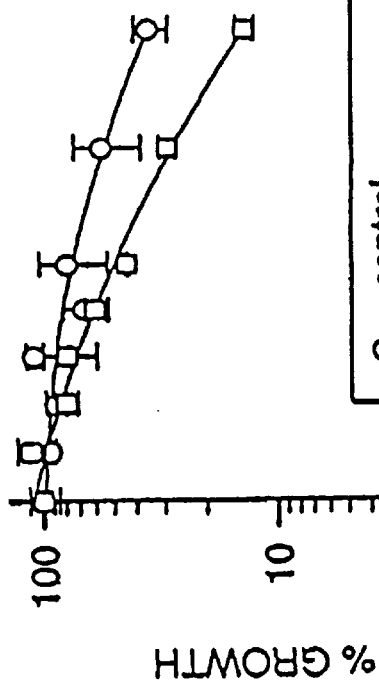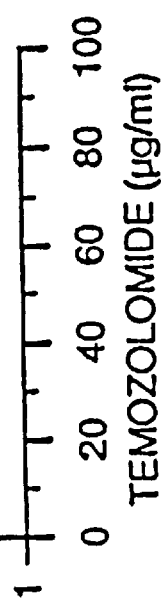
FIG. 16A-2
FIG. 16A-1
EFFECT OF INACTIVATOR PRETREATMENT ON RAJI SENSITIVITY TO TEMOZOLOMIDE

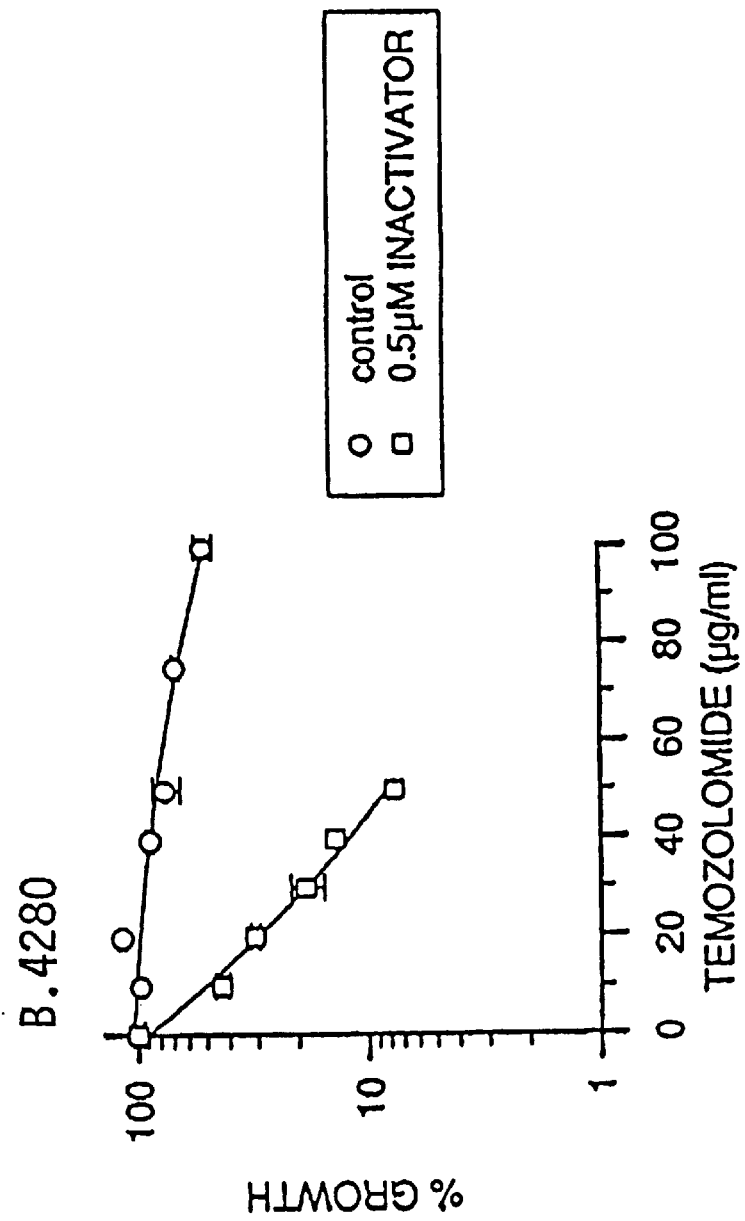

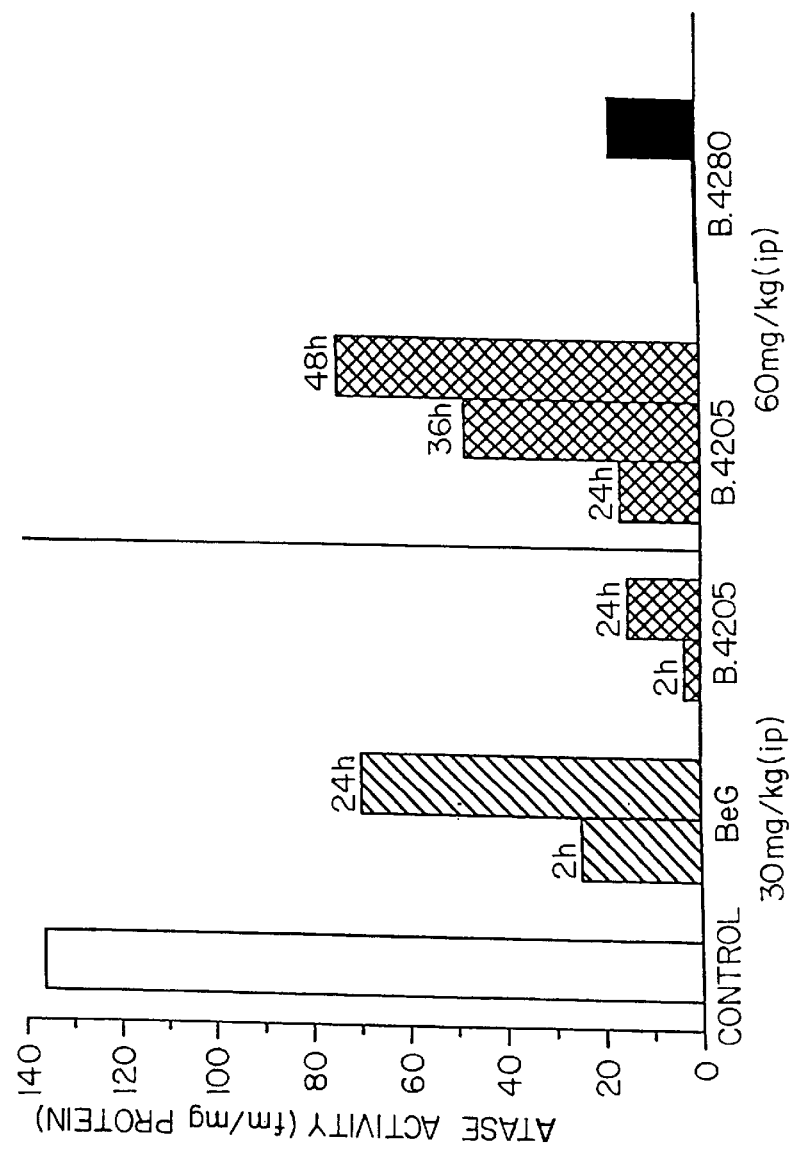

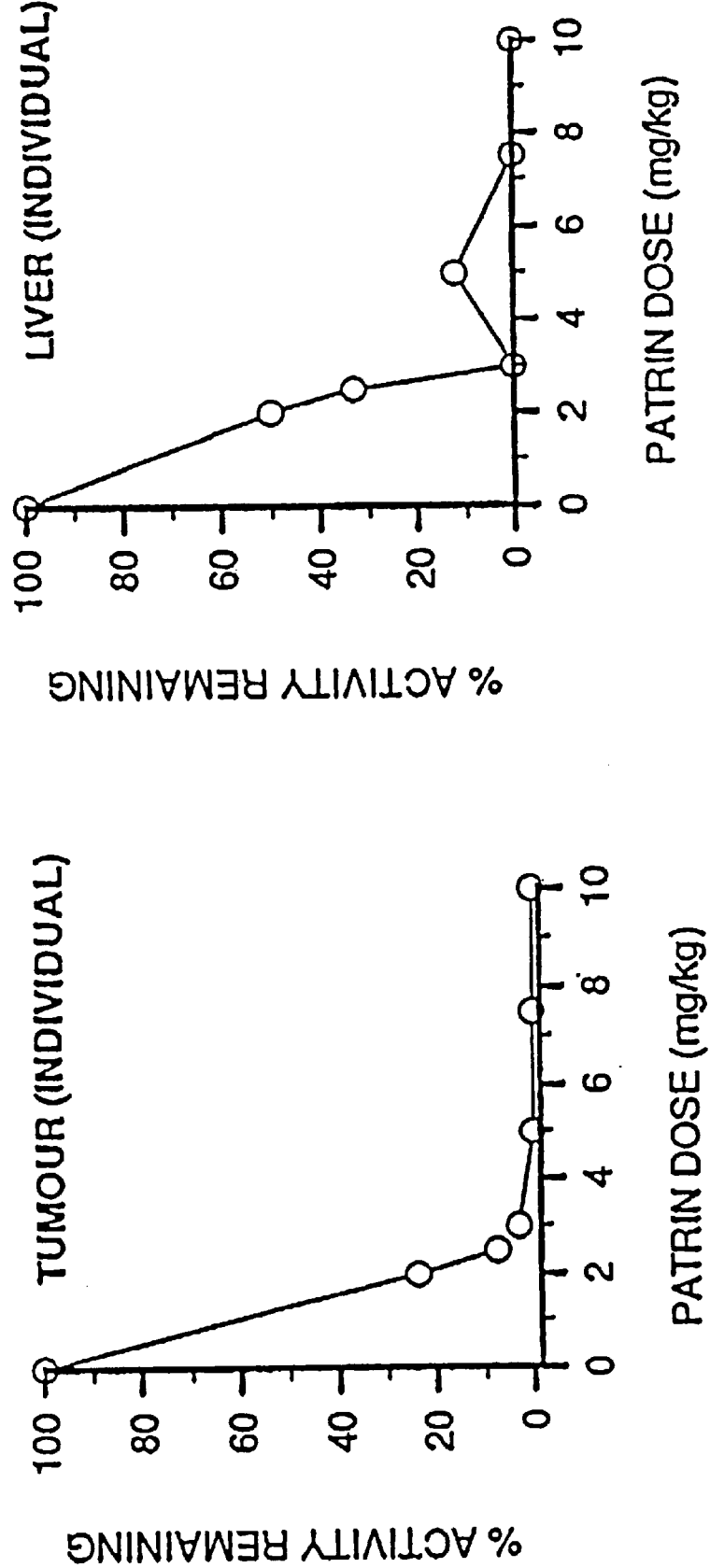

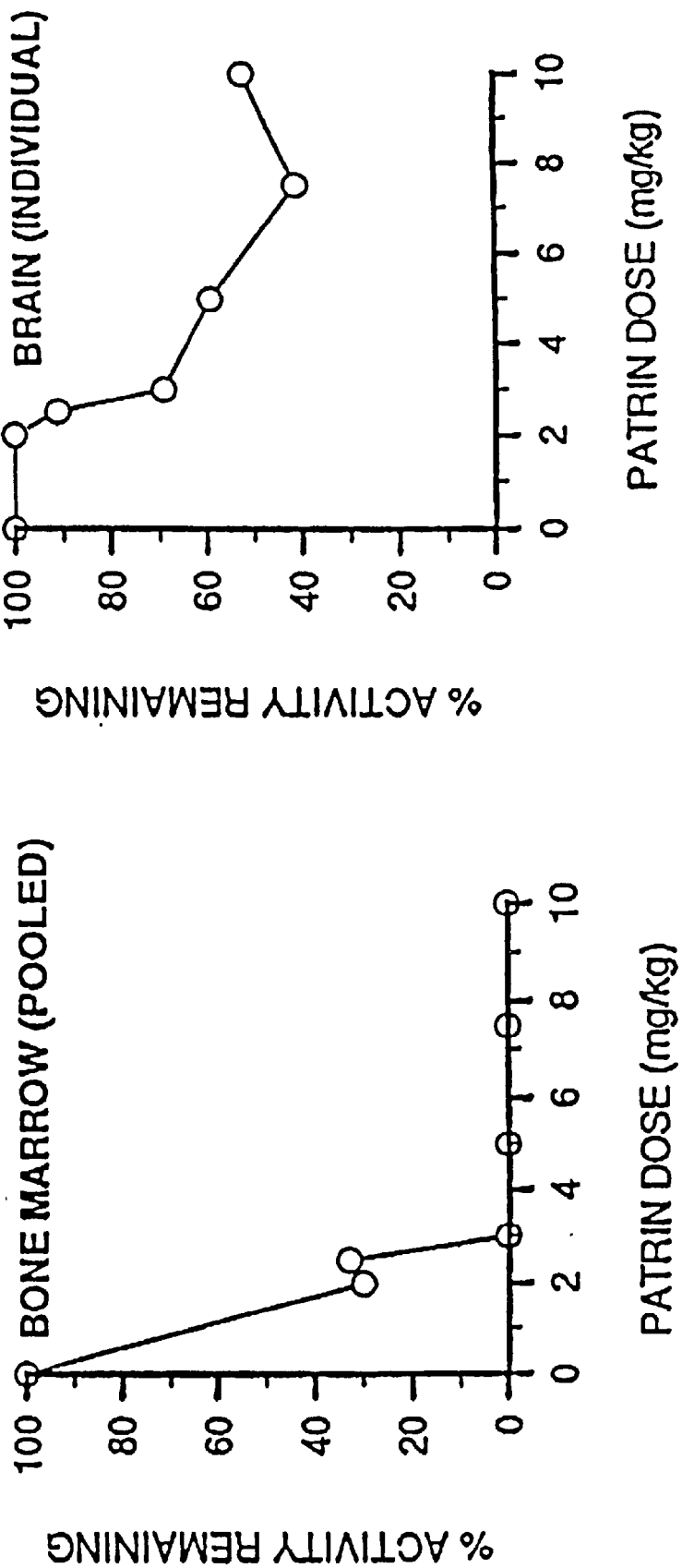

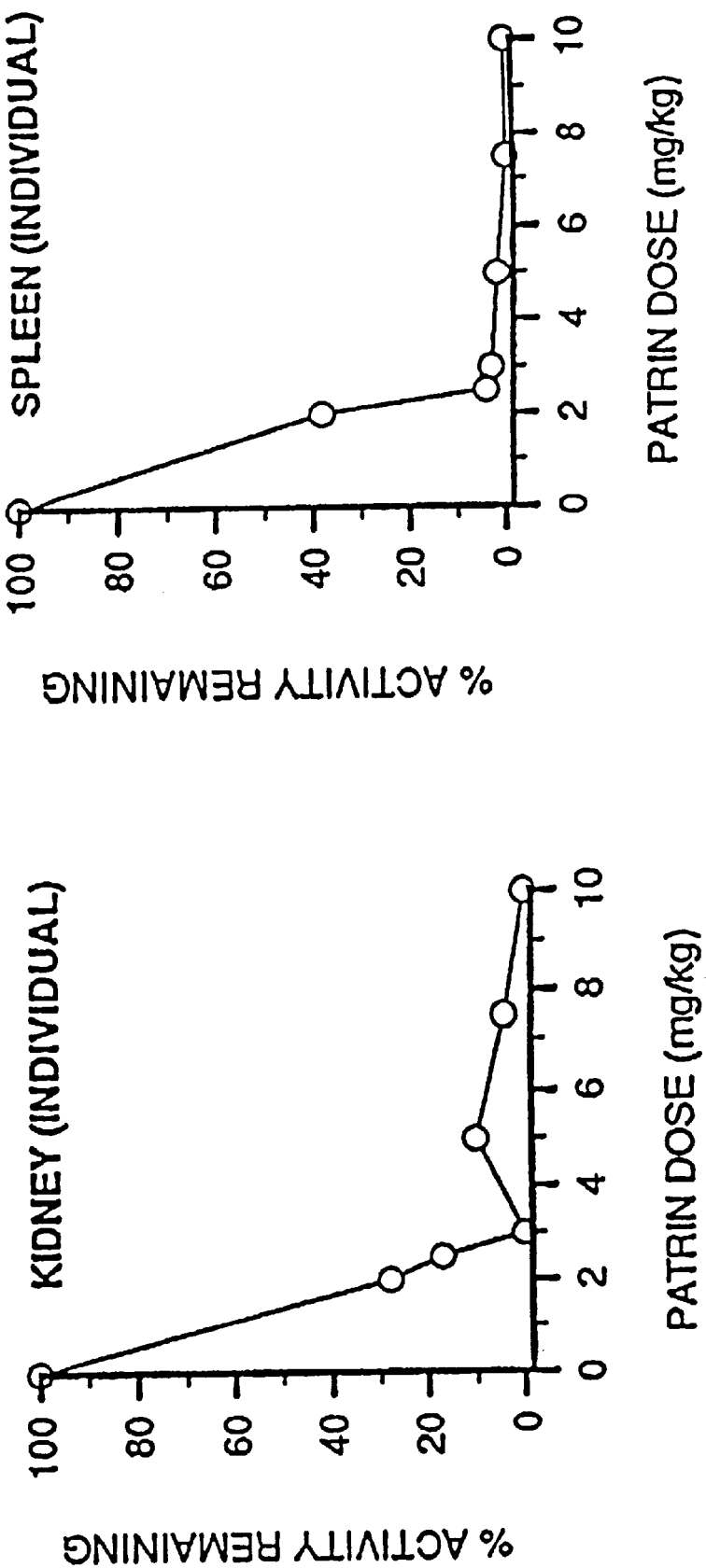

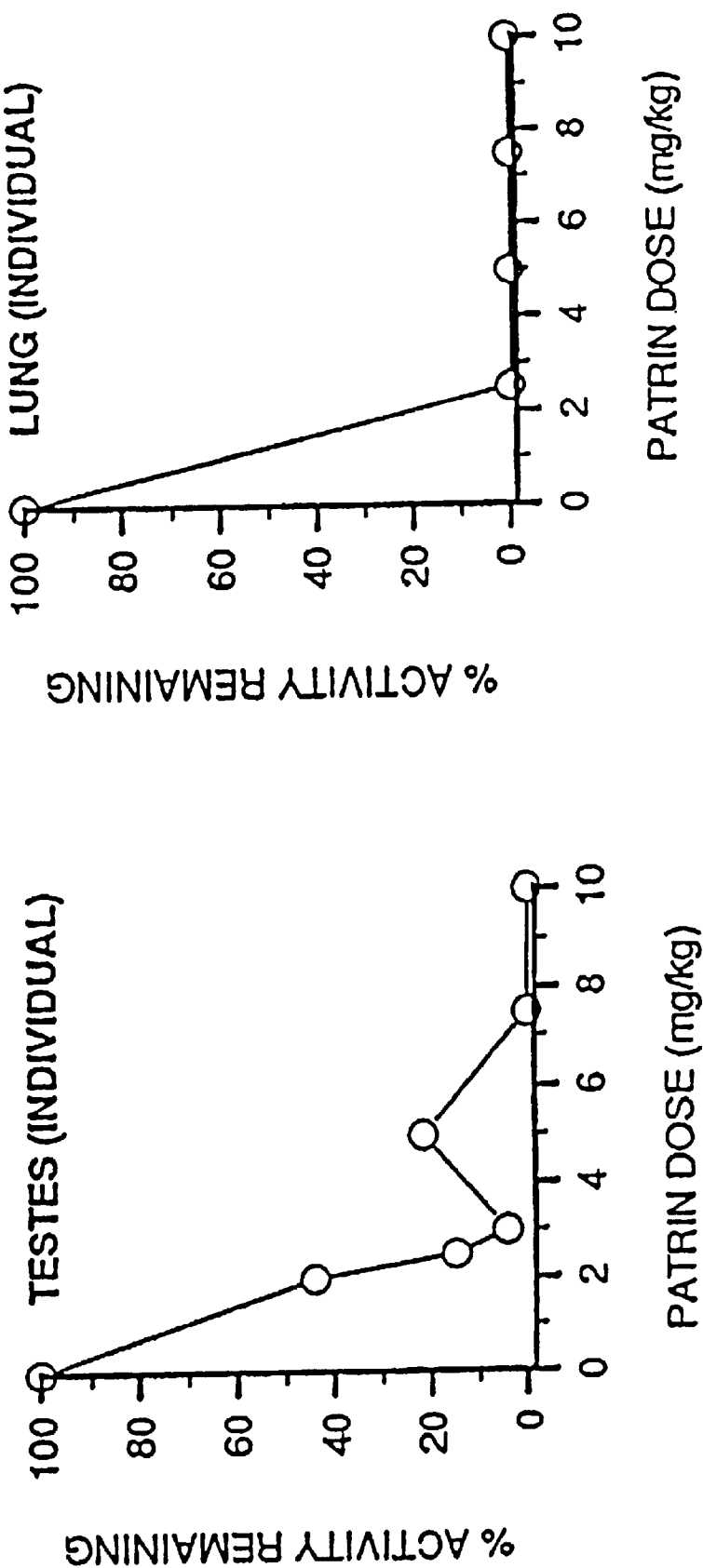

MEAN TUMOUR ACTIVITIES IN NU/NU MICE TREATED OVER 3 DAYS WITH B.4205 OR B.4280 AND TEMOZOLOMIDE

*180 mg/kg B.4205+50 mg/kg TEMOZOLOMIDE GIVEN ON DAY 1 FOLLOWED BY 50 mg/kg TEMOZOLOMIDE ONLY ON DAYS 2 & 3

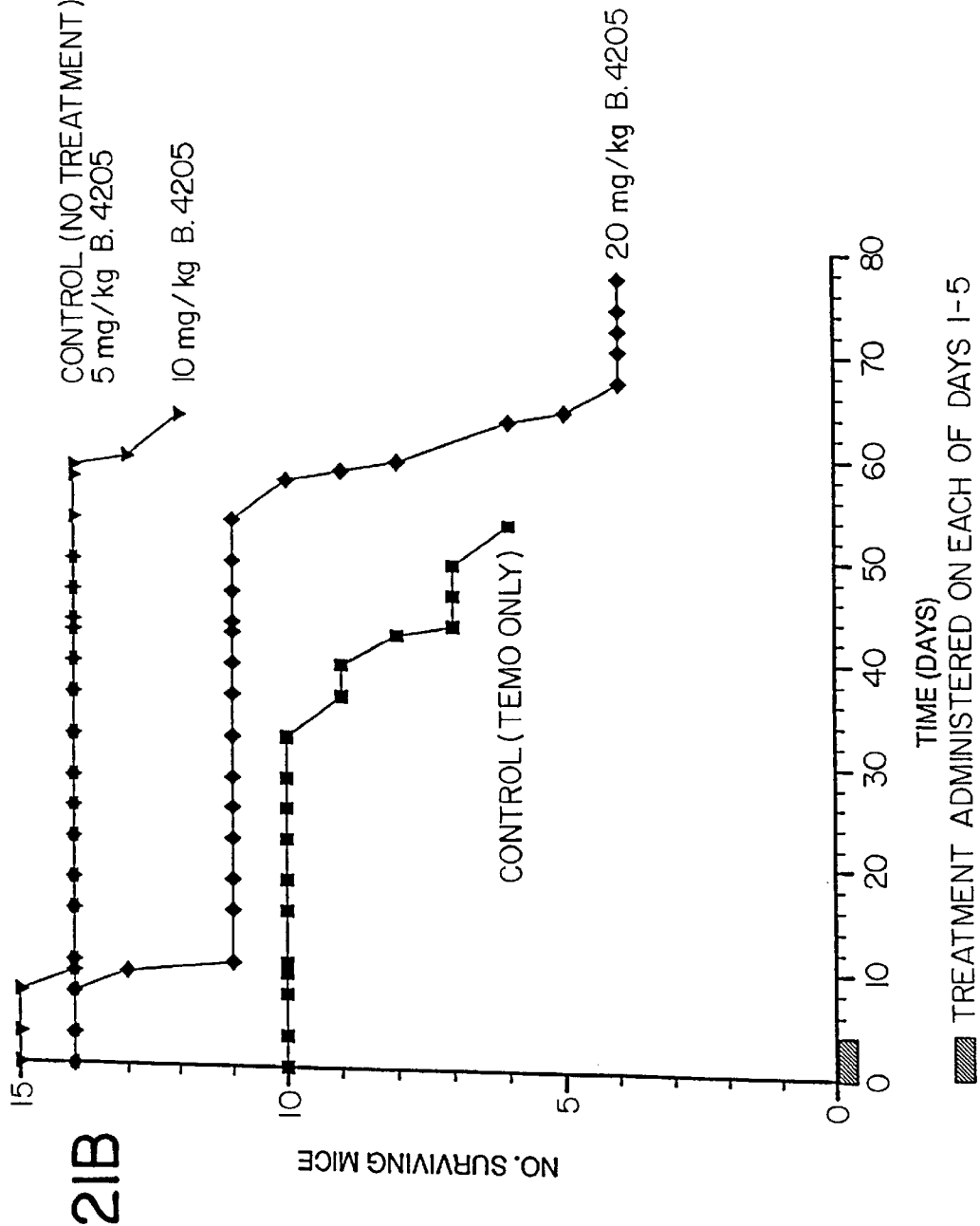

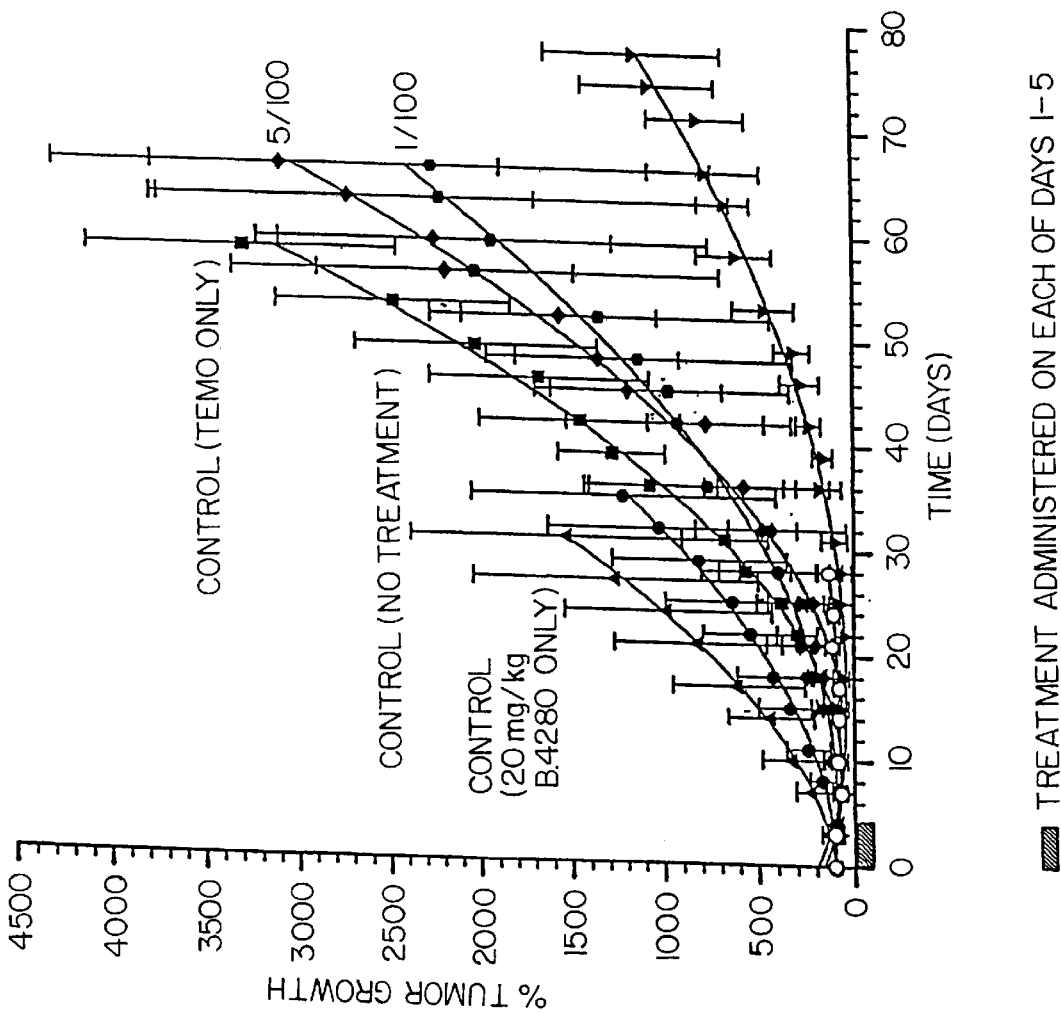
FIG. 22A EFFECT OF B.4280 ON MELANOMA XENOGRAFT SENSITIVITY TO TEMOZOLOMIDE

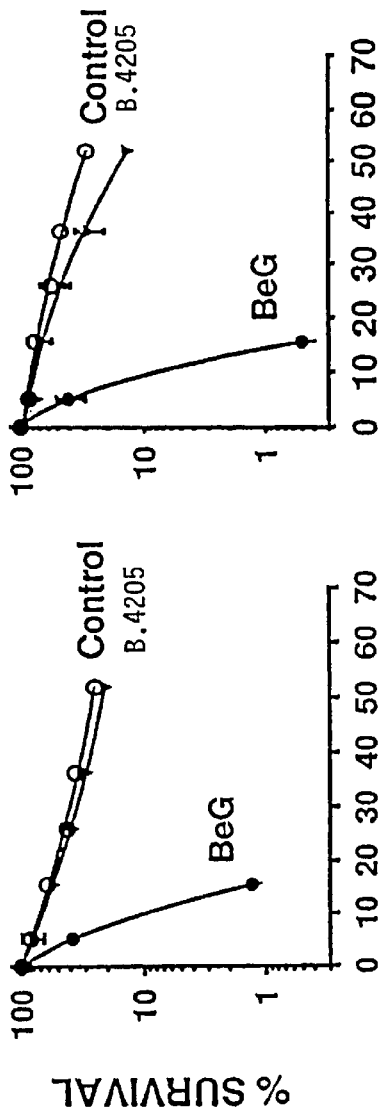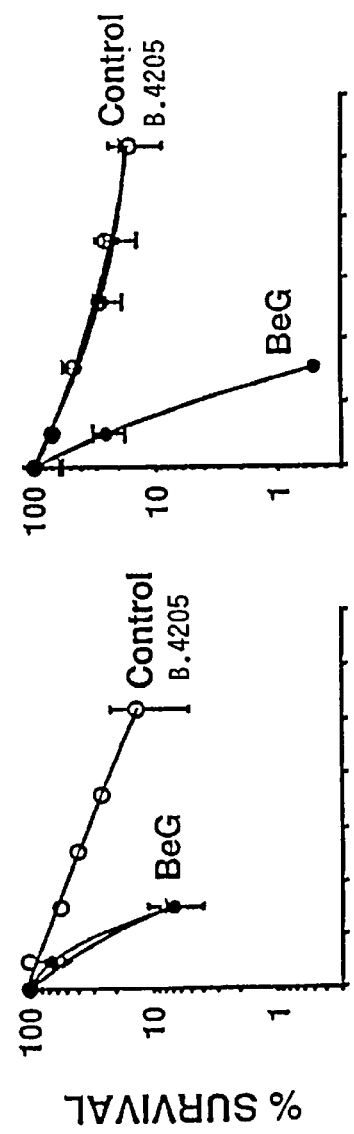
SENSITIZATION OF PRIMARY HUMAN BONE MARROW CELLS (GM-CFC) TO TEMOZOLOMIDE FOLLOWING TREATMENT WITH INACTIVATOR (10 μM)

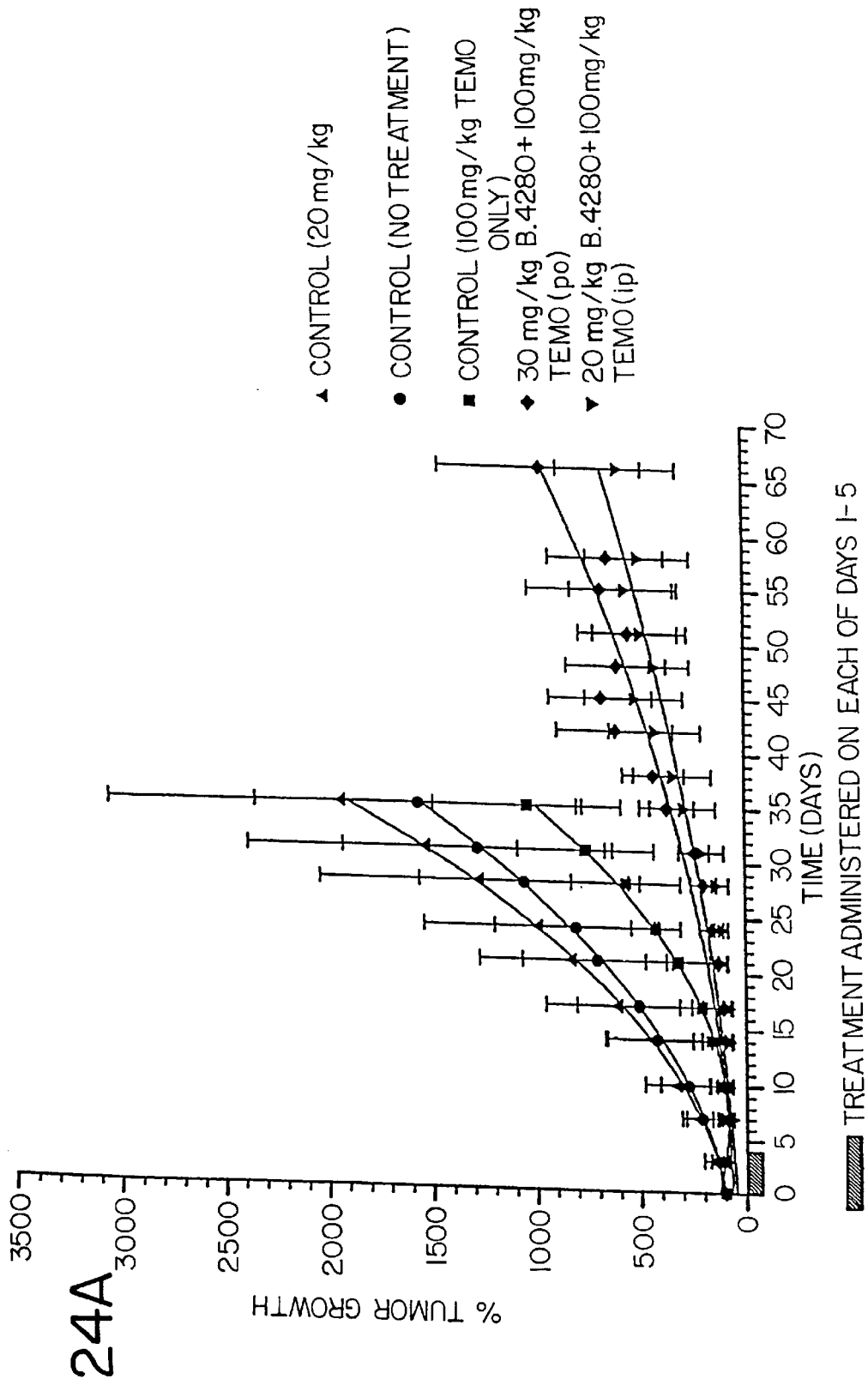

$O^6$-SUBSTITUTED GUANINE DERIVATIVES, A PROCESS FOR THEIR PREPARATION AND THEIR USE IN TREATING TUMOR CELLS

CROSS REFERENCE TO RELATED APPLICATION

This is a continuation-in-part of International Application PCT/IE94/00031, with an international filing date of Jun. 8, 1994.

TECHNICAL FIELD

The present invention relates to $O^6$-substituted guanine derivatives, a process for their preparation and their use in treating tumour cells. In particular, it relates to guanine derivatives having hetarylalkyl or naphthylalkyl substituents in the $O^6$ position, these compounds exhibiting the ability to deplete $O^6$-alkylyguanine-DNA alkyltransferase (ATase) activity in tumour cells.

BACKGROUND ART

It has been suggested to use $O^6$-alkyl guanine derivatives possessing $O^6$-alkylguanine-DNA alkyltransferase depleting activity in order to enhance the effectiveness of chemotherapeutic alkylating agents used for killing tumour cells. There is increasing evidence that in mammalian cells the toxic and mutagenic effects of alkylating agents are to a large extent a consequence of alkylation at the $O^6$-position of guanine in DNA. The repair of $O^6$-alkylguanine is mediated by ATase, a repair protein that acts on the $O^6$-alkylated guanine residues by stoichiometric transfer of the alkyl group to a cysteine residue at the active site of the repair protein in an autoinactivating process. The importance of ATase in protecting cells against the biological effects of alkylating agents has been most clearly demonstrated by the transfer and expression of cloned ATase genes or cDNAs into ATase deficient cells: this confers resistance to a variety of agents, principally those that methylate or chloroethylate DNA. Whilst the mechanism of cell killing by $O^6$-methylguanine in ATase deficient cells is not yet clear, killing by $O^6$-chloroethylguanine occurs through DNA interstrand crosslink formation to a cytosine residue on the opposite strand via a cyclic ethanoguanine intermediate, a process that is prevented by ATase-mediated chloroethyl group removal or complex formation.

The use of $O^6$-methylguanine and $O^6$-n-butylguanine for depleting ATase activity has been investigated (Dolan et al., Cancer Res., (1986) 46, pp. 4500; Dolan et al., Cancer Chemother. Pharmacol., (1989) 25, pp 103. $O^6$-benzylguanine derivatives have been proposed for depleting ATase activity in order to render ATase expressing cells more susceptible to the cytotoxic effects of chloroethylating agents (Moschel et al., J. Med.Chem., 1992, 35, 4486). U.S. Pat. No. 5,091,430 and International Patent Application No. WO 91/13898 Moschel et al. disclose a method for depleting levels of $O^6$-alkylguanine-DNA alkyltransferase in tumour cells in a host which comprises administering to the host an effective amount of a composition containing $O^6$-benzylated guanine derivatives of the following formula:

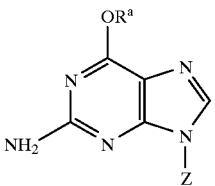

wherein Z is hydrogen, or

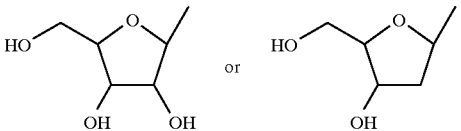

and $R^a$ is a benzyl group or a substituted benzyl group. A benzyl group may be substituted at the ortho, meta or para position with a substituent group such as halogen, nitro, aryl such as phenyl or substituted phenyl, alkyl of 1–4 carbon atoms, alkoxy of 1–4 carbon atoms, alkenyl of up to 4 carbon atoms, alkynyl of up to 4 carbon atoms, amino, monoalkylamino, dialkylamino, trifluoromethyl, hydroxy, hydroxymethyl, and $SO_nR^b$ wherein n is 0, 1, 2 or 3 and $R^b$ is hydrogen, alkyl of 1–4 carbon atoms or aryl. Mi-Young Chae et al., J.Med.Chem., 1994, 37, 342–347—published after the priority date of the present application—describes tests on $O^6$-benzylguanine analogs bearing increasingly bulky substituent groups on the benzene ring or at position 9. Compound No. 6 described therein is $O^6$-(2-pyridylmethyl)guanine, which in this application is called $O^6$-(2-picolyl) guanine. However in the Results and Discussion at pages 342–343 of the Chae et al. paper, Compound No. 6 is not highlighted as being of interest but is grouped among "remaining compounds" which "exhibited intermediate activity" (Page 343 Lines 12–15 of the text). The authors confirm their earlier observations (J.Med.Chem., 1992, 35 4486) that only allyl or benzyl substituents at the $O^6$ position of guanine efficiently inactivated ATase (page 343 lines 21–23 of the text).

$O^6$-benzylguanine has limitations in its use as an ATase inactivator. It is more stable than would be desirable, resulting in a long survival time in an animal to which it is administered. It has a level of potential toxicity both alone and in combination with chloroethylating agents which is also undesirable and which may be related to the survival time.

The compounds of the present application exhibit different ATase inactivating characteristics from $O^6$-benzylguanine and in some cases the activity is up to 8 times greater than that of $O^6$-benzylguanine. Different half-life and toxicity characteristics have also been observed. Therefore, it is an object of the present invention to provide novel compounds useful for depleting ATase activity in order to enhance the effects of chemotherapeutic agents such as chloroethylating or methylating anti-tumour agents.

Another object of the invention is to provide pharmaceutical compositions containing compounds which are useful for depleting ATase activity. A further object of the present invention is to provide a method for depleting ATase activity in tumour cells. A still further object of the invention is to provide a method for treating tumour cells in a host.

DISCLOSURE OF INVENTION

Accordingly, the present invention provides $O^6$-substituted guanine derivatives of formula I:

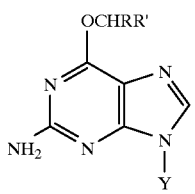

(I)

wherein

Y is H, ribosyl, deoxyribosyl, or R"XCHR'", wherein X is O or S, R" and R'" are alkyl, or substituted derivatives thereof;

R' is H, alkyl or hydroxyalkyl;

R is (i) a cyclic group having at least one 5- or 6-membered heterocyclic ring, optionally with a carbocyclic or heterocyclic ring fused thereto, the or each heterocyclic ring having at least one hetero atom chosen from O, N, or S, or a substituted derivative thereof; or (ii) naphthyl or a substituted derivative thereof;

and pharmaceutically acceptable salts thereof.

R may suitably be a 5- or 6-membered heterocyclic ring or a benzo derivative thereof, in which latter case the $\underline{O}^6$-alkyl guanine moiety may be attached to R at either the heterocyclic or the benzene ring.

In preferred embodiments, R is a 5-membered ring containing S or O, with or without a second ring fused thereto.

Preferably, R is a heterocyclic ring having at least one S atom; more preferably, R is a 5-membered heterocyclic ring having at least one S atom; and most preferably, R is a thiophene ring or a substituted derivative thereof.

Alternatively, R may be a heterocyclic ring having at least one O atom, particularly, a 5-membered heterocyclic ring having at least one O atom and more particularly R may be a furan ring or a substituted derivative thereof.

As another alternative, R may be a heterocyclic ring having at least one N atom, particularly R may be a 6-membered heterocyclic ring having at least one N atom and in particular, R may be a pyridine ring. In the definition of Y, the term "substituted derivative" includes substitution by one or more of the following groups: hydroxy, alkoxy, amino, alkylamino, amido or ureido.

In the definition of R, the term "substituted derivative" includes substitution of the heterocyclic rings and/or carbocyclic ring(s) by one or more of the following groups: alkyl, alkenyl, alkynyl, halo, haloalkyl, nitro, cyano, hydroxyalkyl, $SO_nR''''$ where $R''''$ is alkyl and n=0,1 or 2, or a carboxyl or ester group of the formula —$COOR^5$ wherein $R^5$ is H or alkyl. Halo, haloalkyl, cyano, $SO_nR''''$ (as defined above) and —$COOR^5$ wherein $R^5$ is alkyl are preferred substituents.

An alkyl, alkenyl, or alkynyl group preferably contains from 1 to 20, more preferably from 1 to 10 and most preferably from 1 to 5 carbon atoms. Halo includes iodo, bromo, chloro or fluoro.

Examples of compounds of the invention (together with Compounds B.4214 and B.4218 not covered by the present application) are shown in Table 1.

TABLE 1

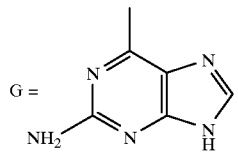

| | | |
|---|---|---|
| B.4203 | $\underline{O}^6$-furfurylguanine | 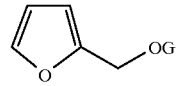 |
| B.4205 | $\underline{O}^6$-thenylguanine | 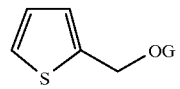 |
| B.4206 | $\underline{O}^6$-(3-thienylmethyl)guanine | 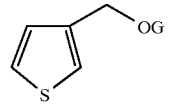 |
| B.4209 | $\underline{O}^6$-(3-furylmethyl)guanine | 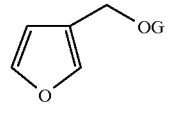 |
| B.4210 | $\underline{O}^6$-(2-picolyl)guanine | 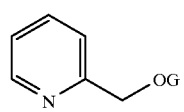 |

TABLE 1-continued
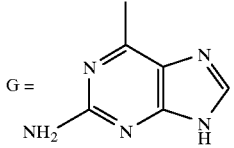
G =
| | | |
|---|---|---|
| B.4211 | $O^6$-(3-picolyl)guanine | 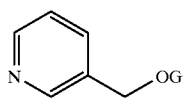 |
| B.4212 | $O^6$-piperonylguanine | 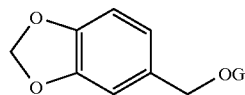 |
| B.4213 | $O^6$-(2-naphthylmethyl)guanine | 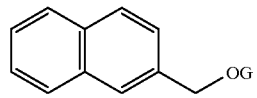 |
| B.4214 | DL-$O^6$-(α-methylbenzyl)guanine | 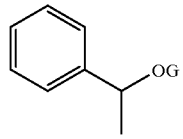 |
| B.4217 | DL-$O^6$-(α-methylthenyl)guanine | 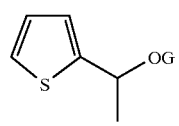 |
| B.4218 | $O^6$-(2-methylbenzyl)guanine | 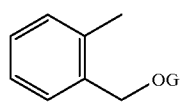 |
| B.4219 | DL-$O^6$-[1-(3-thienyl)ethyl]guanine | 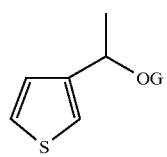 |
| B.4220 | $O^6$-(5-methylthenyl)guanine | 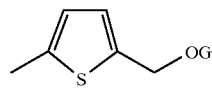 |
| B.4221 | $O^6$-(5-methylfurfuryl)guanine | 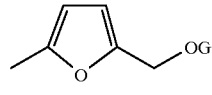 |
| B.4222 | $O^6$-(3-methylthenyl)guanine | 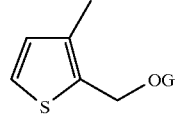 |

TABLE 1-continued
G = 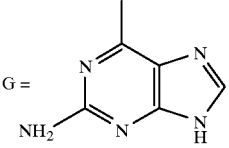
| | | |
|---|---|---|
| B.4226 | O⁶-(2-benzo[b]thienylmethyl)guanine | 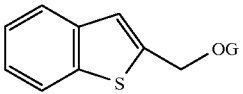 |
| B.4229 | O⁶-(5-methoxycarbonylfurfuryl)guanine | 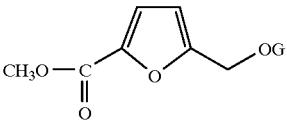 |
| B.4234 | O⁶-(5-carboxyfurfuryl)guanine | 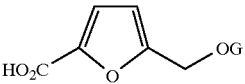 |
| B.4265 | O⁶-(1-naphthylmethyl)guanine | 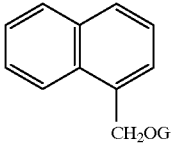 |
| B.4266 | O⁶-(2-benzofuranylmethyl)guanine | 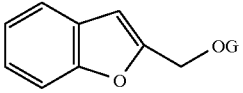 |
| B.4268 | O⁶-piperonylguanosine | 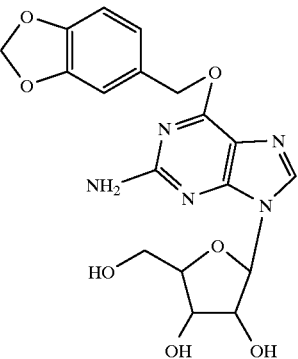 |
| B.4269 | O⁶-(5-bromothenyl)guanine | 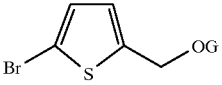 |
| B.4271 | O⁶-(5-azapiperonyl)guanine | 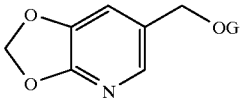 |
| B.4273 | O⁶-(5-cyanofurfuryl)guanine | 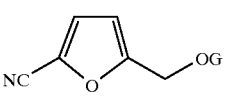 |

TABLE 1-continued

G = 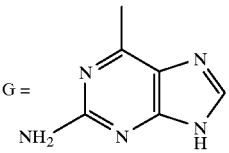

| | | |
|---|---|---|
| B.4274 | O⁶-(5-oxazolylmethyl)guanine | 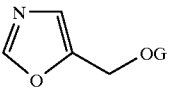 |
| B.4275 | O⁶-(5-thiazolylmethyl)guanine | 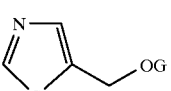 |
| B.4276 | O⁶-(2-benzo[b]thienylmethyl)guanosine | 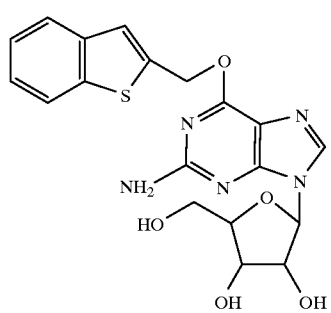 |
| B.4277 | O⁶-(4-picolyl)guanine | 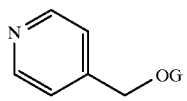 |
| B.4278 | O⁶(1-methyl-4-nitropyrrol-2-ylmethyl)guanine | 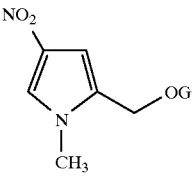 |
| B.4279 | O⁶-thenylguanosine | 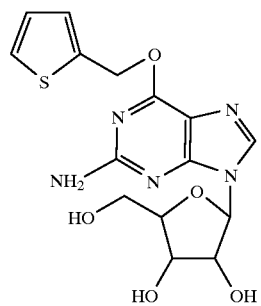 |

Among the compounds in Table 1 compounds B.4214 and B.4218 are not compounds of the invention. Compound B.4210 (ie the compound of Formula I in which R is 2-pyridyl, R' is H and Y is H) is not a preferred compound of the invention.

Particularly preferred compounds of the invention include:
B.4205 O⁶-thenylguanine
B.4206 O⁶-(3-thienylmethyl)guanine
B.4212 O⁶-piperonylguanine
B.4226 O⁶-(2-benzo[b]thienylmethyl)guanine
B.4266 O⁶-(2-benzofuranylmethyl)guanine
B.4275 O⁶-(5-thiazolylmethyl)guanine and compounds substituted in the heterocyclic ring of R by a halo, cyano or ester group, including B.4229 O⁶-(5-methoxycarbonylfurfuryl)guanine B.4269 $\underline{O}^6$-(5-bromothenyl)guanine
B.4273 $\underline{O}^6$-(5-cyanofurfuryl)guanine.
Other preferred compounds include
B.4209 $\underline{O}^6$-3-furylmethylguanine
B.4276 $\underline{O}^6$-(2-benzo[b]thienylmethyl)guanosine
B.4277 $\underline{O}^6$(4-picolyl)guanine.

The most preferred compounds of the invention are those that inactivate ATase in vitro and/or in mammalian cells and/or tumour xenografts more effectively than $\underline{O}^6$-benzylguanine (BeG) and that sensitise mammalian cells and/or tumour xenografts to the killing or growth inhibitory effects of nitrosoureas and or methylating agents more effectively than BeG. Preferred compounds should also have, in comparison to BeG, reduced toxicity to normal tissues and/or to the entire organism when used in combination with such agents. Preferred compounds should not themselves be toxic or show more than minimal toxicity at the doses required to inactivate ATase, neither should any hydrolysis products of a preferred compound that was chemically unstable be toxic. Although the invention is not limited by any theory, preferred compounds may need to be less stable than BeG so that they undergo spontaneous chemical degradation soon after achieving maximal inactivation of ATase: in this way any action of metabolic processes that might act on the agent to generate toxic species would be minimised. Preferred compounds should be less able to sensitise human bone marrow or other normal cell types to the toxic effects of alkylating agents so that they would not exacerbate the known toxicity or generate new toxicities of these agents in normal human tissues.

Preferred compounds of the invention include those having a relatively low $I_{50}$ value in Table 4 herein (e.g. below 1.0 $\mu$M, more particularly below 0.04 $\mu$M) and/or having a relatively short half life in Buffer I (representing conditions for an in vitro assay) and/or Phosphate buffered saline (PBS) (representing conditions in physiological medium) in Table 4 herein (e.g. below 20 hours in Buffer I or below 16 hours in PBS).

A relatively short half-life can be regarded as an indicator that a compound of the invention would be less stable than $\underline{O}^6$-benzylguanine due to the reactivity of RR'CH— and would tend to break down by hydrolysis in physiological medium.

The influence of the group RR'CH— in the compounds of formula I enabling them to act as ATase inhibitors is determined by electronic, steric and physicochemical factors. Steric factors may be related to the nature of the environment of the cysteine receptor site in ATase. Preferably R' is H. A secondary carbon atom attached to $\underline{O}^6$ (as in the DL compounds B.4214 or B.4217) has been found to reduce greatly the inactivating activity, probably because of the bulk of the substituent.

Preferably the cyclic group in R does not have a methyl group in the vicinal position (as in B.4222) although the influence of vicinal substitution is evidently much less when R is heterocyclic than in the naphthyl isomers B.4213 and B.4265.

Physicochemical factors such as stability, solubility and water-lipid partition are relevant to the selection of compounds for use in vivo, affecting formulation, absorption and transport, for example. Selection of compounds may also be influenced by their differential distribution into different tissues.

One embodiment of the invention provides a pharmaceutical composition containing compounds of formula 1, wherein Y, R and R' are as defined above, or a pharmaceutically acceptable salt thereof, and a pharmaceutically acceptable excipient. Optionally the composition may also contain an alkylating agent such as a chloroethylating or methylating agent.

In a further embodiment, the present invention provides a method for depleting ATase activity in a host comprising administering to the host an effective amount of a composition containing a compound of formula 1 wherein Y, R and R' are as defined above, or a pharmaceutically acceptable salt thereof, more particularly a pharmaceutical composition as defined above. This method may alternatively be defined as a method of depleting ATase mediated DNA repair activity in a host.

The invention further provides a method for treating tumour cells in a host comprising administering to the host an effective amount of a composition containing a compound of formula I wherein Y, R and R' are as defined above or a pharmaceutically acceptable salt thereof, more particularly a pharmaceutical composition as defined above and administering to the host an effective amount of a composition containing an alkylating agent. The method may be used for treatment of neoplasms including those which are known to be sensitive to the action of alkylating agents e.g. melanoma and glioma and others whose resistance to treatment with alkylating agents alone may be overcome by the use of an inactivator according to the invention.

The invention also provides a process for preparing compounds of formula I comprising the steps of: reacting sodium hydride with a solution of RR' CHOH (wherein R and R' are as defined above) in an organic solvent, preferably at or below room temperature; adding 2-amino-N,N,N-trimethyl-1H-purin-6-aminium chloride or 2-amino-6-chloropurine riboside; treating the reaction mixture with weak acid and ether; and extracting the desired product.

BRIEF DESCRIPTION OF DRAWINGS

The invention shall be described in greater detail with reference to the accompanying drawings in which:

FIG. 1 is a graph of percentage residual activity of purified recombinant human ATase following incubation with different concentrations of various inactivators. Each point shows the mean of 'measurements. The line at 50% residual activity is used for calculating $I_{50}$ values i.e. the concentration of inactivator required to produce a 50% reduction in ATase activity.

FIG. 3 is four graphs of percentages cell growth, against alkylating agent concentration ($\mu$M), showing the effect of BeG and B.4205 at four different concentrations (0.1, 0.5,1.0 and 5.0 $\mu$M) on sensitization of Raji cells to temozolomide.

FIG. 8 is a diagram of ATase activity (fm/mg) against time (hours) showing the depletion of ATase activity in A375 xenografts in nude mice for untreated controls, corn oil treated controls and BeG (30 mg/kg) and B4205 (30 mg/kg) treated extracts.

Figure 9A:
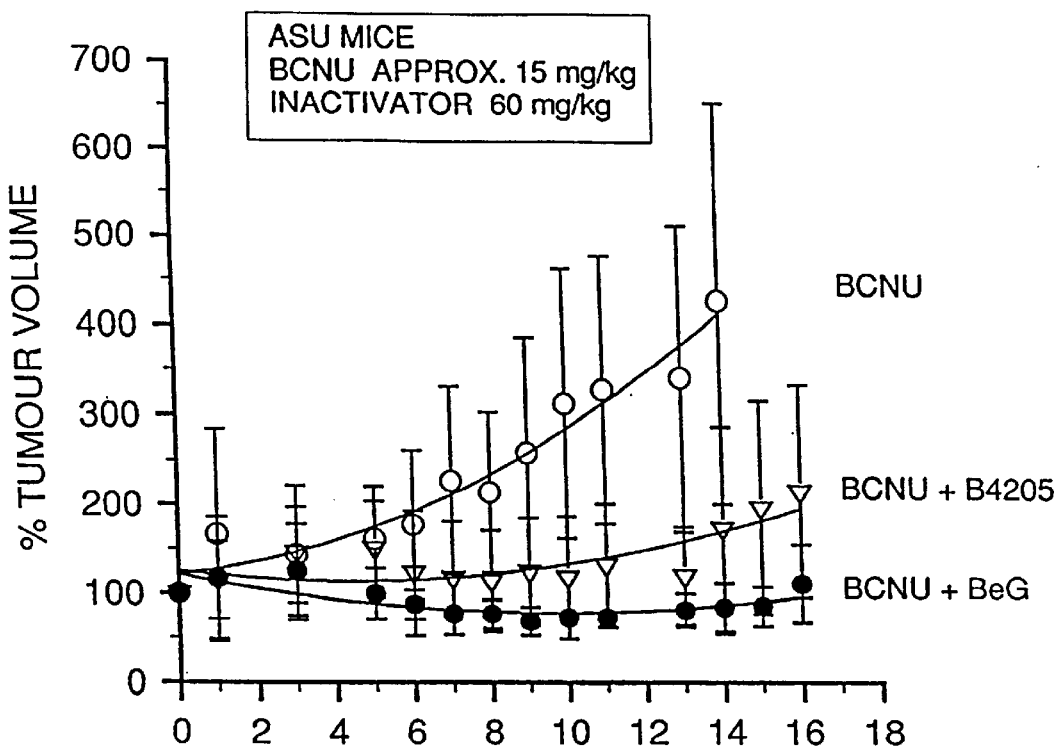
FIG. 9 is graphs of results of xenograft studies. The top graph shows percentage tumour volume against time (days) for A375 tumour xenografts in nude mice treated with BCNU alone, with BeG in combination with BCNU, and B.4205 in combination with BCNU. The lower graph shows the number of surviving mice in each treatment group against time (days) following the treatments illustrated in the top graph.
Figure 9B:
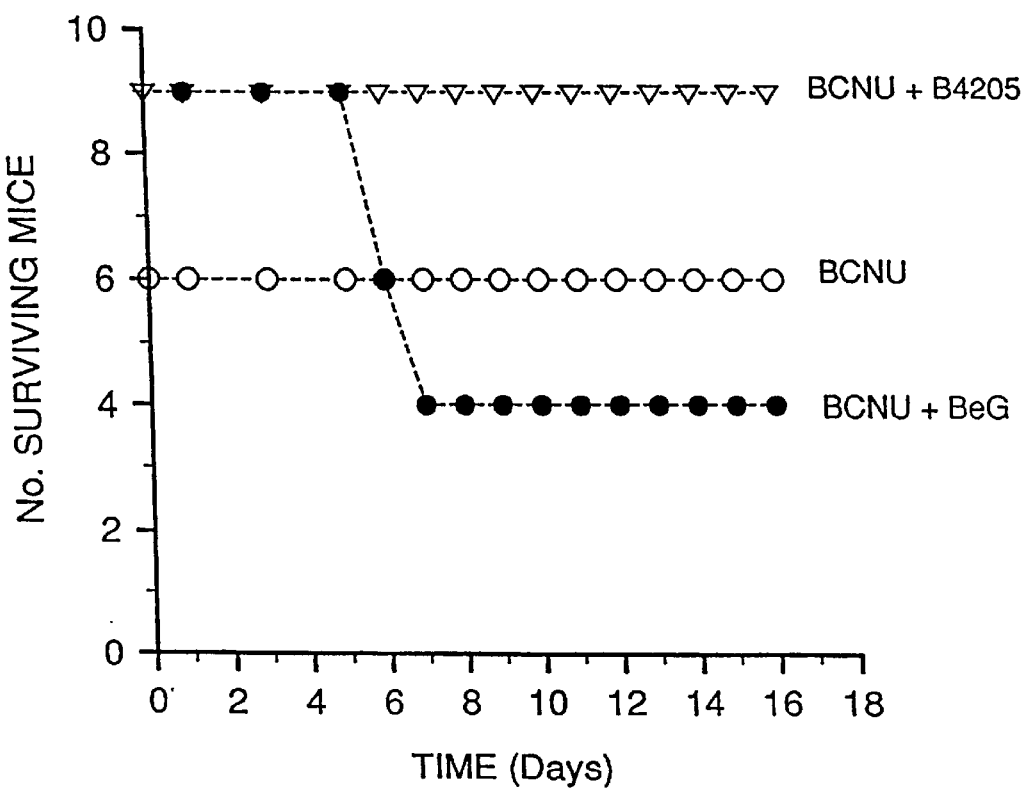

The particulars for FIG. 9 are as follows:

Mice: ASU; BCNU concentration (mg/kg): approx 15; Inactivator (mg/kg): 60.

Figure 10A:
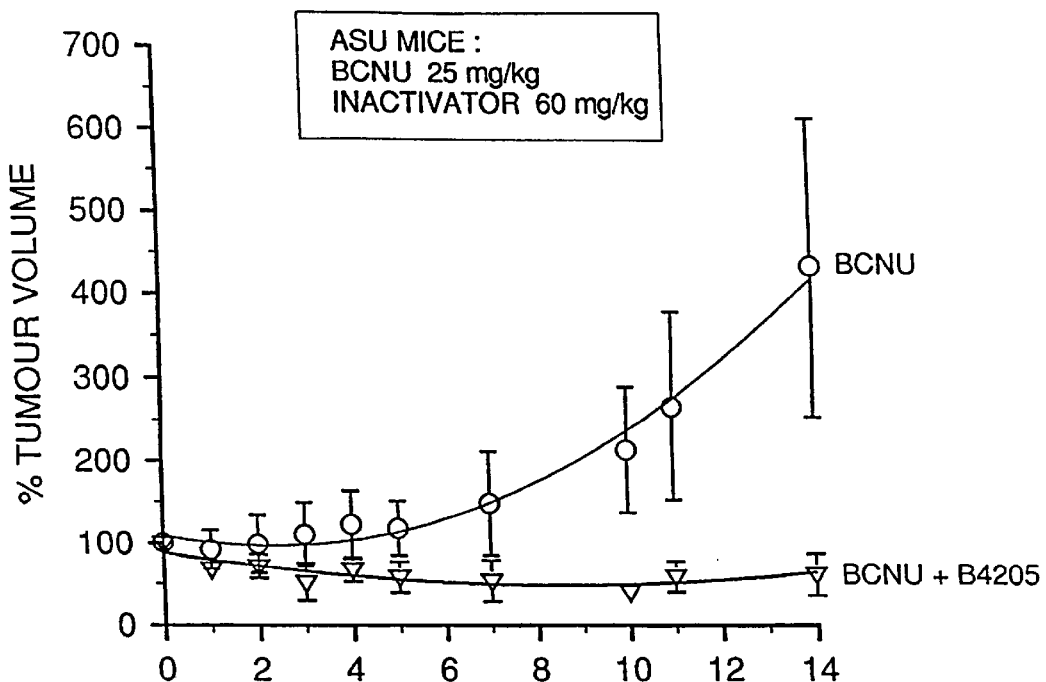
Figure 10B:
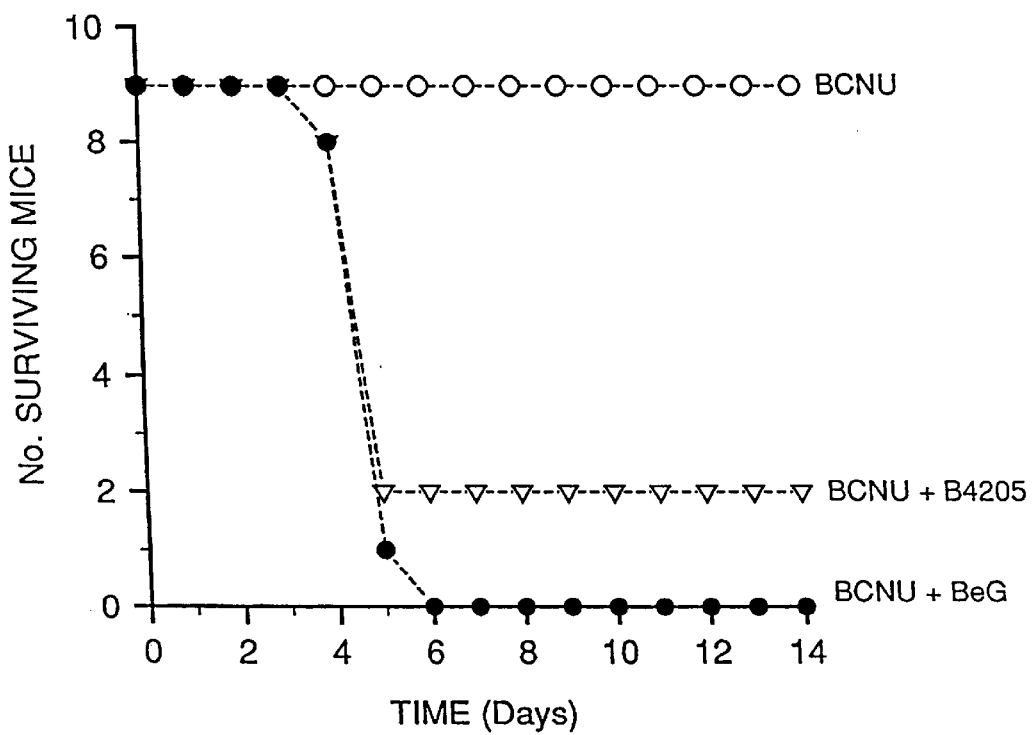

FIG. 10 is two graphs of results of xenograft studies similar to those of FIG. 9. The particulars for FIG. 10 are as follows:

Mice: ASU; BCNU Concentration (mg/kg) 25; Inactivator (mg/kg): 60.

FIG. 11 is two graphs of results of xenograft studies similar to those of FIG. 9. The particulars for FIG. 11 are as follows:

Mice: OLAC; BCNU Concentration (mg/kg): 10; Inactivator (mg/kg): 30.

Figure 12A:
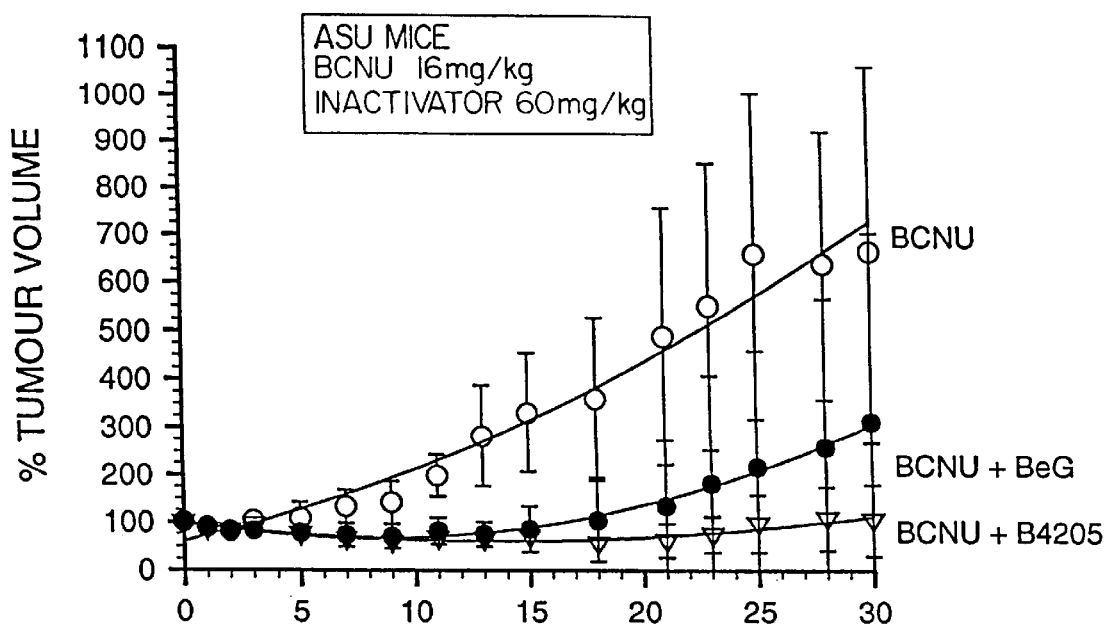
Figure 12B:
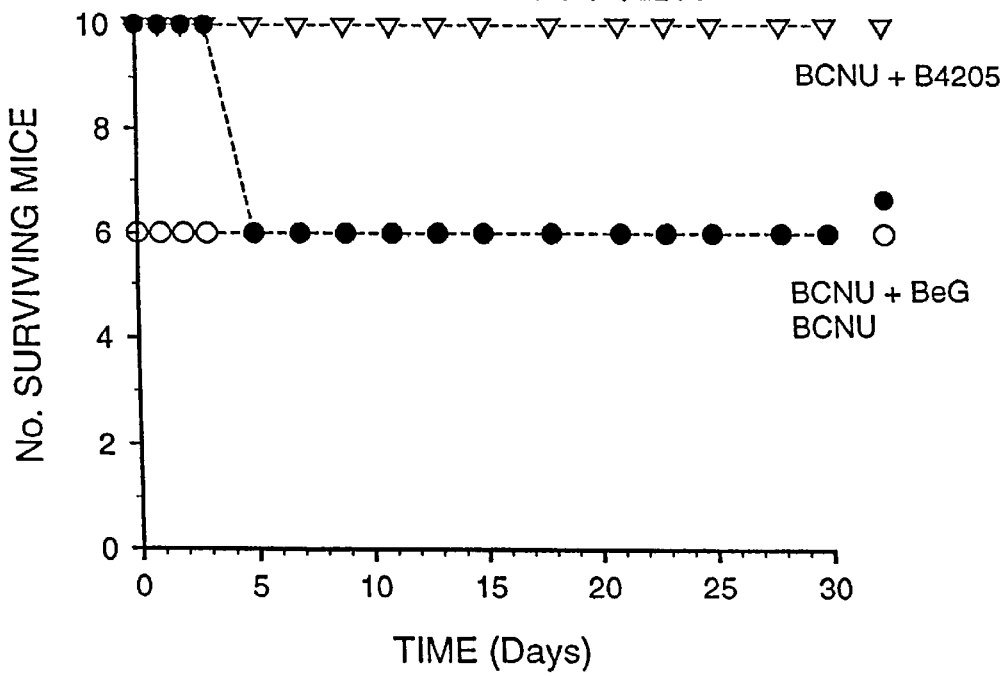

FIG. 12 is two graphs of results of xenograft studies similar to those of FIG. 9. The particulars for FIG. 13 are as follows:

Mice: ASU; BCNU Concentration (mg/kg): 16; Inactivator (mg/kg): 60.

Figure 13A:
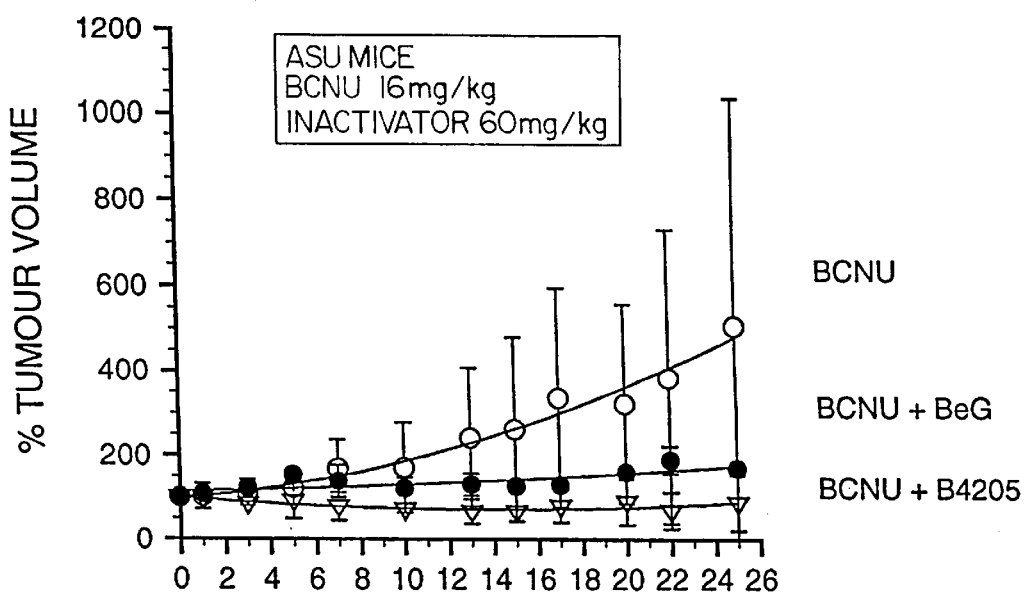
Figure 13B:
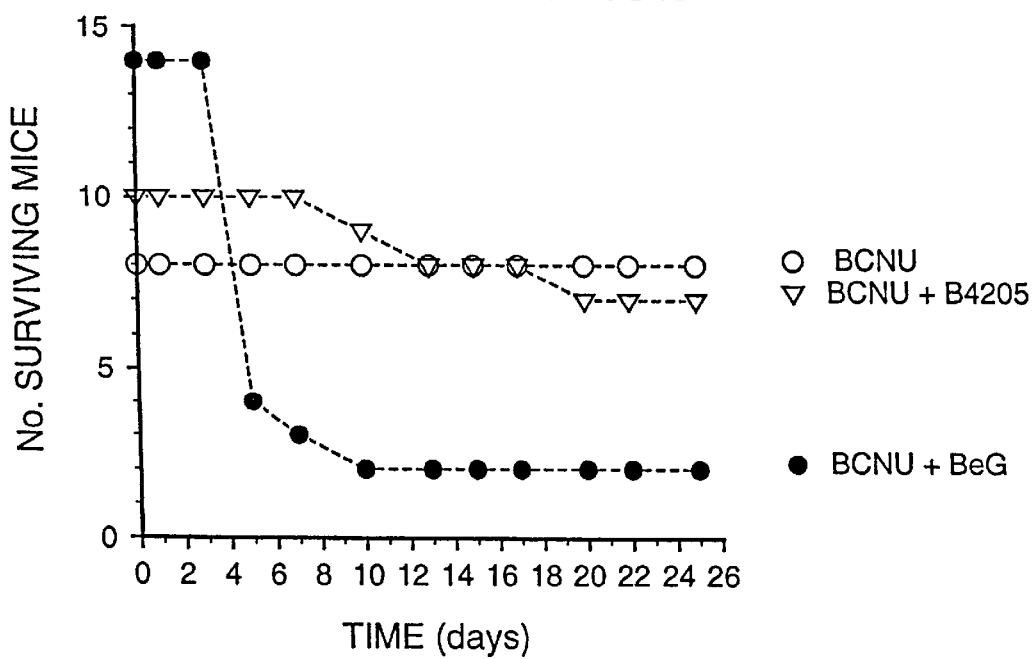

FIG. 13 is two graphs of results of xenograft studies similar to those of FIG. 9. The particulars for FIG. 13 are as follows:

Mice: ASU; BCNU Concentration (mg/kg): 16; Inactivator (mg/kg): 60.

Figure 14A:
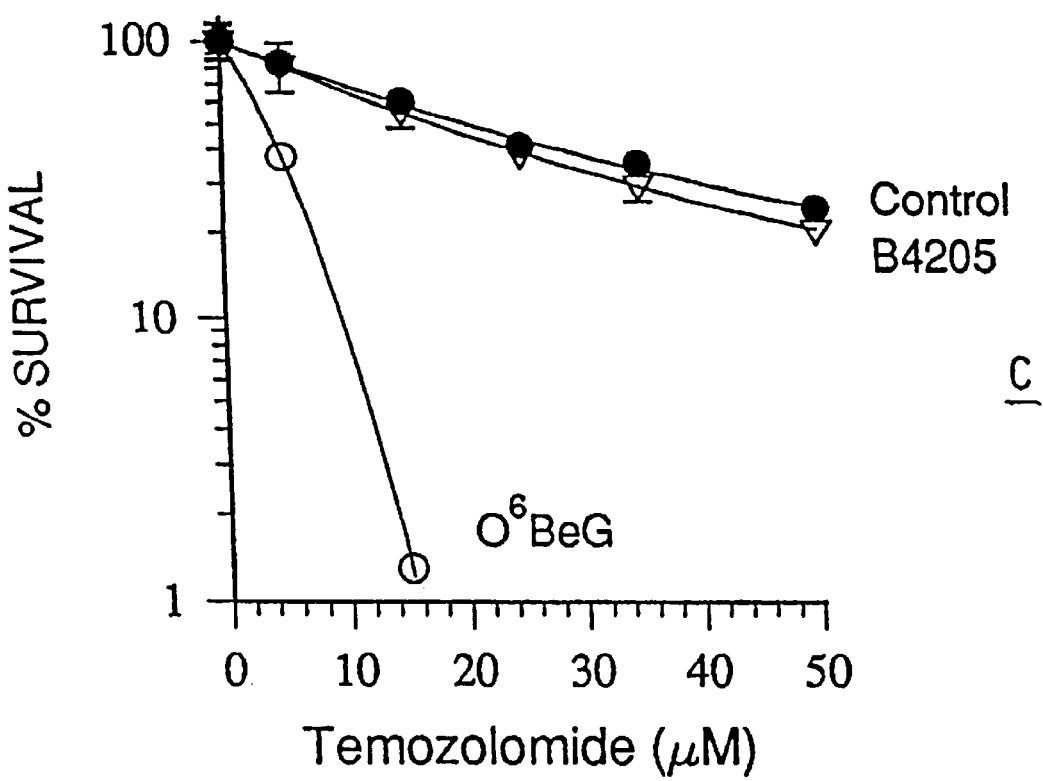
Figure 14B:
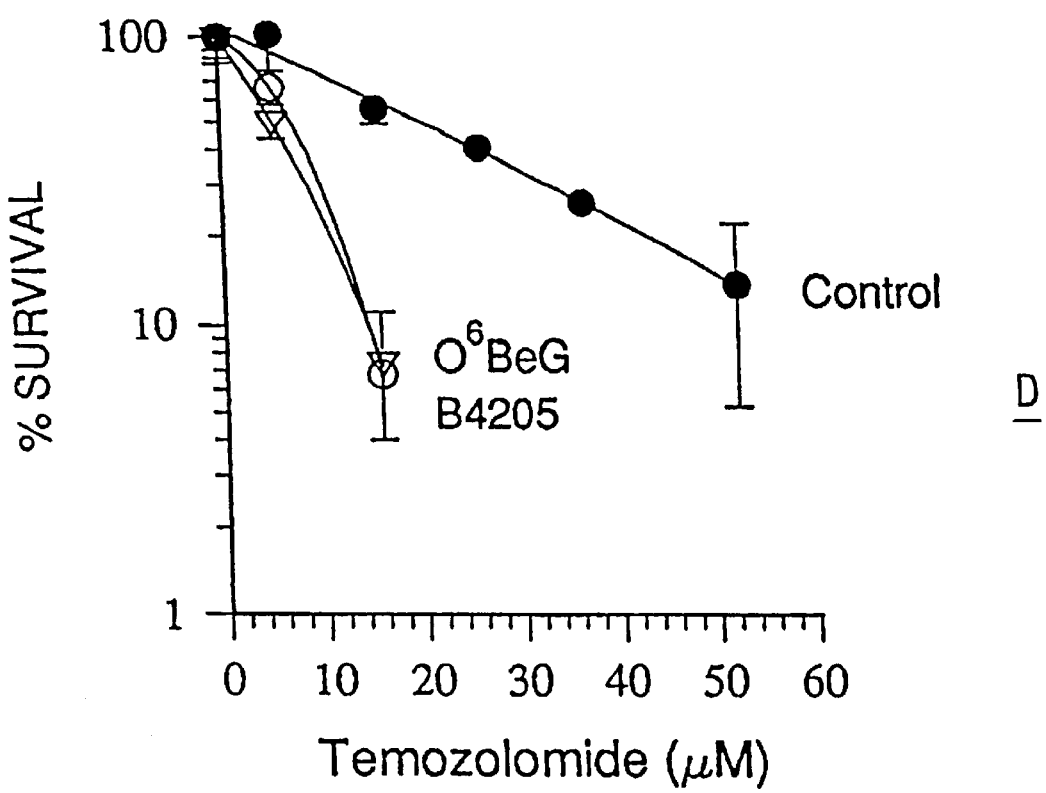
Figure 14C:
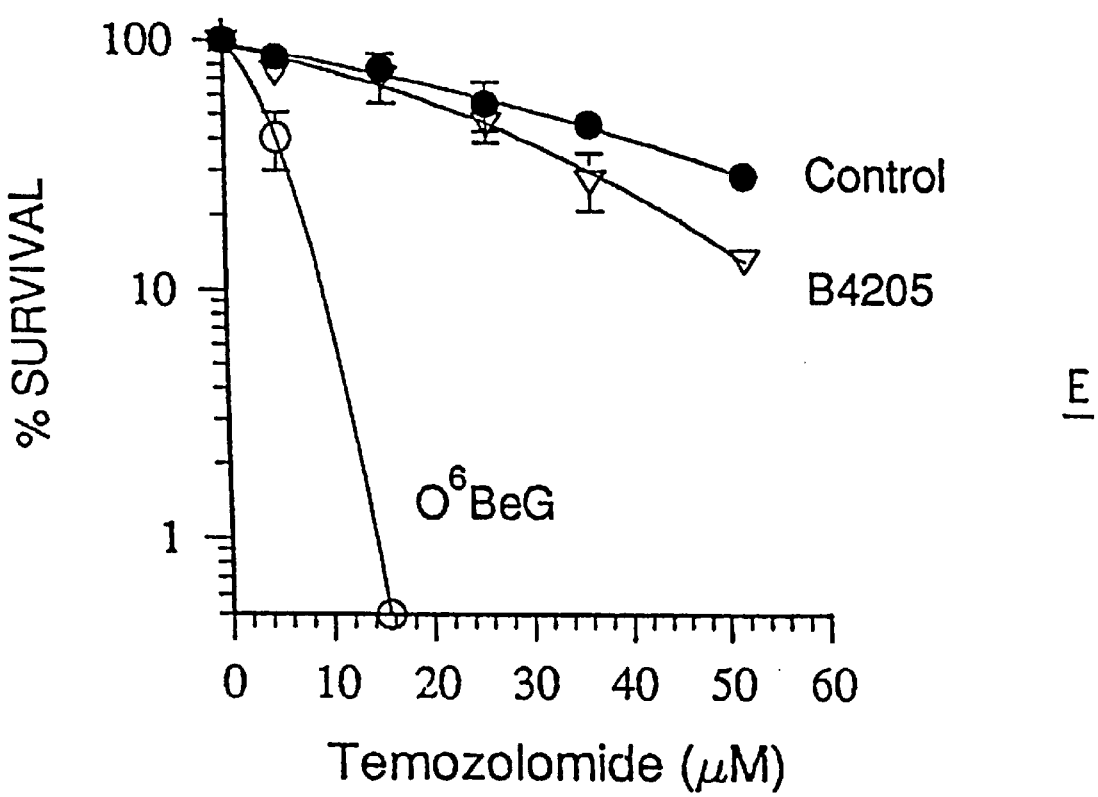

FIG. 14 is 3 graphs of percentage survival against temozolomide concentration ($\mu$M), showing the survival of bone marrow cells following treatment with inactivator (10 $\mu$M) or DMSO (control) in combination with increasing doses of temozolomide.

Figure 15:
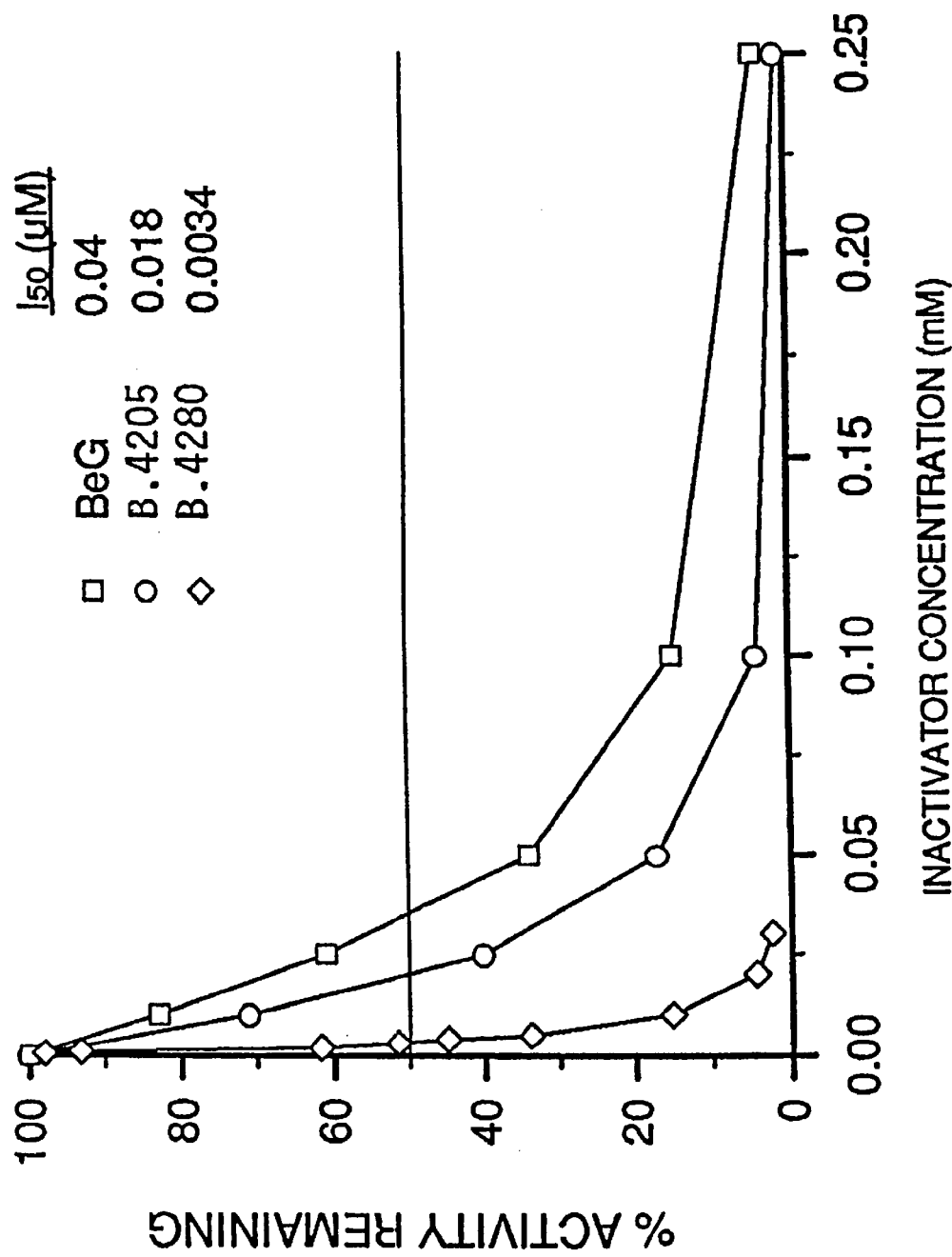

FIG. 15 is a graph similar to FIG. 1 showing the effect of preincubation of pure human recombinant ATase with increasing concentrations of inactivators BeG, B.4205 and $O^6$-(4-bromothenyl)guanine (B.4280). The $I_{50}$ values shown are extrapolated from the curves. Preincubation was for 1 hour after which [$^3$H]-methylated substrate was added to determine residual activity of ATase.

Figure 2A:
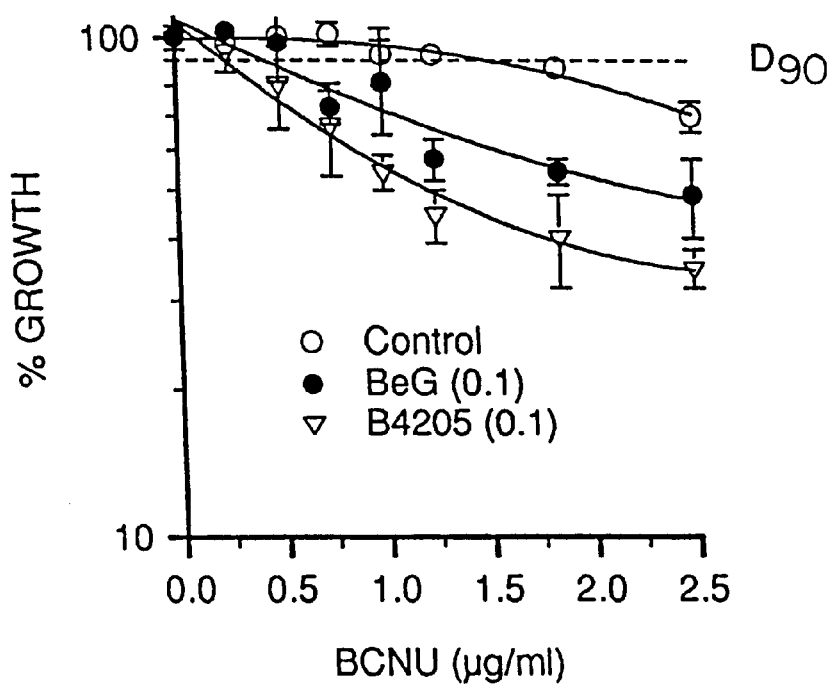
FIG. 2 is two graphs of percentage cell growth against alkylating agent concentration ($\mu$g/ml), showing the sensitization effect of $\underline{O}^6$-benzylguanine (BeG) and $\underline{O}^6$-thenylguanine (B.4205) at two different concentrations (0.1 and 1.0 $\mu$M) on sensitization of Raji cells to BCNU. The line at 90% growth is used for calculating $D_{90}$ values i.e. the dose of BCNU at which there was 90% growth as compared to untreated controls i.e. 10% growth inhibition.
Figure 2B:
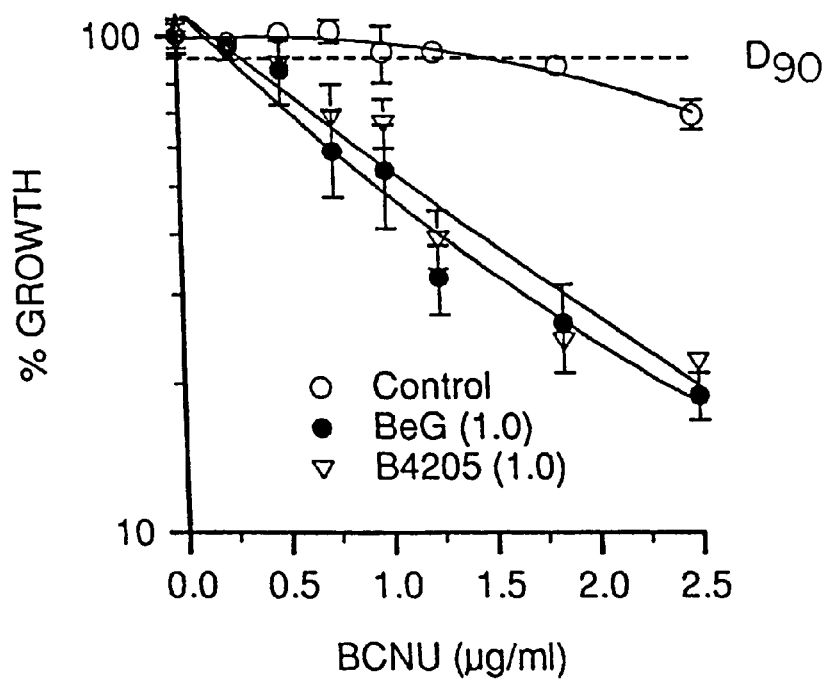

FIG. 16A is three graphs similar to FIG. 2 showing the effect of pretreatment with BeG and B.4280 (0.5 $\mu$M final concentration) on the sensitivity of Raji cells to the growth inhibitory effects of temozolomide. Inactivator or vehicle was given 2 hours prior to temozolomide.

Figure 16B:
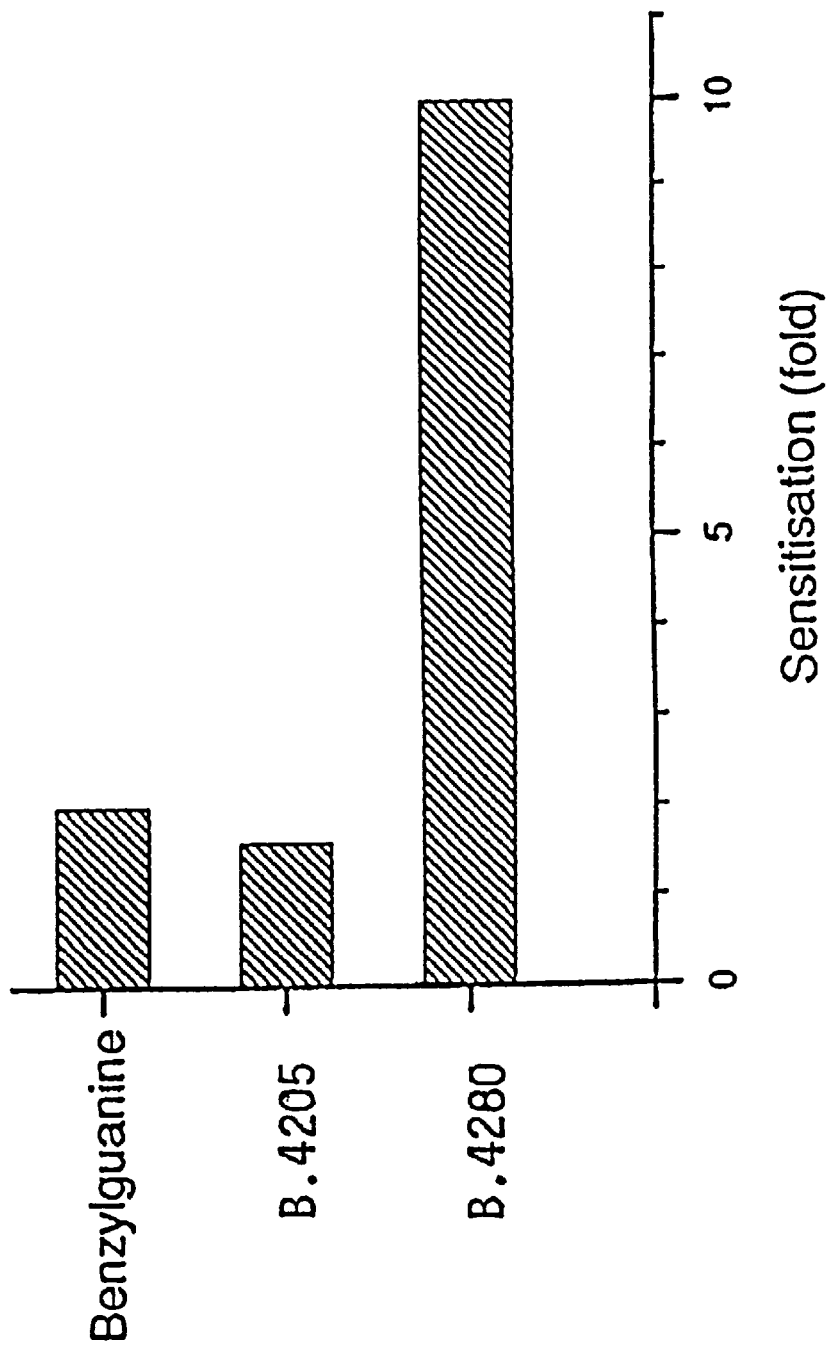

FIG. 16B is a diagram showing the relative sensitization of Raji cells to growth inhibition by the inactivators of FIG. 16A.

FIG. 17 is a diagram similar to FIG. 8 showing the effect of ATase inactivators BeG, B.4205 and B.4280 on ATase activity in human melanoma xenografts grown in nude mice. Animals were given a single dose of the inactivators intraperitoneally (i.p.) at 30 mg/kg or 60 mg/kg and sacrificed after the times shown.

FIG. 18 is six graphs showing the dose-dependence of ATase inactivation by B.4205 in several tissues of nude mice with a range of inactivator doses. Animals were given a single dose of B.4205 and sacrificed 2 hours later. The term "PATRIN" refers to the inactivator.

Figure 19:
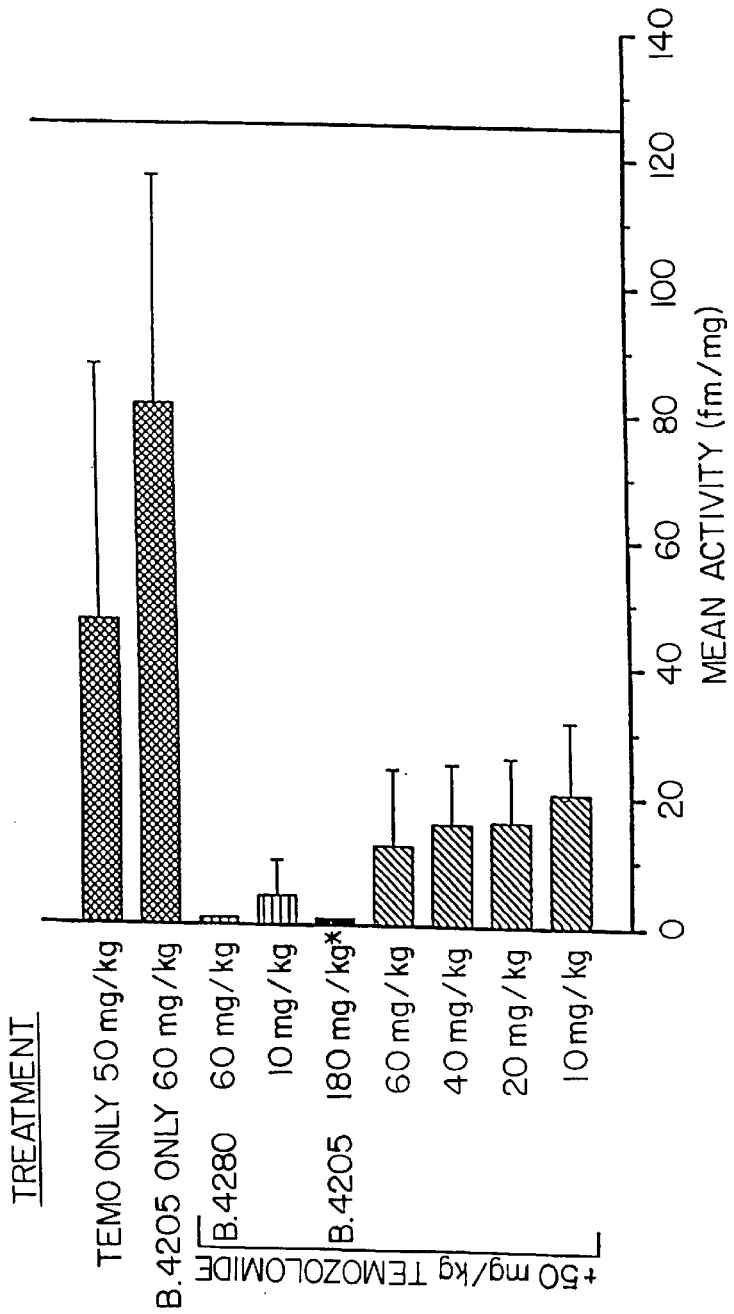

FIG. 19 shows the effect of ATase inactivators on ATase activity in human melanoma xenografts grown in nude mice. Animals were given 8.4205 or temozolomide alone or B.4205 or B.4280 in combination with temozolomide (50 mg/kg)i.p. at the doses shown on three consecutive days and sacrificed 24 hours after the final dose.

Figure 20:
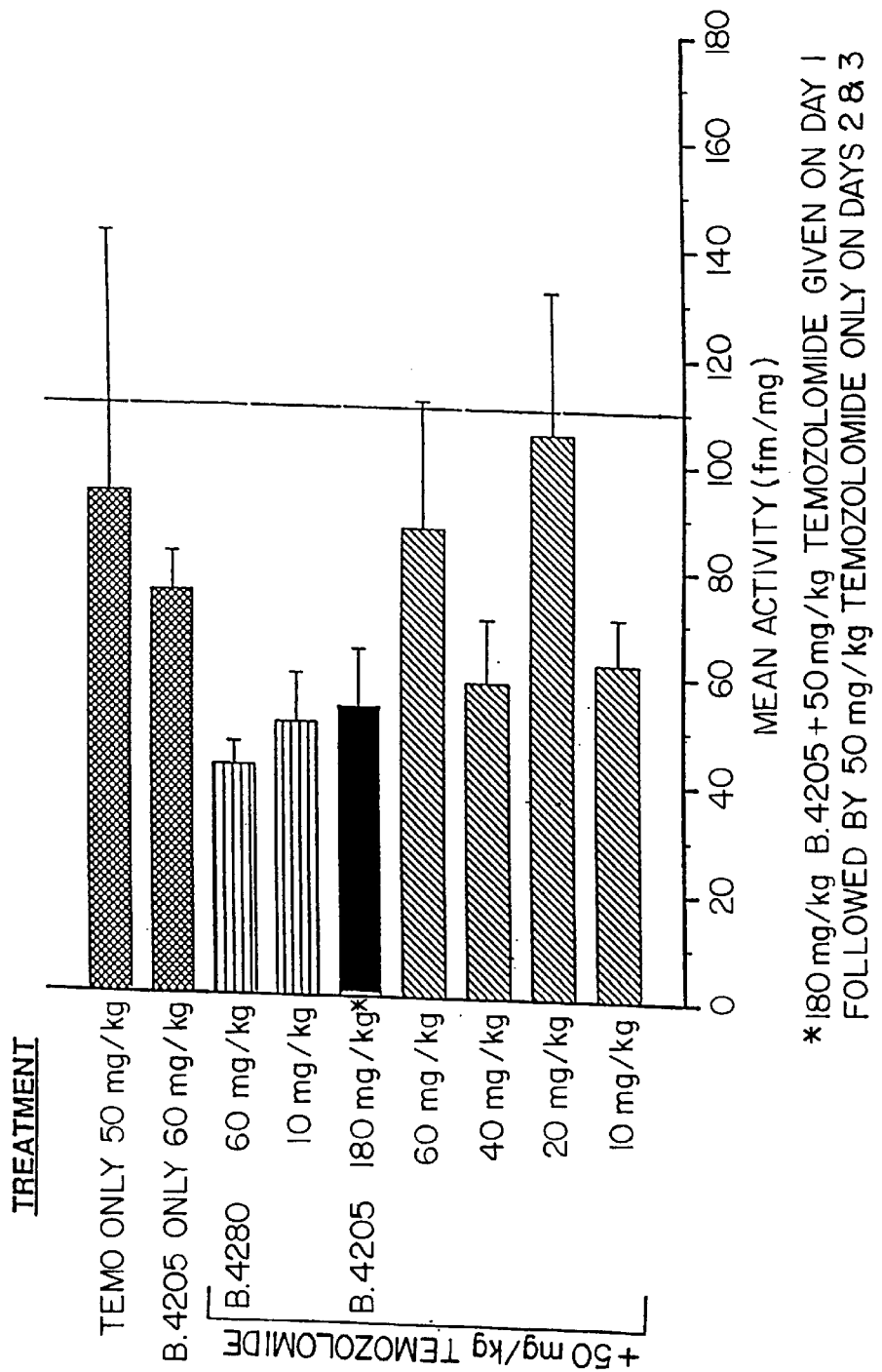

FIG. 20 is a diagram showing the effect of ATase inactivators on ATase activity in livers of nude mice. Animals were given the B.4205 or temozolomide alone or B.4205 or B.4280 in combination with temozolomide (59 mg/kg, i.p.) at the doses shown on three consecutive days and sacrificed 24 hours after the final dose.

Figure 21A:
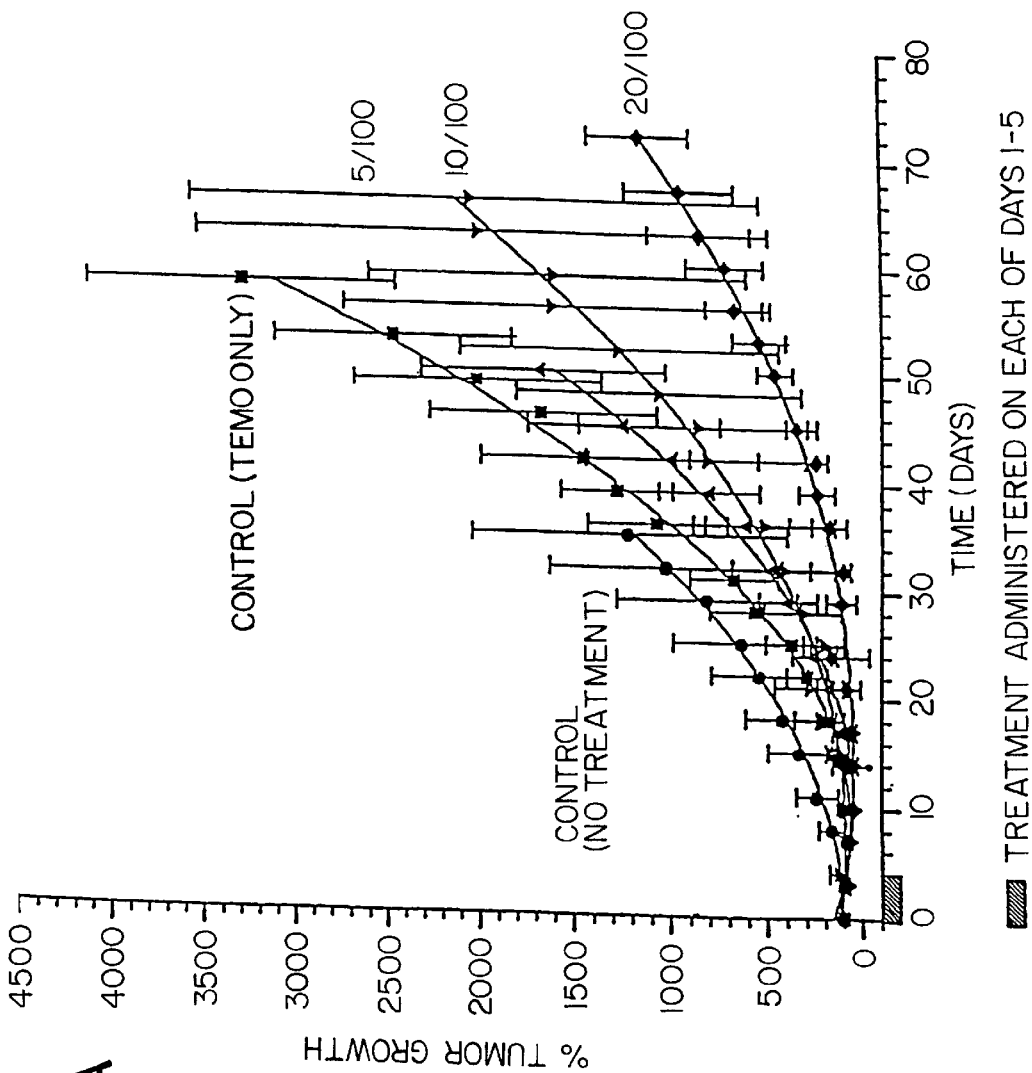

FIG. 21A is a graph showing the effect of B.4205 on the sensitivity of human melanoma xenografts to growth inhibition by temozolomide. Animals were untreated, given temozolomide alone (100 mg/kg, i.p.) or B.4205 (5, 10 or 20 mg/kg i.p.) followed 1 hour later by temozolomide (100 mg/kg, i.p.) on five consecutive days. Tumour growth was monitored as described. The data from a number of separate studies are presented.

FIG. 21B is a graph showing survival of animals used in the study shown in FIG. 21A. Groups of animals in which the xenografts had reached the maximum size were terminated.

FIG. 22A is a graph showing the effect of ATase inactivators on the sensitivity of human melanoma xenografts to growth inhibition by temozolomide. Animals were untreated, given temozolomide alone (100 mg/kg. i.p.) or B.4280 alone (20 mg/kg, i.p.) or B.4280 (1, 5, 10 or 20 mg/kg, i.p.) followed 1 hour later by temozolomide (100 mg/kg, i.p.) on five consecutive days. Tumour growth was monitored as described. The data from a number of separate studies are presented.

Figure 22B:
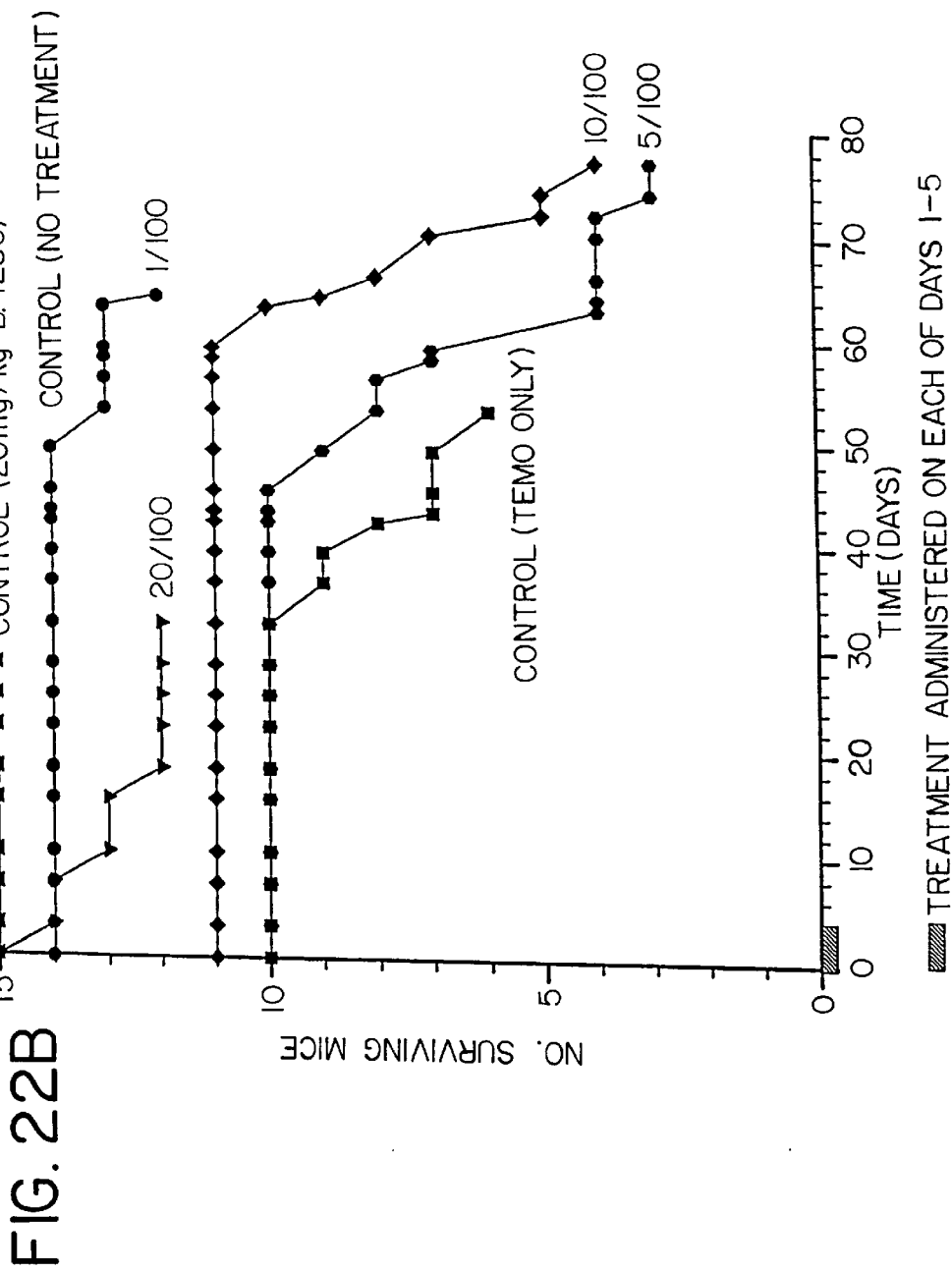

FIG. 22B is a graph showing the survival of the animals used in the study shown in FIG. 22A. Groups of animals in which the xenografts had reached the maximum size were terminated.

FIG. 23 is four graphs similar to FIG. 14 showing the effect of BeG or B.4205 on the sensitivity of human bone marrow granulocyte macrophage colony forming cells to toxic effects of temozolomide. BeG and B.4205 (10 $\mu$M final concentrations) were added to the culture medium 2 hours prior to temozolomide. Survival was determined as described.

FIG. 24A is a graph showing the comparison of the effect of B.4280 given i.p. and orally (p.o.) on the sensitivity of human melanoma xenografts to growth inhibition by temozolomide. Animals were untreated, given temozolomide alone (100 mg/kg) or B.4280 alone (20 mg/kg, i.p.) or B.4280 (20 mg/kg, i.p.) or B.4280 (30 mg/kg, p.o.) followed 1 hour later by temozolomide (100 mg/kg, i.p.) on five consecutive days. Tumour growth was monitored as described. The data from a number of separate studies are presented.

Figure 24B:
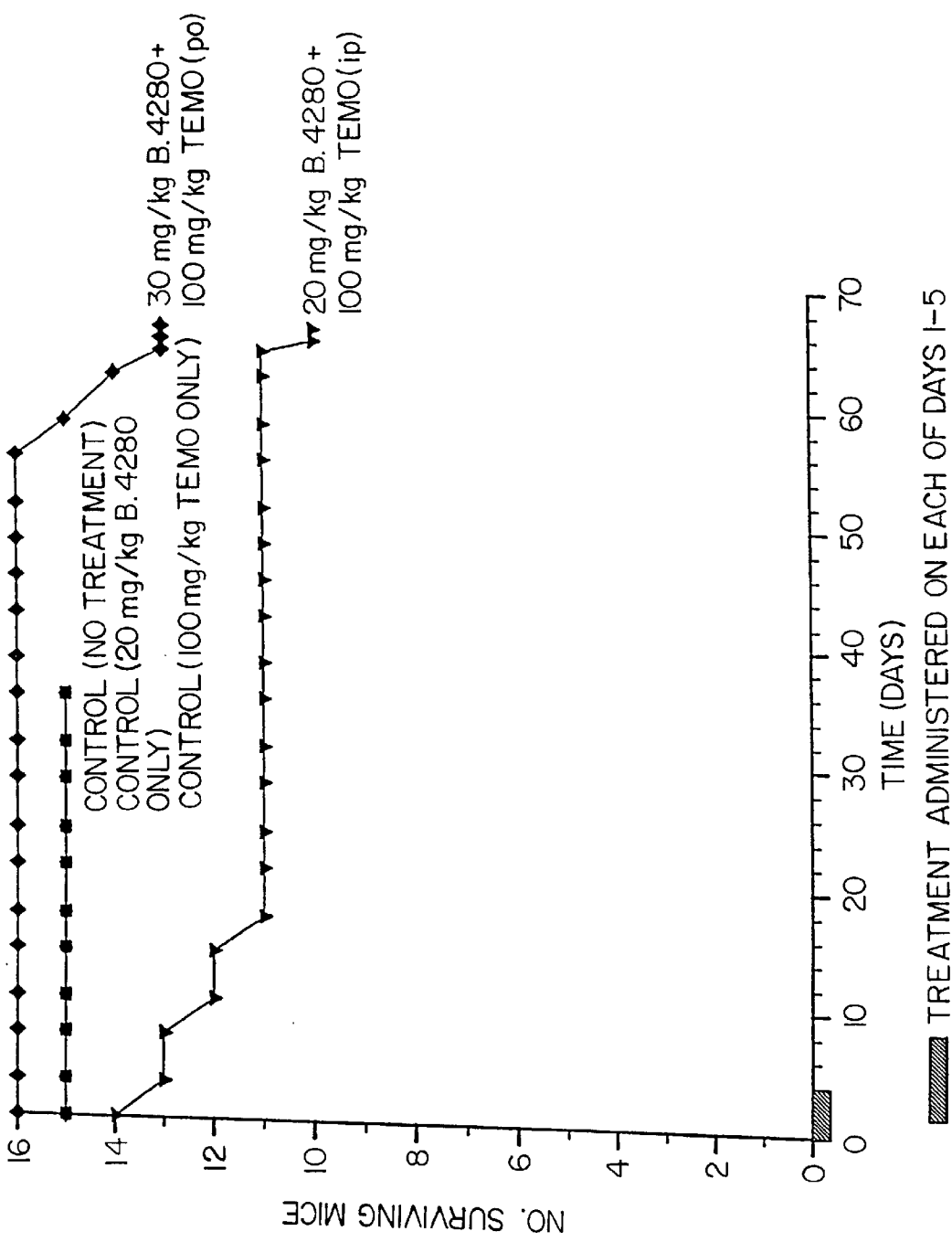

FIG. 24B is a graph showing the survival of the animals used in the study shown in FIG. 24A. Groups of animals in which the xenografts had reached the maximum size were terminated.

Figure 25:
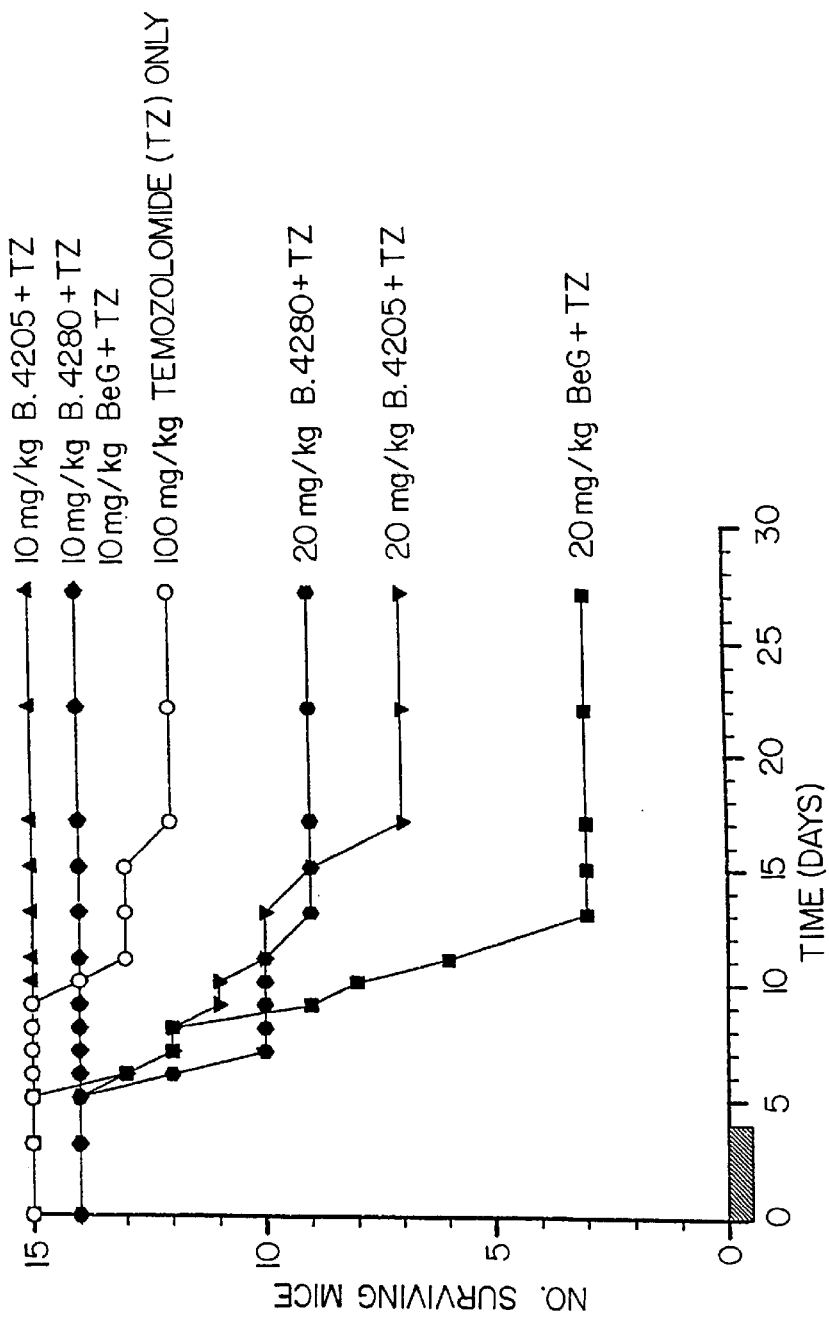

FIG. 25 is a graph showing the survival of animals in a comparative test of toxicity of BeG, B.4205 and B.4280 in combination with temozolomide (TZ) in non-tumour-bearing DBA, mice. Animals were given temozolomide alone (100 mg/kg i.p) or BeG (10 or 20 mg/kg i.p.), B.4205 (10 or 20 mg/kg i.p.) or B.4280 (10 or 20 mg/kg i.p.) followed one hour later by temozolomide (100 mg/kg i.p.) on four consecutive days. The vehicles were corn oil for the inactivators and PBS (20% DMSO) for temozolomide.

The term "pharmaceutically acceptable salts" as used in this specification and claims means salts of the kind known in the pharmaceutical industry including salts with inorganic acids such as sulfuric, hydrobromic, nitric, phosphoric or hydrochloric acid and salts with organic acids such as acetic, citric, maleic, fumaric, benzoic, succinic, larlaric, propionic, hexanoic, heptanoic, cyclopentanepropionic, glycolic, pyruvic, lactic, malonic, malic, o-(4-hydroxy-benzoyl) benzoic, cinnamic, mandelic, methanesulfonic, ethanesulfonic, 1,2-ethanedisulfonic, 2-hydroxyethanesulfonic, benzenesulfonic, p-chlorobenzenesulfonic 2-naphthalenesulfonic, p-toluenesulfonic, camphorsulfonic, 4-methyl-bicyclo[2.2.2]oct-2-ene-1-carboxylic, glucoheptonic, 4,4'-methylenebis(3-hydroxy-2-naphthoic), 3-phenylpropionic, trimethyl-acetic, tertiary butylacetic, lauryl sulfuric, gluconic, glutamic, hydroxynaphthoic, salicylic, stearic, or muconic, and the like.

In the specification the abbreviations "1 h" or "2 h" etc. mean "1 hour", "2 hours" etc.

MODES FOR CARRYING OUT THE INVENTION $O^6$hertarylakylguanine derivatives having ATase inactivating characteristics may be synthesized by adapting the standard preparation presented below as appropriate.

2-Amino-N,N,N-trimethyl 1H-purin-6-aminium chloride is prepared in accordance with the procedure described by Kiburis et. al., *J. Chem.Soc.* (C), 1971, 3942. Details of the conditions for reaction of this quaternary salt with sodium benzyloxide (to give $O^6$-benzyl-guanine) not disclosed in MacCoss, Chen and Tolman, *Tetrahedron Lett.*, 1985, 26, 1815, were given in MacCoss, Tolman, Wagner and Hannah, European Patent Application No. 184,473, but these were not suitable for preparation of relatively sensitive analogues, and the standard preparation below was devised by the inventors.

Standard Preparation of $O^6$-hetarylalkylguanines (Formula I, y=H)

Sodium hydride (60% in oil; 0.8 g, 20 mmol) is added to a solution of RR'CHOH (56 mmol, ca. 5 ml) in DMSO (5 ml) and the mixture is stirred at room temperature for 1 hour. For solid or higher molecular weight alcohols, up to 10 ml DMSO may be used instead of 5 ml. 2-Amino-N,N,N-trimethyl-1H-purin-6-aminium chloride (2.29 g, 10 mmol) is added and stirring is continued for a further 1 hour. The change in UV spectrum is then complete ($\lambda_{max}$ 312→284 nm) and the almost clear solution is treated with acetic acid (1.7 ml). After cooling and dilution with ether (300 ml), the mixture is set aside (2 hours) and the solid (A) collected. Trituration with water gives the product. A second fraction can be obtained by evaporation of the ether-DMSO filtrate and trituration of the residue successively with ether and water. Alternatively the product may be extracted from the solid (A) with warm acetonitrile. The recrystallised compounds show a single spot in TLC ($C_6H_6$-MeOH, 4:1) and are characterised by analysis and their NMR spectra. Frequently, they contain solvent of crystallisation. Melting points and analytical data are given in Table 2, UV and $^1$H NMR data in Table 3. NMR spectra were measured on a Bruker WP80 or MSL 300 instruments.

This standard preparation procedure (with variations indicated by symbols in Table 2) was used to make the compounds listed in Tables 2a and 3a. In compounds B.4217 and B.4219, R' is methyl; in the remaining compounds R' is H. $O^6$-benzylguanine and Compounds B4214, B4218 and B4231 listed in Table 4 below were also made by this standard preparation procedure for comparative testing purposes.

The variations indicated by the symbols in Table 2 are as follows:

a 5 mmol sodium hydride per mmol quaternary salt are used in preparation of this compound. When the standard amount (2 mmol) is used, 40% of the quaternary salt can be recovered in the reaction work-up.

b This compound is made by hydrolysis of the methyl ester B.4229 (145 mg, 0.5 mmol) in 2-methoxyethanol (2.5 ml) and water (2.5 ml) by treatment with 2M-NaOH (2.5 ml) for 4 hours at room temperature. Neutralisation with acetic acid (0.32 ml, 5.5 mmol), gentle evaporation, trituration with water (3 ml) and filtration give a solid which on extraction with hot methanol yields the acid B.4234.

c The required figures are based on the monohydrate of a mixture of 4 parts of sodium salt of the acid and 3 parts of the acid, requiring Na, 4.3%. Found: Na, 4.44%.

d 3 mmol alcohol $RCH_2OH$ per mmol quaternary salt are used instead of the standard 5.6 mmol.

e For alcohols which are too sensitive to sodium hydride in DMSO at room temperature, $RCH_2ONa$ is prepared in DMF (2.5 ml at −10° C.; 3 mmol $RCH_2OH$; 2 mmol sodium hydride). 1 mmol quaternary salt is added after 15–20 minutes and stirring continued for 2–3 hours at room temperature f Products are extracted with acetonitrile.

Preparation of Ribosides (formula I, Y=ribosyl)

A solution of alkoxide made as in the Standard Procedure above from sodium hydride (60% in oil; 120 mg, 3 mmol) and RR'CHOH (4.6 mmol) in dry DMSO (2 ml) during 1 hour is treated with 2-amino-6-chloropurine riboside (302 mg, 1 mmol) and stirred for 5 minutes at room temperature, then 15 minutes at 60–65° C. The reaction is then complete as indicated by the change in UV spectrum ($\lambda_{max}$ 311→284 nm). Cooling and thorough trituration with ether (100+15 ml) and filtration yield a solid which is treated with water (10 ml). The pH is brought from 11 to 8 by passing $CO_2$ briefly. Filtration removes inorganic material and the dried residue is extracted at room temperature with methanol (4×10 ml portions, each containing a drop of pyridine). Evaporation of almost all the methanol and addition of a little ether yield the product, almost pure by TLC ($C_6H_6$-MeOH 4:1). It is recrystrallised from methanol and a trace of pyridine, dissolving and concentrating below 40° C., sometimes with final addition of a little ether.

This procedure was used to make the compounds listed in Tables 2b and 3b. Traces of impurities are difficult to remove but NMR spectra show that the nucleosides are ca. 90% pure. Yields are of the order of 30–40%.

TABLE 2a

| Test No. | $O^6$-Substituent $RR^1CH-$ | Yield % (based on solvate) | Solvent for recrystn. | M.P. (decomp) (° C.) | Formula | | C | H | N |
|---|---|---|---|---|---|---|---|---|---|
| | | | | | | | \multicolumn{3}{c}{Analysis} |
| B.4203 | furfuryl | 85 | MeOH | Indeterminate: from 185 | $C_{10}H_9N_5O_2 \cdot 1/2H_2O$ | Found | 50.14 | 4.00 | 29.24 |
| | | | | | | Req. | 50.01 | 4.19 | 29.17 |
| B.4205 | thenyl | 72 | EtOH | Indeterminate gradual from 160 | $C_{10}H_9N_5OS \cdot 1/3EtOH$ | Found | 48.40 | 4.61 | 26.45 |
| | | | | | | Req. | 48.78 | 4.22 | 26.63 |
| B.4206 | 3-thienylmethyl | 74 | MeOH | 205 | $C_{10}H_9N_5OS \cdot MeOH$ | Found | 47.61 | 4.88 | 25.67 |
| | | | | | | Req. | 47.3 | 4.69 | 25.07 |
| B.4209 | 3-furylmethyl | 61 | EtOH | 191 | $C_{10}H_9N_5O_2$ | Found | 52.07 | 4.16 | 30.25 |
| | | | | | | Req. | 51.93 | 3.92 | 30.29 |
| B.4210 | 2-picolyl | 71 | MeOH | 220–221 | $C_{11}H_{10}N_6O \cdot 1/2H_2O$ | Found | 52.85 | 4.73 | 32.79 |
| | | | | | | Req. | 52.60 | 4.41 | 33.47 |
| B.4211 | 3-picolyl | 53 | MeOH | 226–228 | $C_{11}H_{10}N_6O \cdot 1/2H_2O$ | Found | 52.53 | 4.78 | 32.50 |
| | | | | | | Req. | 52.60 | 4.41 | 33.47 |
| B.4212 | piperonyl | 74 | EtOH | 195–197 | $C_{13}H_{11}N_5O_3 \cdot 3/4H_2O$ | Found | 52.22 | 4.48 | 23.64 |
| | | | | | | Req. | 52.25 | 4.22 | 23.44 |
| B.4213 | 2-naphthylmethyl | 74 | EtOH | 224–226 | $C_{16}H_{13}N_5O$ | Found | 65.91 | 4.58 | 23.99 |
| | | | | | | Req. | 65.97 | 4.50 | 24.05 |
| B.4217 | α-methylthenyl[f] | 27 | MeCN | 150 Upwards | $C_{11}H_{11}N_5OS$ | Found | 50.39 | 4.40 | 26.96 |
| | | | | | | Req. | 50.57 | 4.24 | 26.80 |
| B.4219 | 1-(3-thienyl)ethyl[f] | 57 | MeCN | 150 Upwards | $C_{11}H_{11}N_5OS$ | Found | 50.59 | 4.33 | 27.10 |
| B.4220 | 5-methylthenyl[f] | 29 | MeCN | 140 Upwards | $C_{11}H_{11}N_5OS$ | | | | |
| B.4221 | 5-methylfurfuryl[f] | 38 | MeCN | Indeterminate | $C_{11}H_{11}N_5O_2 \cdot 0.5H_2O$ | Found | 52.18 | 4.81 | 27.47 |
| | | | | | | Req. | 51.98 | 4.76 | 27.56 |
| B.4222 | 3-methylthenyl | 29 | MeOH | Indeterminate | $C_{11}H_{11}N_5OS$ | | | | |
| B.4226 | 2-benzo[b]thienyl-methyl | 66 | MeOH | 198–208 | $C_{14}H_{11}N_5OS \cdot MeOH$ | Found | 53.93 | 4.49 | 21.47 |
| | | | | | | Req. | 54.69 | 4.59 | 21.26 |
| B.4229 | 5-methoxycarbonyl-furfuryl[a,f] | 43 | MeOH | 120–130 (with effervescence) | $C_{12}N_{11}N_5O_4 \cdot 1.5H_2O$ | Found | 45.88 | 4.21 | 21.86 |
| | | | | | | Req. | 45.57 | 4.46 | 22.14 |
| B.4234 | 5-carboxyfurfuryl[b] | 67 | MeOH | 210–260 | $C_{11}H_9N_5O_4 \cdot H_2O$[c] | Found | 42.69 | 3.52 | 22.68 |
| | | | | | | Req. | 43.2 | 3.4 | 22.9 |
| B.4265 | 1-naphthylmethyl | 75 | MeOH | 210 Upwards | $C_{16}H_{13}N_5O \cdot 0.5MeOH$ | Found | 64.37 | 4.85 | 22.81 |
| | | | | | | Req. | 64.48 | 4.92 | 22.79 |
| B.4266 | 2-benzofuranyl-methyl | 58 | MeOH | 196–198 | $C_{14}H_{11}N_5O_2 \cdot MeOH$ | Found | 57.31 | 4.78 | 22.53 |
| | | | | | | Req. | 57.50 | 4.83 | 22.35 |
| B.4269 | 5-bromothenyl[d,e,f] | 14 | EtOH | 170–180 | $C_{10}H_8BrN_5OS$ | Found | 36.81 | 2.52 | 20.81 |
| | | | | | | Req. | 36.82 | 2.47 | 21.47 |
| B.4271 | 5-azapiperonyl[d] | 63 | EtOH | 230–240 | $C_{12}H_{10}N_6O_3 \cdot 0.25EtOH$ | Found | 50.27 | 3.86 | 27.94 |
| | | | | | | Req. | 50.40 | 3.89 | 28.22 |
| B.4273 | 5-cyanofurfuryl[d,f] | 15 | MeOH | 91–100 (with effervescence) | $C_{11}H_8N_6O_2 \cdot H_2O$ | Found | 48.25 | 3.70 | 29.82 |
| | | | | | | Req. | 48.19 | 3.67 | 30.65 |
| B.4274 | 5-oxazolylmethyl[d,f] | 32 | MeOH | 180–215 | $C_9H_8N_6O_2 \cdot 0.25H_2O$ | Found | 45.58 | 3.70 | 35.50 |
| | | | | | | Req. | 45.66 | 3.62 | 35.52 |
| B.4275 | 5-thiazolylmethyl[d,f] | 40 | MeOH | 190–220 | $C_9H_8N_6OS \cdot 0.5H_2O$ | Found | 42.14 | 3.73 | 32.43 |
| | | | | | | Req. | 42.02 | 3.53 | 32.67 |
| B.4277 | 4-picolyl[d] | 72 | MeOH | 230 Upwards | $C_{11}H_{10}N_6O$ | Found | 54.82 | 4.19 | 34.48 |
| | | | | | | Req. | 54.55 | 4.16 | 34.71 |
| B.4278 | 1-methyl-4-nitro-pyrrol-2-ylmethyl[d,e] | 22 | MeOH | 140–210 | $C_{11}H_{11}N_7O_3 \cdot 0.5H_2O$ | Found | 44.17 | 4.17 | 32.49 |
| | | | | | | Req. | 44.29 | 4.06 | 32.87 |

TABLE 2b

| Test No. Ribosides | $O^6$-Substituent $RR^1CH-$ | Yield % (based on solvate) | Solvent for recrystn. | M.P. (decomp) (° C.) | Formula | | C | H | N |
|---|---|---|---|---|---|---|---|---|---|
| B.4268 | piperonyl | | MeOH | from 150 (with effervescence) | $C_{18}H_{19}N_5O_7 \cdot 2H_2O$ | Found | 47.08 | 4.58 | 15.12 |
| | | | | | | Req. | 47.69 | 5.11 | 15.45 |
| B.4276 | 2-benzo[b]thienylmethyl | | MeOH-ether | 140–155 | $C_{19}H_{19}N_5O_5S \cdot H_2O$ | Found | 50.75 | 4.47 | 16.83 |
| | | | | | | Req. | 50.98 | 4.73 | 15.65 |
| B.4279 | thenyl | | MeOH-ether | from 120 (with effervescence) | $C_{15}H_{17}N_5O_5S \cdot 0.5H_2O$ | Found | 46.67 | 5.00 | 18.48 |
| | | | | | | Req. | 46.39 | 4.67 | 18.03 |

TABLE 3a

| Test No. | $O^6$-Substituent $RR^1CH—$ | $\lambda_{max}$(MeOH) (nm) | $\delta_H$ [ppm from TMS; $(CD_3)_2SO$], $J$ (Hz) |
|---|---|---|---|
| B.4230 | furfuryl | 243,285 | 5.43(s), 6.32(s), 6.49(dd, $J$ 3.1, 1.5), 6.66(d, $J$ 3.1), 7.71(d, $J$ 1.5), 7.81(s), 12.42(bs) |
| B.4205 | thenyl | 243,284 | 5.67(s), 6.30(s), 7.04(dd, $J$ 5.1, 3.5), 7.31(dd, $J$ 3.5, 1.2), 7.56(dd, $J$ 5.1, 1.2), 7.84(s), 12.47(bs) |
| B.4206 | 3-thienylmethyl | 242,284 | 5.47(s), 6.27(s), 7.26(dd, $J$ 4.8, 1.2), 7.54(dd, $J$ 4.8, 2.9), 7.62(s), 7.80(s), 12.40(bs) |
| B.4209 | 3-furylmethyl | 245,284 | 5.34(s), 6.26(s), 6.65(d, $J$ 1.4), 7.66(t, $J$ 1.4), 7.82(s), 7.83(bs), 12.41(bs) |
| B.4210 | 2-picolyl | 247,262 269sh,285 | 5.58(s), 6.27(s), 7.50(m), 7.84(s), 8.58(dd, $J$ 4.8, 1.2), 12.47(bs) |
| B.4211 | 3-picolyl | 245,263sh, 270sh,285 | 5.58(s), 6.36(s), 7.49(dd, $J$ 7.9, 4.8), 7.87(s), 8.01(dt, $J$ 7.9, 1.8), 8.62(dd, $J$ 4.8, 1.8), 8.80(bs), 12.48(bs) |
| B.4212 | piperonyl | 242,287 | 5.38(s), 6.02(s), 6.24(s), 6.95(m), 7.79(s), 12.37(bs) |
| B.4213 | 2-naphthylmethyl | 244,282 | 5.67(s), 6.28(bs), 7.46–8.04(m), 12.47(bs) |
| B.4217 | α-methylthenyl | 243,284 | 1.74(d, J 6.6), 6.24(s), 6.74(q, $J$ 6.6), 7.01(m), 7.24(m), 7.49(m), 7.81(s), 12.40(bs) |
| B.4219 | 1-(3-thienyl)ethyl | 242,283 | 1.67(d, $J$ 6.5), 6.20(s), 6.54(q, $J$ 6.5), 7.24(m) 7.50(m), 7.82(s), 12.37(bs) |
| B.4220 | 5-methylthenyl | 246,284 | 2.42(d, $J$ 3.4), 5.57(s), 6.25(s), 6.70(d, $J$ 3.4), 7.08(d), 7.81(s), 12.41(bs) |
| B.4221 | 5-methylfurfuryl | 240,283 | 2.28(s), 5.37(s), 6.11(m), 6.27(s), 6.53(d, $J$ 3.0), 7.81(s), 12.44(bs) |
| B.4222 | 3-methylthenyl | 244,283 | 2.28(s), 5.60(s), 6.25(s), 6.91(d, $J$ 5.0), 7.45(d, $J$ 5.0), 7.80(s), 12.44(bs) |
| B.4226 | 2-benzo[b]thienylmethyl | 240,267,282 ($RCH_2OH$: 241, 262,289w,300w) | 5.78(s), 6.38(s), 7.38(m), 7.60(s), 7.83(s), 7.85(m), 12.47(bs) |
| B.4229 | 5-methoxycarbonyl-furfuryl | 251,280sh ($RCH_2OH$: 259) | 3.82(s), 5.50(s), 6.39(s), 6.87(d, $J$ 3.4), 7.32(d, $J$ 3.4), 7.83(s), 12.45(bs) |
| B.4234 | 5-carboxylfurfuryl | 250,280 ($RCH_2OH$: 256) | 5.43(s), 6.35(s), 6.68(d, $J$ 3.3), 6.87(d, $J$ 3.3), 7.85(s), 12.53(bs) |
| B.4265 | 1-naphthylmethyl | 244,283,293 sh | 5.96(s), 6.36(s), 7.58(m), 7.72(d, $J$ 6.8) 7.79(s) 7.89(m), 8.11(m), 12.44(bs) |
| B.4266 | 2-benzofuranyl-methyl | 246,278,284 ($RCH_2OH$: 246,275w,283w) | 5.62(s), 6.40(s), 7.13(s), 7.27(dt, $J$ 7.3, 1.1), 7.34(dt, $J$ 7.3, 1.3), 7.65(m), 7.68(m), 7.85(s), 12.48(bs) |
| B.4269 | 5-bromothenyl | 247,284 $RCH_2OH$: 246 | 5.62(s), 6.36(s), 7.17(ABq, $J$ 3.7) 7.85(s), 12.47(bs) |
| B.4271 | 5-azapiperonyl | 241,290 ($RCH_2OH$; 234,294) | 5.40(s), 6.18(s), 6.39(s), 7.48(d, $J$ 1.8), 7.83(s), 12.46(bs) |
| B.4273 | 5-cyanofurfuryl | 248,286 ($RCH_2OH$: 248) | 5.53(s), 6.42(s), 6.99(d, $J$ 3.5), 7.67(d, $J$ 3.5) 7.87(s), 12.52(bs) |
| B.4274 | 5-oxazolylmethyl | 243,286 | 5.56(s), 6.38(s), 7.44(s), 7.85(s), 8.45(s), 12.48(bs) |
| B.4275 | 5-thiazolylmethyl | 244,286 | 5.76(s), 6.42(s), 7.85(s), 8.14(s), 9.13(s), 12.49(bs) |
| B.4277 | 4-picolyl | 244,265sh,286 | 5.58(s), 6.34(s), 7.47(d, $J$ 5.7), 7.88(s), 8.60(d, $J$ 5.7), 12.51(bs) |
| B.4278 | 1-methyl-4-nitro-pyrrol-2-ylmethyl | 244,285,320sh ($RCH_2OH$: 280,320) | 3.78(s), 5.46(s), 6.40(s), 6.98(s), 7.84(s), 8.08(s), 12.49(bs) |

TABLE 3b

| Test No. | $O^6$-Substituent | $\lambda_{max}$(MeOH) (nm) | $\delta_H$ [ppm from TMS; $(CD_3)_2SO$], $J$ (Hz) |
|---|---|---|---|
| Ribosides | | | |
| B.4268 | piperonyl | 246,287 ($RCH_2OH$ 240,288) | 3.53 and 3.62(2 × dd, $J$ 11.9, 3.75), 3.89(q, $J$ 3.5), 4.10(dd, $J$ 4.9, 3.5), 4.45(t, $J$ 5.5), 5.1(bs), 5.38(s), 5.78(d, $J$ 6.0), 6.02(s), 6.51(s), 6.93(d, $J$ 7.7), 7.00(dd, $J$ 7.7, 1.5), 7.10(d, $J$ 1.5), 8.10(s) |
| B.4276 | 2-benzo[b]thienylmethyl | 241,252, 269,287 ($RCH_2OH$ 241,262 289w, 300w) | 3.57 and 3.67(2 × m), 3.91(q, $J$ 3.6), 4.12(q, $J$ 5.2), 5.16(m), 5.45(d, $J$ 6.2), 5.83(s + m), 6.61(s), 7.40(m), 7.63(s), 7.88(m), 7.97(m), 8.16(s) |
| B.4279 | thenyl | 246,285 | 3.57 and 3.64(2 × m), 3.92(q, $J$ 3.5), 4.13(m), 4.49(q, $J$ 5.2), 5.16(m), 5.45(m), 5.70(s), 5.81(d, $J$ 6.0), 6.57(s), 7.07(dd, $J$ 5.1, 3.5), 7.34(d, $J$ 0.9), 7.60(d, $J$ 1.3), 8.14(s), 12.40(bs) |

The starting alcohols RR'CHOH were usually made by reduction of the corresponding aldehydes, often commercially available, by sodium borohydride. A different approach was used for the precursors of the ester B.4229 and the nitrile B.4273. Sucrose was converted [1] via 5-chloromethylfurfural into 5-hydroxymethylfurfural. Oxidation[2] of this aldehyde gave the carboxylic acid which was esterfied by the method of Bocchi et al.[3] to methyl 5-(hydroxymethyl)furoate,[4] required for B.4229. The oxime [5] of the aldehyde was dehydrated by the method of Carotti et al.[6]; the crude reaction product was treated with conc. aqueous ammonia in methanol before extraction into dichloromethane. Distillation afforded 5-cyanofurfuryl alcohol,[7] required for B.4273.

For B.4266, Vilsmeier reaction[8] of benzofuran yielded the 2-aldehyde, reduced to the required alcohol,[9] while for B.4226 lithiation and treatment with dimethylformamide gave the 2-aldehyde and in turn the alcohol.[10]

For B.4274, dimethyl tartrate was oxidised[11] to methyl glyoxylate which reacted [12] with tosylmethyl isocyanide to give methyl oxazole-5-carboxylate.[13] This was reduced by lithium aluminium hydride by the method of Fallab[14] to the alcohol.[15]

For B.4275, bromomalonaldehyde[16] and thiourea yielded 2-aminothiazole-5-carboxaldehyde.[17] Deamination by amyl nitrite[17] followed by sodium borohydride reduction gave 5-hydroxymethylthiazole[14].

For B.4271, 5-azapiperonyl alcohol (m.p. 82–84° C.; found, C, 54.60; H, 4.58; N, 9.09; $C_7H_7NO_3$ requires C, 54.90; H,4.61; N, 9.15%) was prepared from the corresponding aldehyde.[18]

For B.4278, 1-methylpyrrole-2-carboxaldehyde was nitrated[19] and reduced to the alcohol [20] by sodium borohydride.

By way of specific example, the preparation of $O^6$-thenylguanine (B.4205) will now be described:

Preparation of $O^6$-thenylguanine

A solution of thenyl alcohol (3.18 ml, 33.6 mmol) in DMSO (3 ml) was treated with sodium hydride (60% in oil; 0.48 g, 12 mmol), stirring cautiously at first. After 1 hour 2-amino-N,N,N-trimethyl-1H-purin-6-aminium chloride (1.37 g, 6 mmol) was added and stirring continued 1 hour more. Acetic acid (1.0 ml) was added, cooling briefly, and the mixture diluted with ether (180 ml). The solid (2.09 g) was collected after 1–2 h. Evaporation of ether from the filtrate and distillation of DMSO and excess thenyl alcohol (b.p. 48–57° C./0.2 mm) left a residue which on trituration with ether yielded a second solid fraction (0.36 g). The combined solids were rubbed (trituration) with water (6 ml), yielding product (1.335 g, 90%) showing a strong spot in TLC ($C_6H_6$-MeOH, 4:1) with only traces of impurity. Dissolution in hot ethanol (30 ml), clarification by filtration through Celite, and concentration (to 10 ml) using a rotary evaporator yielded B.4205 (1.125 g, 71% of material containing ⅓ EtOH per mole as solvate).

Compounds of formula I in which Y is R"XCHR"' (seco-nucleosides) may be prepared by an analogous preparation to the reaction of $O^6$-benzylguanine with α-chloro-ethers (MacCoss et al., *Tetrahedron Lett.*; European Patent Application No. 184,473., loc. cit.) or with alkyl bromides (e.g. Kjellberg, Liljenberg and Johansson, *Tetrahedron Lett.*, 1986, 27, 877; Moschel, McDougall, Dolan, Stine, and Pegg, *J.Med. Chem.*, 1992, 35, 4486).

Typical "sugar" components corresponding to R"XCHR"', leading to seco-nucleosides, are made by methods described in e.g. McCormick and McElhinney, *J. Chem. Soc., Perkin Trans.* 1, 1985, 93; Lucey, McCormick and McElhinney, *J. Chem. Soc. Perkin Trans.* 1, 1990, 795.

Compounds of formula I in which Y is ribosyl or deoxyribosyl (nucleosides) may be prepared by methods analogous to the syntheses of $O^6$-benzylguanine riboside and 2-deoxyriboside (Moschel et al. 1992; cf. Gao, Fathi, Gaffney et al., *J. Org. Chem.*, 1992, 57, 6954; Moschel, Hudgins and Dipple, *J. Amer. Chem. Soc.*, 1981, 103, 5489) (see preparation of Ribosides above).

Industrial Applicability

The amount of the compound of the present invention to be used varies according to the effective amount required for treating tumour cells. A suitable dosage is that which will result in a concentration of the compound of the invention in the tumor cells to be treated which results in the depletion of ATase activity, e.g. about 1–2000 mg/kg body weight, and preferably 1–800 mg/kg body weight, particularly 1–120 mg/kg body weight, prior to chemotherapy with an alkylating agent. The pharmaceutical composition of the invention may be formulated in conventional forms with conventional excipients, as described for example in U.S. Pat. Nos. 5,091,430 and 5,352,669, the contents of which are incorporated herein by reference in their entirety. The composition may contain the inactivator according to the invention together with an alkylating agent; or the composition may comprise two parts, one containing the inactivator and the other containing the alkylating agent. The method of administering the compounds of the invention to a host may also be a conventional method, as described in U.S. Pat. Nos. 5,091,430 and 5,352,669 for example. For administration of an inactivator according to the invention to patients, the pharmaceutical composition may suitably contain the inactivator in a suitable vehicle such as 40% polyethyleneglycol 400 in saline solution, or in saline or 3% ethanol (in saline), for intravenous injection, or in a powder form in suitable capsules for oral administration. Alkylating agents may be administered in accordance with known techniques and in conventional forms of administration, as described in U.S. Pat. Nos. 5,091,430 and 5,352,669 for example or preferably as a single dose immediately after or up to 24 hours after but preferably around 2 hours after administration of the ATase inactivating agents and also at doses lower than those used in standard treatment regimen. A reduction in dose may be necessary because the inactivators would generally he anticipated to increase the toxicity of the alkylating agents. Examples of chloroethylating agents include 1,3 bis (2-chloroethyl)-1-nitrosourea (BCNU), 1-(2-chloroethyl)-3-cyclohexyl-1-nitrosourea (CCNU), fotemustine, mitozolomide and clomesone and those described in McCormick, McElhinney, McMurry and Maxwell *J. Chem. Soc. Perkin Trans.* 1, 1991, 877 and Bibby, Double, McCormick, McElhinney, Radacic, Pratesi and Dumont *Anti-Cancer Drug Design*, 1993, 8, 115. Examples of methylating agents include temozolomide U.S. Pat. No. 5,260,291 the contents of which are incorporated herein in their entirety) and dacarbazine, procarbazine, and streptozocin.

METHODS

Purification of Recombinant ATases

The cDNA cloning and overexpression of the human ATase has been reported previously[23]. Purification of the recombinant proteins was achieved either by affinity chromatography through a DNA-cellulose column as described by Wilkinson et al.,[25, 26] or by DEAE-cellulose ion-exchange chromatography. For the latter, the ATase protein was partially purified by ammonium sulphate precipitation (30–60%) and dialysed against 10 mM Tris-HCl pH 7.5, 1 mM DTT, 2 mM EDTA, 10% glycerol, before loading on a DEAE-cellulose column. The ATase was then eluted with a 0–0.1 M NaCl gradient. The purified human ATase protein retained activity for more than one year when stored at high concentration at −20° C. in buffer I [50 mM-Tris/HCl (pH 8.3)/3 mM-dithiothreitol/1 mM-EDTA] and could be thawed and refrozen several times without substantial loss of activity.

Incubation with Inactivators and ATase Assay

Compounds to be tested were dissolved in DMSO to a final concentration of 10 mM and diluted just before use in buffer I containing 1 mg/ml bovine serum albumin (IBSA). Recombinant ATase was diluted in IBSA and titrated in order that the reaction be conducted under ATase, and not substrate, limiting conditions. In each assay, fixed amounts of ATase (60–75 fmol) were incubated with varying amounts of $O^6$-benzylguanine, or test compound in a total volume of 200 μl of IBSA containing 10 μg of calf thymus DNA at 37° C. for 1 hour. The [$^3$H]-methylated-DNA substrate (100 μl containing 6.7 μg of DNA and 100 fmol of $O^6$-methylguanine) was added and incubation continued at 37° for 1 hour, until the reaction was completed. Following acid hydrolysis of the DNA as previously described[21] the [$^3$H]-methylated protein was recovered and quantitated by liquid scintillation counting. Samples were typically assayed in duplicate and experiments repeated several times. $I_{50}$ is the concentration of inactivator required to produce a 50% reduction in ATase activity.

Cell Culture and Preparation of Extracts

Mammalian cells were cultured under standard conditions. For example, Raji (a human lymphoblastoid cell line from a Burkitt's lymphoma) cells were grown in suspension culture in RPMI medium supplemented with 10% horse serum. A375M cells are human melanoma cells from which the xenografts described below were established following subcutaneous injection into nude mice: WiDr cells are a human colon carcinoma cell line: Hamster+120 cells are a mitozolomide-selected subline of a Chinese hamster lung fibroblast V79 cell line called RJKO: Yoshida cells are a rat carcinosarcoma cell line and $YR_{bus}$ is a busulphan resistant subline thereof: XP cells are an SV40-transformed fibroblast cell line originally from the skin of a *Xeroderma piamentosum* patient, pHMGhAT2b cells are a clone of these cells that have been transfected with a mammalian cell expression vector containing the human ATase cDNA and pHMG1a cells are a clone that have been transfected with the expression vector only (i.e. one not containing the human ATase cDNA). Cell pellets were resuspended in cold (4° C.) buffer I containing 2 $\mu$g/ml leupeptin and sonicated for 10 seconds at 12$\mu$ peak to peak distance. After cooling in ice, the cells were sonicated for a further 10 seconds at 18$\mu$. Immediately after sonication, 0.01 volumes of 8.7 mg/ml phenylmethanesulphonylfluoride in ethanol was added and the sonicates centrifuged at 15000 g for 10 minutes at 4° C. to pellet cell debris. The supernatant was kept for determination of ATase activity (see below).

Stability of Inactivators at 37° C.

Inactivators (10 mM in DMSO) were diluted to 0.1 mM in prewarmed degassed buffer I (1 mM EDTA, 50 mM Tris pH 8.3) or PBS (pH 7–7.2). PBS (Phosphate buffered saline) is 0.8% NaCl, 0.02% KCl, 0.15% $Na_2H_2PO_4$, 0.02% $KH_2PO_4$, pH 7.2. Samples were immediately transferred to a CARY13 spectrophotometer (cuvette block held at 37° C.) and scanned at an appropriate wavelength (according to the spectral properties of the compound) at 3–10 minute intervals for up to 80 hours. The results were expressed as percentage absorbance change versus time and T½ values (half life) extrapolated from this.

Inactivation of ATase activity in mammalian cells.

Cells were diluted to $10^6$/ml in culture medium containing either the appropriate concentration of inactivator or an equivalent volume of vehicle (DMSO). Following incubation at 37° C. for 2 hours the cells were harvested by centrifugation, washed twice with PBS and the resulting cell pellets (between 1–2×10 per pellet) stored at −20° C. ATase activity was determined as described above, in duplicate sonicated cell extracts and expressed as the, percentage activity remaining based on that present in the untreated controls (for example 350–450 fm/mg in Raji cells). $I_{50}$ (i.e concentration of inactivator required to reduce ATase activity by 50%) values were extrapolated from this data.

Sensitization of Raji and A375M Cells to BCNU and Temozolomide.

Sensitization of Raji cells to the cytotoxic effects of BCNU and temozolomide following a 2 hour pretreatment with inactivator was analysed using an XTT assay[22]. Briefly, cells were plated at 1000 cells/well in 96 well plates and incubated at 37° C. for 30 minutes prior to the addition of medium containing either the appropriate concentration of inactivator or an equivalent volume of vehicle. Following a 2 hour incubation at 37° C., medium containing either increasing doses of BCNU, temozolomide or equivalent vehicle was added and the cells allowed to grow for 6 days. At this time XTT solution was added and the cells incubated for a further 4 hours at 37° C. The resulting red/orange formazan reaction product was quantified by measuring absorption at 450 nm on a microtitre platereader.

Sensitization of A375M cells to the cytotoxic effects of BCNU was analysed by MTT assay [24] differing from the XTT assay described above as follows. A375M cells (1000 per well) were allowed to grow for 24 hours then treated with the inactivator and 2 hours later with BCNU. After 6 days MTT solution (4 mg/ml) was added and cells incubated for 3 hours at 37° C. Medium was aspirated and the resulting purple formazan crystals were solubilised in DMSO (120 $\mu$l) and cell viability was quantified by measuring absorption at 540 nm using a microtitre plate reader.

From this data the percentage growth of cells relative to that in control wells was determined for a range of BCNU or temozolomide doses in both the presence and absence of inactivator. Raji sensitization to BCNU ($D_{90}.^C/D_{90}.^I$) was determined by dividing the $D_{90}$ (i.e. dose at which there was 90% growth versus untreated controls i.e. 10% growth inhibition) calculated for data on use of BCNU alone ($D_{90}.^C$) by that for BCNU plus inactivator ($D_{90}.^I$). A value of one (1) thus indicates no sensitization by the inactivator. Raji sensitization to temozolomide and A375M sensitization to BCNU were determined using the corresponding $D_{50}$ values (i.e. the doses at which there was 50% growth inhibition).

Sensitivity of Mammalian Cells to the Inactivators or their Hydrolysis Products

In order to assess the effects on cell growth alone, *Xeroderma pigmentosum* cells and Chinese Hamster V79 cells were exposed to increasing concentrations (up to 600 $\mu$M) of selected inactivators for 2 h at 37°. In some cases, the inactivators were allowed to undergo hydrolysis at 37° C. for 20 hours and then added to Raji cells in order to assess the extent to which the decomposition products of the agents might inhibit cell growth. After 6 days the extent of cell growth was determined as described above.

Sensitization of Bone Marrow Cells to Temozolomide (GM-CFC assay)

For the granulocyte/macrophage colony-forming cell (GM-CFC) assay primary human bone marrow samples were obtained from patients undergoing cardiothoracic surgery. Following removal of erythrocytes from the samples, cells were plated out at $1-2 \times 10^5$/ml in 300 mOsM Iscoves medium containing 10 $\mu$M inactivator or equivalent volume of DMSO, 20% foetal calf serum, 10% 5637 conditioned medium as a source of growth factors and 0.3% agar noble, in 1 ml petri dishes containing appropriate dose of temozolomide and incubated at 37° C. in an atmosphere of 5% $CO_2$ and 95% air. After 9 days, colonies comprising of more than 50 cells were counted. The colonies represented precursor cells of the granulocyte/macrophage lineage (huGM-CFC). Survival was expressed as a % of the number of colonies at zero dose temozolomide.

Xenograft Studies

Animals

BALB-C derived athymic male mice (nu/nu athymic) weighing between 25–35 g were obtained from the in-house breeding colony of the Paterson Institute for Cancer Research, Christie Hospital NHS Trust, Wilmslow Road, Manchester M20 9BX, England (ASU mice). The animals were housed in a sterile environment until required for experiments. In one experiment mice were obtained from Harlan-Olac, Harlan UK Limited, Shaw's Farm, Blackthorn, Bicester, Oxon. OX6 OPT, England (OLAC mice). These mice weighed between 17–23 g and were subsequently found to be more sensitive to the toxic effects of the combination (inactivator and BCNU) treatment. For this reason lower doses were administered.

Cells

A375M (human melanoma) cells were grown in DMEM containing 10% fetal bovine serum. The cells were prepared for in vivo inoculation by incubation with 0.01% trypsin.

Tumours

Cells ($10^6$) in 100 μl of PBS were injected subcutaneously into the right-hand flank of 8–10 week old nu/nu athymic mice. These cells were allowed to develop into a tumour for 3–4 weeks for passaging into experimental animals. Tumour blocks measuring 2 mm×2 mm×2 mm were implanted subcutaneously on the right hand flank. These animals were ready for use in inactivator experiments in 7–10 days.

Drug Treatment

Nu/Nu mice were treated with either 30 or 60 mg/kg $O^6$-benzylguanine, or B.4205 and the appropriate vehicle control (i.p), 60–90 minutes prior to 10–25 mg/kg BCNU (i.p.). $O^6$-benzylguanine and B.4205 were prepared as a 5 mg/kg solution in corn oil and BCNU (2 mg/ml) in PBS+3% ethanol.

Tumour Measurements

Xenograft tumour measurements were taken every 1–2 days by workers using digital calipers. Tumour volume was calculated using the formula $(h \times w \times l)\pi/6$. The experimental animals were also weighed every 1–2 days. Measurements continued until tumours in the control animals reached the maximum allowable volume (i.e. 1 cm×1 cm×1 cm).

RESULTS

Tables 4, 5 and 6 shows the physical, biochemical and in vivo data for each of the inactivators. The tests listed are explained in the Methods section.

TABLE 4

| INACTIVATOR | M. Wt | $I_{50}(\mu M)$ | T½(h) in Buffer I | Raji $I_{50}$ (μM) | T½(h) in PBS | Raji sensitization ($D_{90} \cdot C/D_{90} \cdot I$) 0.1 μM | 0.5 μM | 1.0 μM |
|---|---|---|---|---|---|---|---|---|
| $O^6$-benzylguanine | 241 | 0.04 | >64 | 0.10 | >16 | *1.9 ± 0.7 | *2.0 ± 0.4 | *3.8 ± 1.8 |
| $O^6$-allylguanine | 191 | 22 | >64 | | | | | |
| B4203 | 240 | 0.08 | 0.3 | 0.04 | 0.17 | 2.6 | | 5.7 |
| $O^6$-furfurylguanine.½H₂O | | | | | | | | |
| B.4205 | 262 | 0.018 | 1.2 | 0.02 | 0.6 | 8.4 | | 8.0 |
| $O^6$-thenylguanine.⅓EtOH | | | | | | | | |
| B.4206 | 279 | 0.03 | >80 | 0.06 | >16 | 1.6 | | 6.0 |
| $O^6$-3-thienylmethylguanine.1MeOH | | | | | | | | |
| B.4209 | 231 | 0.15 | | 0.15 | >16 | 1.5 | 1.4 | 2.8 |
| $O^6$-3-furylmethylguanine | | | | | | | | |
| B.4210 | 251 | 35 | | >1.0 | >16 | | | |
| $O^6$-2-picolylguanine.½H₂O | | | | | | | | |
| B.4211 | 251 | 0.43 | | | >16 | | | |
| $O^6$-3-picolylguanine.½H₂O | | | | | | | | |
| B.4212 | 299 | 0.02 | 1.3 | 0.05 | 0.72 | 2.7 | | 10.7 |
| $O^6$-piperonylguanine.¾H₂O | | | | | | | | |
| B.4213 | 291 | 0.15 | | 0.03 | >16 | 1.2 | 2.1 | 2.9 |
| $O^6$-(2-naphthylmethyl)guanine | | | | | | | | |
| B.4214 | 255 | >60 | | | | | | |
| DL-$O^6$-(α-methylbenzyl)guanine | | | | | | | | |
| B.4217 | 261 | >500 | | | | | | |
| DL-$O^6$-(α-methylthenyl)guanine | | | | | | | | |
| B.4218 | 255 | 58 | | | | | | |
| $O^6$-(2-methylbenzyl)guanine | | | | | | | | |
| B.4219 | 261 | 85 | | >1.0 | 0.12 | 1.0 | 1.0 | 1.0 |
| DL-$O^6$-[1-(3-thienyl)ethyl]guanine | | | | | | | | |
| B.4220 | 261 | 9 | | >1.0 | >16 | 1.0 | 1.0 | 1.0 |
| $O^6$-(5-methylthenyl)guanine | | | | | | | | |
| B.4221 | 254 | 10 | | >1.0 | >16 | 1.0 | 1.0 | 1.0 |
| $O^6$-(5-methylfurfuryl)guanine.½H₂O | | | | | | | | |
| B.4222 | 260 | 0.65 | | 0.47 | >16 | 1.4 | 1.9 | 2.1 |
| $O^6$-(3-methylthenyl)guanine | | | | | | | | |
| B.4226 | 329 | 0.03 | 9.7 | 0.06 | 6.7 | 1.6 | 1.6 | 10.0 |
| $O^6$-(2-benzo[b]thienylmethyl)guanine.1 MeOH | | | | | | | | |
| B.4229 | 316 | 0.09 | | 0.25 | >16 | 1.2 | 2.1 | 2.5 |
| $O^6$-(5-methoxycarbonylfurfuryl)guanine.⅛H₂O | | | | | | | | |
| B.4231 | 280 | 60 | | | | | | |
| $O^6$-(2-methoxybenzyl)guanine.½H₂O | | | | | | | | |
| B.4234 | 306 | 60 | | >1.0 | >16 | 1.0 | 1.0 | 1.0 |
| $O^6$-(5-carboxyfurfuryl)guanine | | | | | | | | |
| B.4265 | 307 | 95 | 60 | | | | | |
| $O^6$-1-(naphthylmethyl)guanine.½MeOH | | | | | | | | |
| B.4266 | 313 | 0.035 | | | >16 | | | |
| $O^6$-(2-benzofuranylmethyl)guanine.1MeOH | | | | | | | | |
| B.4268 | 453 | 0.75 | | | 8 | | | |
| $O^6$-piperonylguanosine.2H₂O | | | | | | | | |
| B.4269 | 326 | 0.0045 | | 0.006 | | | | |
| $O^6$-(5-bromothenyl)guanine | | | | | | | | |

TABLE 4-continued

| INACTIVATOR | M. Wt | $I_{50}(\mu M)$ | T½(h) in Buffer I | Raji $I_{50}$ ($\mu M$) | T½(h) in PBS | Raji sensitization ($D_{90} \cdot C/D_{90} \cdot I$) 0.1 $\mu M$ | 0.5 $\mu M$ | 1.0 $\mu M$ |
|---|---|---|---|---|---|---|---|---|
| B.4271 $O^6$-(-5-azapiperonyl)guanine.¼EtOH | 298 | 0.23 | | >16 | | | | |
| B.4273 $O^6$-(5-cyanofurfuryl)guanine.H$_2$O | 256 | 0.006 | | | | | | |
| B.4274 $O^6$-(5-oxazolylmethyl)guanine.¼H$_2$O | 274 | 0.34 | | | | | | |
| B.4275 $O^6$-(5-thiazolylmethyl)guanine.½H$_2$O | 257 | 0.033 | | | | | | |
| B.4276 $O^6$-(2-benzo[b]thienylmethyl) guanosine.H$_2$O | 464 | 0.35 | | | | | | |
| B.4277 $O^6$-4-picolylguanine | 242 | 0.13 | | | | | | |
| B.4278 $O^6$-(1-methyl-4-nitro-pyrrol-2-ylmethyl)guanine | 298 | 0.55 | | | | | | |
| B.4279 $O^6$-thenylguanosine.½H$_2$O | 388 | 0.9 | | | | | | |

*Mean of 8 individual experiments

TABLE 5

Inactivation of ATase in Mammalian Cells $I_{50}(\mu M)$

| | CELL LINE | | | | |
|---|---|---|---|---|---|
| INACTIVATOR | Hamster + 120 | Rat Yoshida | Human XP | Human Raji | Human WiDr |
| $O^6$-benzylguanine | 0.20 | 0.14 | 0.07 | 0.10 | >0.09 |
| B.4203 | 0.12 | 0.06 | 0.06 | 0.04 | 0.08 |
| B.4205 | 0.03 | 0.02 | 0.03 | 0.02 | 0.02 |

TABLE 6

| | A375M sensitization ($D_{50} \cdot C/D_{50} \cdot I$) | | |
|---|---|---|---|
| INACTIVATOR | 0.5 $\mu M$ | 1.0 $\mu M$ | 5.0 $\mu M$ |
| $O^6$-benzylguanine | 3.1 | 2.3 | 4.2 |
| $O^6$-allylguanine | 1.3 | | 1.9 |
| B.4203 | 2.0 | | 2.5 |
| B.4205 | 2.8 | 2.3 | 3.5 |
| B.4206 | 3.3 | | 4.6 |
| B.4209 | | 2.5 | |
| B.4210 | | 1.5 | |
| B.4212 | 2.3 | | 2.5 |
| B.4213 | | 2.0 | |
| B.4220 | | 1.3 | |
| B.4221 | | 1.0 | |
| B.4222 | | 1.4 | |
| B.4226 | 3.8 | | 4.5 |
| B.4229 | | 1.8 | |
| B.4234 | | 0.8 | |
| B.4266 | 6.3 | | 6.3 |

FIG. 1 shows the result of the in vitro ATase inactivation assay using 4 of the compounds. B.4206 was somewhat more effective than BeG but B.4212 and B.4205 were considerably better under the assay conditions used. B.4203 was not as effective as BeG.

FIG. 2 shows that at 0.1 $\mu M$ inactivator, B.4205 was more effective than BeG in sensitizing Raji cells to the growth inhibitory effects of BCNU: at 1.0 $\mu M$ inactivator, B.4205 and BeG were equally effective in this respect.

Figure 4:
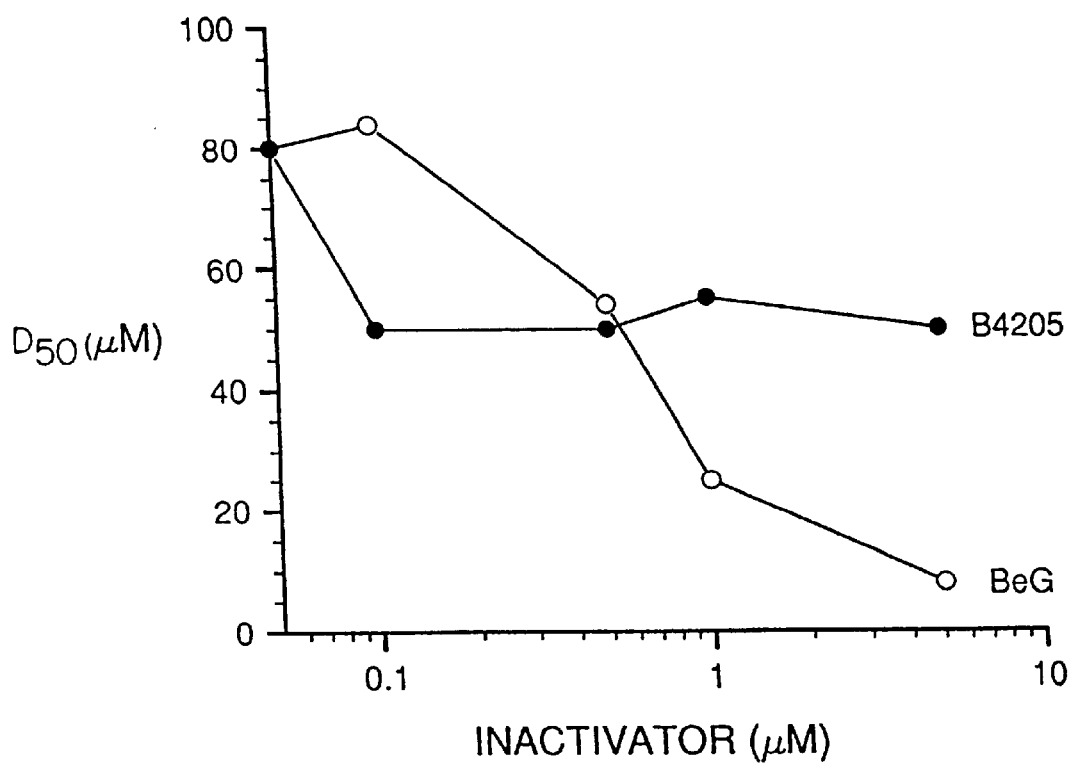
FIG. 4 is a graph extrapolated from FIG. 3 of values for $D_{50}$ ($\mu$M) (i.e. the dose of temozolomide at which there was 50% growth as compared to untreated controls) against inactivator concentration ($\mu$M).

FIG. 3 shows that at 0.1 $\mu M$ inactivator, B.4205 was more effective than BeG in sensitising Raji cells to the growth inhibitory effects of temozolomide but that as the doses of the inactivators were increased, sensitization by BeG became more effective whilst that by B.4205 remained the same. This lack of dose response with B.4205 but clear dose response with BeG is shown more clearly in FIG. 4.

Figure 5A:
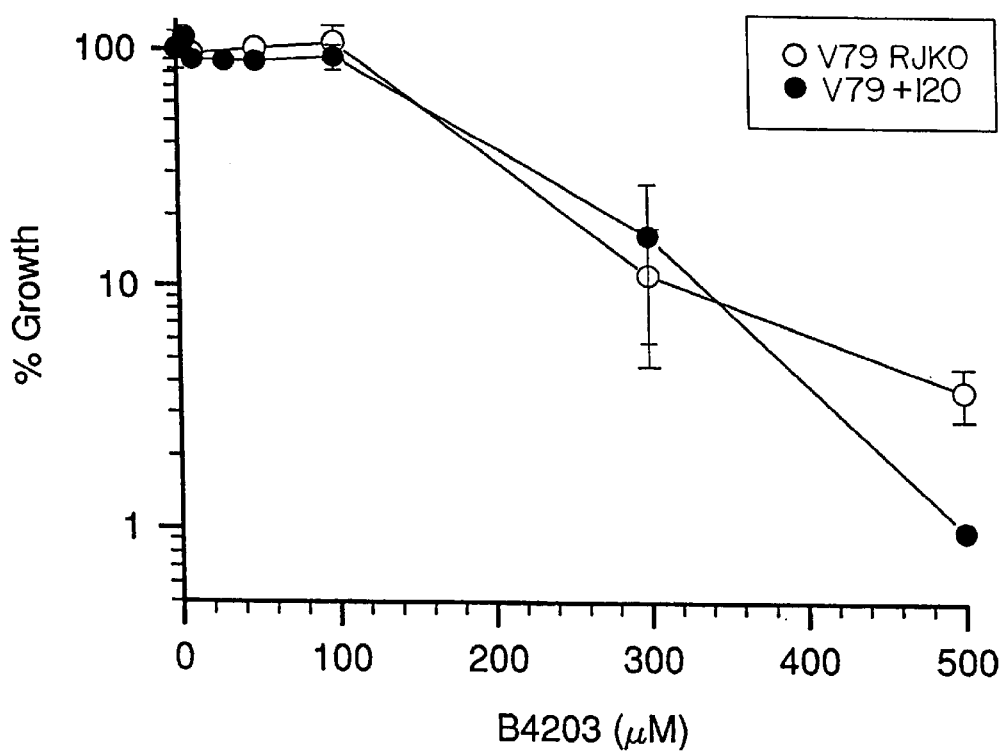
FIG. 5 is two graphs of percentage cell growth against inactivator concentration, showing the growth inhibiting effect of $\underline{O}^6$-furfurylguanine (B.4203) and B.4205 on Chinese hamster V79 cells(RJKO) and a subline thereof (+120).
Figure 5B:
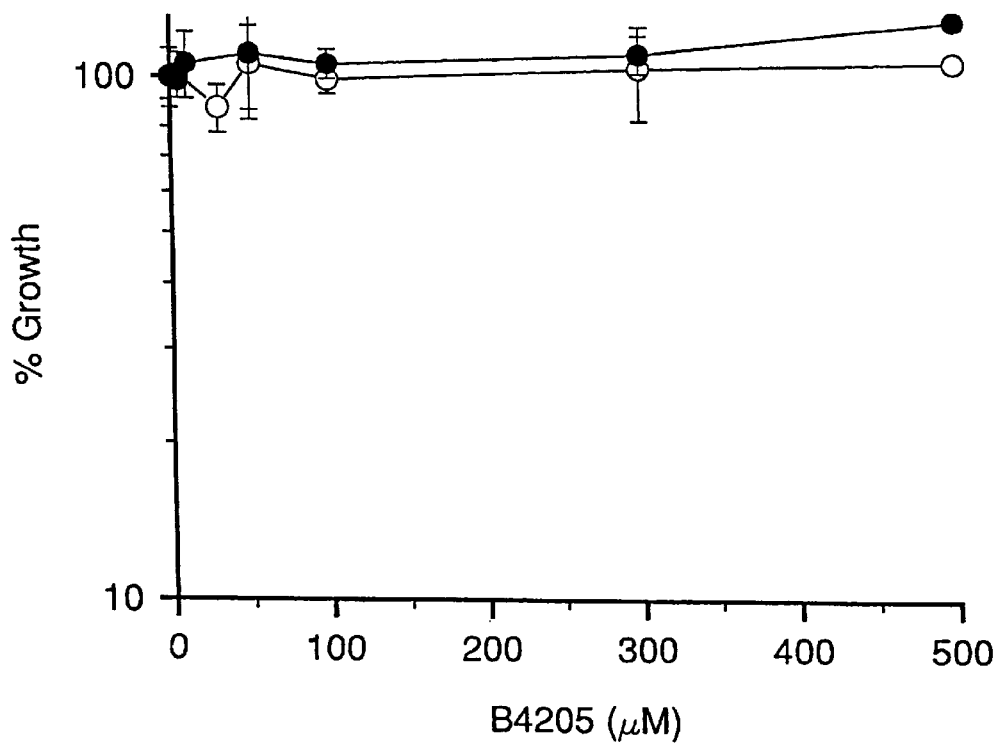

FIG. 5 shows that whilst some growth inhibition of B79 cells was produced by B.4203 at doses in excess of 100 uM (i.e. at least 100× higher than the $I_{50}$ dose for this compound), no such effects were seen with B.4205 up to the maximum concentration used.

Figure 6A:
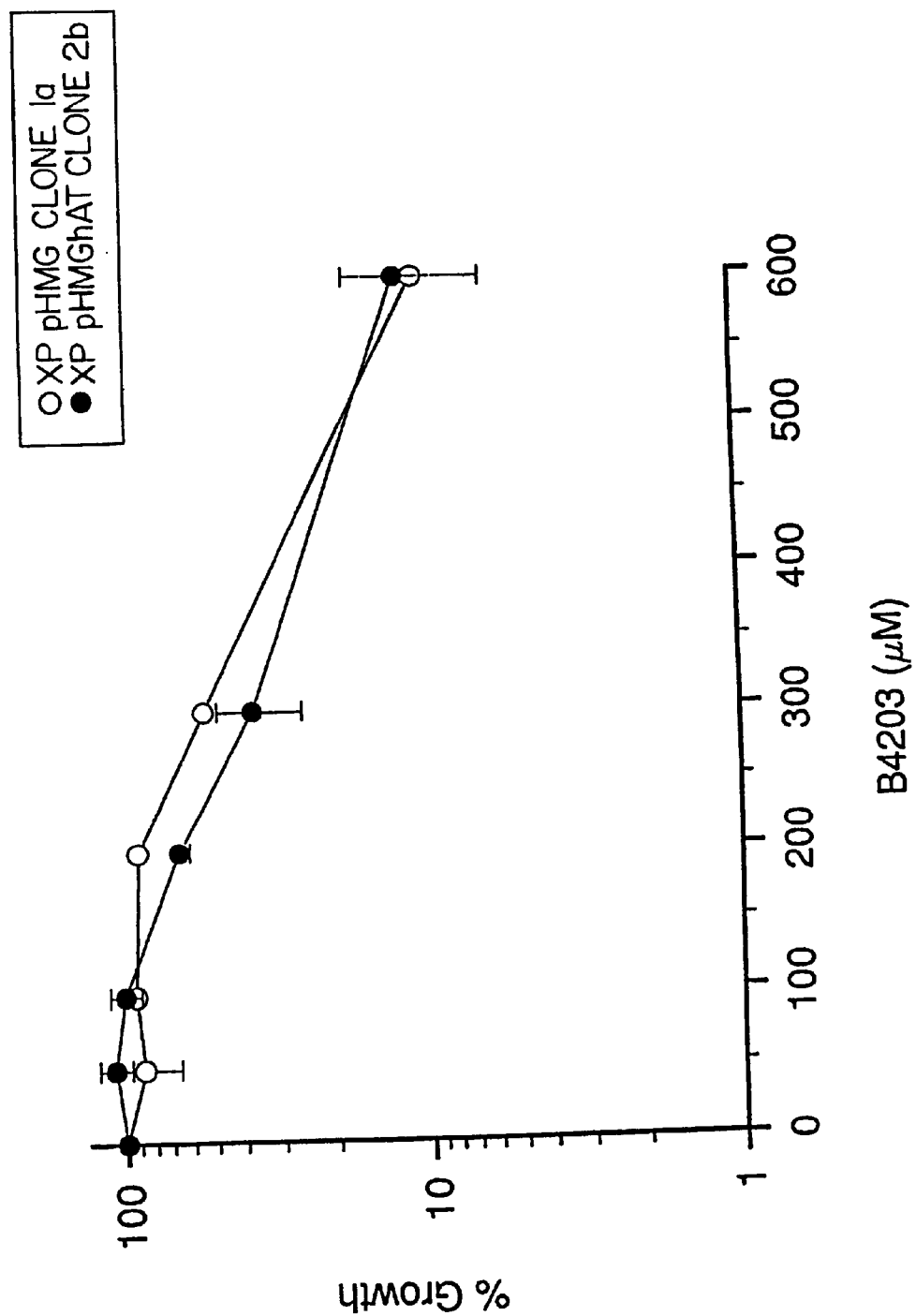
FIG. 6 is two graphs of percentage cell growth against inactivator concentration, showing the growth inhibition effect of B.4203 and B.4205 on two *Xeroderma pigmentosum* subclones.
Figure 7B:
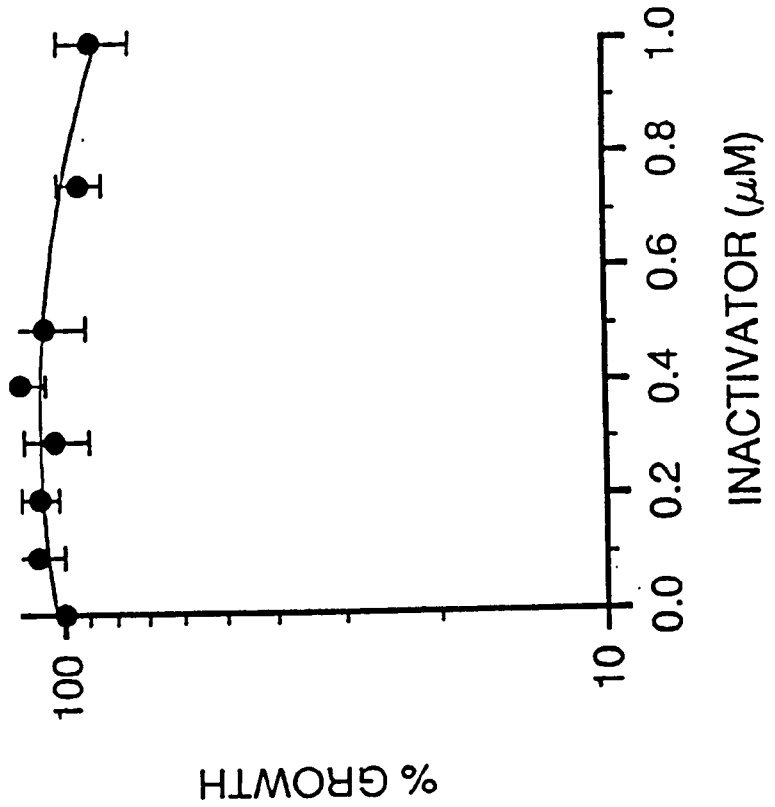
FIG. 7 is four graphs of percentage cell growth against inactivator concentration ($\mu$M) showing the effect of degradation products of inactivators B.4203, B.4205, B.4212 ($O^6$-piperonylguanine) and B.4226 ($O^6$-[2-benzo(b)thienylmethyl)guanine) on Raji cell growth.
Figure 7A:
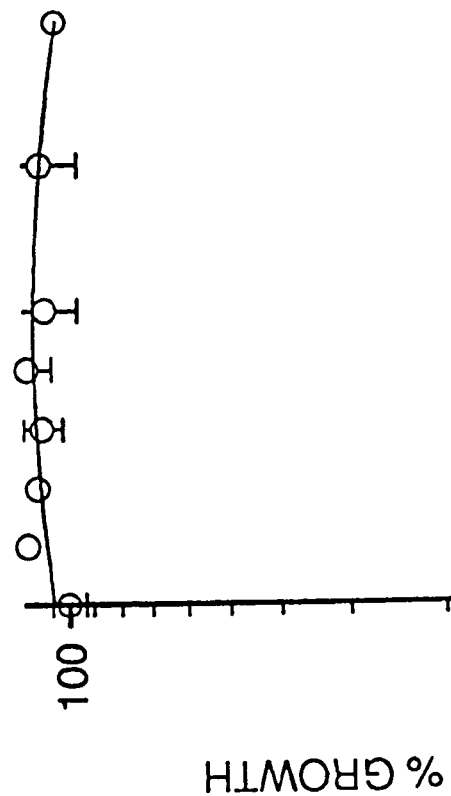
Figure 7D:
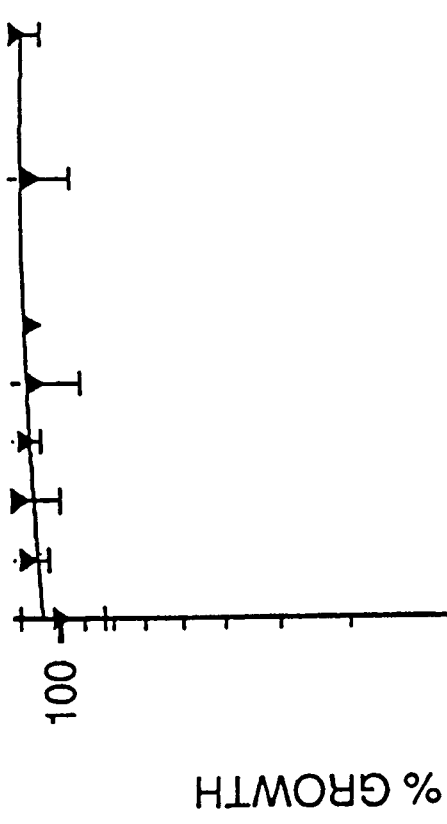
Figure 7C:
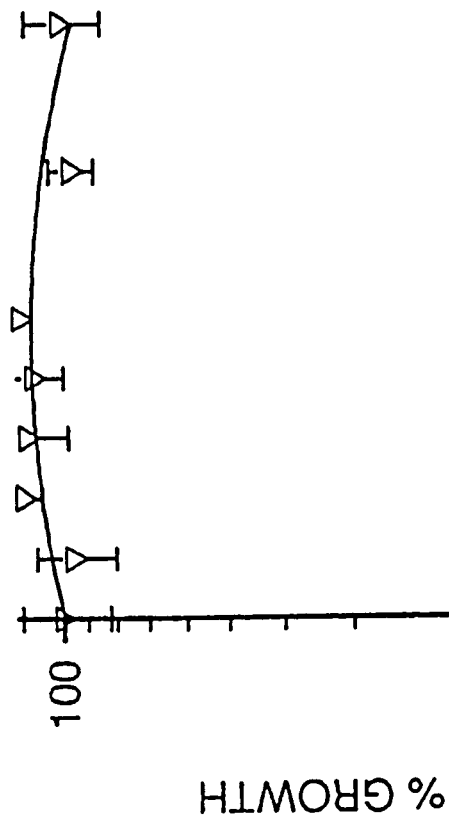

FIG. 6 shows that XP cells were as susceptible to the growth inhibitory effects of B.4203 but that these cells were more sensitive than V79 cells to the effects of B.4205. However, the doses required for growth inhibition were at least 100 times that required for ATase inactivation. It can be concluded that the inherent growth inhibitory effects of these inactivators would not contribute detectably to the sensitization of cells to the growth inhibitory effects of the alkylating agents.

FIG. 7 shows that no substantial growth inhibitory effects were produced in Raji cells when the given compounds were allowed to undergo hydrolysis (see Methods) before being added to the cells without further addition of alkylating agents. Under these experimental conditions therefore, the decomposition products of the agents would not be expected to contribute to the growth inhibitions seen using combinations of these agents and alkylating agents.

FIGS. 8–13 shows the results of the xenograft study in greater detail. The depletion and recovery of ATase activity following exposure to $O^6$-benzylguanine or B.4205 was measured in A375 tumour xenograft (FIG. 8) extracts prepared from tissues of animals sacrificed 2 or 24 hours after administration of inactivator. FIGS. 9–13 indicate the sensitization of A375 tumour xenografts in nude mice to either $O^6$-benzylguanine or B.4205 in combination with BCNU as described in the Methods section. In each Figure the top graph shows the percentage increase in tumour volume over the time course of the experiment. The lower graph shows the number of animals in each treatment group and the number surviving following treatment. The graphs show that B.4205 is comparable to $O^6$-benzylguanine (BeG) in reducing tumour volume and is substantially less toxic in combination with BCNU than BeG in combination with BCNU. In human patients, cutaneous malignant melanoma is treated with BCNU, particularly in the USA (Balch, C. M., Houghton, A. & Peters, L. (1989) "Cutaneous Melanoma" in *Cancer: Principles and Practise of Oncology*, De Vita, V. T., Helman, S. & Rosenberg, S. A. (eds), pp1499–1542, Lipincott: Philadelphia) so that the human melanoma xenograft grown in nude mice is an animal model system that is clinically highly relevant.

FIG. 14 shows the results of the tests on sensitization of human bone marrow cells to temozolomide as described in the Methods section above. The bone marrow cells were obtained from three patients identified as C, D and E respectively. The survival curves shown relate to the cytotoxic effect of combined inactivator/temozolomide treatment. It is desirable that this effect should be reduced. The results for patients C & E show that B.4205 had a smaller sensitization effect than $O^6$-benzylguanine ($O^6$BeG); for patient D there was no differential but this result is regarded as a reasonable variation in scientific testing with human material.

Table 7 shows the toxic effect of inactivator alone on bone marrow cells obtained from 5 patients A–E, including the same patients C–E as in FIG. 17. The results for B.4205 are comparable to those for $O^6$-benzylguanine. Note that the cells of patient B were almost twice as sensitive to both BeG and B.4205 in comparison to the other samples.

TABLE 7

INACTIVATOR (10 μM) TOXICITY IN BONE MARROW CELLS

| Patient | Date of Experiment | No. of colonies as % of control (ie no inactivator) | |
|---|---|---|---|
| | | $O^6$-benzylguanine | B.4205 |
| A | 05/02/93 | 95 | 91 |
| B | 25/03/93 | 46 | 46 |
| C | 17/05/93 | 88 | 97 |
| D | 05/05/93 | 88 | 118 |
| E | 05/05/93 | 89 | 89 |

SUMMARY OF FINDINGS

1) All of the compounds have been tested for their ability to inactivate recombinant human ATase under standard conditions in an in vitro assay. Under these conditions two of the compounds (B.4214 and B.4217) did not inactivate ATase up to the highest concentration used but these were compounds in which R' is methyl. The remainder of the compounds inactivated ATase with $I_{50}$ values ranging from 0.0045 to 95 μmolar. Eight compounds (B.4205, B.4206, B.4212, B.4226, B.4266, B.4269, B.4273, B.4275) had $I_{50}$ values lower than that of BeG (Table 4).
2) The inactivators underwent hydrolysis in aqueous solution at different rates (half lives 0.17 to >80 hours) but this was not related to their efficiency as ATase inactivators. (Table 4)
3) Compounds that were efficient in the inactivation of ATase in vitro ($I_{50}$<1.0 μM) also inactivated ATase in human cells with $I_{50}$ values that were generally only slightly (mean approx. 1.5 times) higher than those found using recombinant protein in the in vitro assay. (Table 4)
4) B.4205 inactivated ATase in human, rat and Chinese hamster cells with similar effectiveness ($I_{50}$ values 0.02–0.03). For B.4203 the range was 0.04–0.12. In the cell lines used B.4205 and B.4203 were up to 7 times more effective than BeG. (Table 5)
5) B.4203 and B.4205 were toxic to the XP cells studied and B.4203 was toxic to the V79 cells studied but only at concentrations that were at least 100 times higher than those at which sensitization to BCNU was observed. (FIGS. 5 & 6)
6) Compounds that were efficient in the inactivation of ATase in vitro ($I_{50}$<1.0 μM) and in Raji cells ($I_{50}$<1.0 μM) also sensitized Raji and A375M cells to the growth inhibitory effects of BCNU where this was tested. (Table 4)
7) At inactivator concentrations of 0.1 μM, B.4205 was more effective than BeG in sensitising Raji cells to the growth inhibitory effects of temozolomide. (FIG. 3)
8) The in vitro assay can be used to predict which compounds are most likely to be effective sensitisers of mammalian cells to the growth inhibitory effects of BCNU and related cytotoxic agents (see Moschel et al., *J. Med. Chem.*, 35, 4486–4491, 1992; Chae et al., *J. Med. Chem.*, 37, 342–347, 1994).
9) B.4295 was similar or slightly more effective than BeG in sensitising human melanoma xenografts grown in nude mice to the growth inhibitory effects of BCNU.(FIGS. 9–13)
10) B.4205 was as effetive as BeG in inactivating ATase in human melanoma xenografts grown in nude mice.(FIG. 8)
11) The in vitro assay and/or the xenograft ATase depletion assay may be used to predict which compounds are most likely to be effective sensitisers of melanoma xenografts to the growth inhibitory effects of BCNU and related cytotoxic agents (see Dolan et al. *Cancer Commun.* 2, 371–377, 1990; Friedman et al. *Cancer Res.* 55, 2853–2857, 1995).
12) In contrast to BeG, which caused death in up to 70% of the treated animals, B.4205 had very little effect on the sensitivity of nude mice bearing human melanoma xenografts to the acute toxic effects of BCNU under the conditions used. (FIGS. 9–13)
13) BeG sensitised the GM-CFCs in the three human bone marrow samples tested to the toxic effects of temozolomide but in two of these samples, little or no sensitization was produced by B.4205. This assay may therefore be used to predict the possible myelosuppressive effects of ATase inactivators when used in the clinic in combination with BCNU and related agents. (FIG. 14)

FIGS. 8 to 13 show results of tests in vivo. Good responses in animal models are a prerequisite for trials of potential chemotherapeutic agents in cancer patients and an indicator of potential utility in treating human tumours (see Schabel et al. in *Nitrosoureas: Current Status and New Developments* Eds. Prestakyo et al., Academic Press, New York, 1981 p 9–26; Dolan et al., *Proc. Natl. Acad. Sci. USA*, 87, 5368–5372, 1990).

A preferred group of compounds of Formula 1 are those in which R is a thiophene or furan ring with a substituent in a 1, 3- or 1, 4-relationship with the methylene group attached to the guanine residue. Also preferred are compounds of Formula I in which R is a pyridine ring with a substituent in the 1, 3-relationship with the methylene group attached to the guanine residue. In either case the substituent is preferably selected from halo (particularly bromo, chloro or fluoro), cyano, SOR"" (wherein R"" is alkyl, particularly $C_1$–$C_5$ alkyl), or azido.

A number of further ATase inactivators in accordance with the invention have been synthesized and the particulars are listed in Tables 8a and 8b $O^6$-Substituted guanines in Table 8 were made by the standard preparation as described above, usually with 3 mmol alcohol $RCH_2OH$ per mmol quaternary salt.

The alcohols were made as described above by sodium borohydride reduction of the corresponding aldehydes, with two exceptions. For 4-bromothenyl alcohol[28] required for B.4280 the aldehyde is commercially available.

5-Chlorothiophen-2-aldehyde[29] and 5-methylthiothiophen-2-aldehyde[30] were prepared by Vilsmeier reaction on 2-chlorothiophen and 2-methylthiothiophen respectively. Sodium borohydride reduction of the methylthioaldehyde followed by sodium periodate oxidation[31] of the resulting methylthioalcohol yielded the methylsulphinylalcohol required for B.4294. Reduction of the chloroaldehyde gave 5-chlorothenyl alcohol[32] for B.4281.

Several other aldehydes were obtained by halogenation of the appropriate thiophen aldehyde or furfural. Thus, direct bromination gave 5-bromofurfural[33] and thence the alcohol[34] for B.4336. Halogen in presence of aluminium chloride on thiophen-2-aldehyde yielded 4-chlorothiophen-2-aldehyde[35] (for the alcohol for B.4298), on thiophen-3-aldehyde yielded 2-bromothiophen-4-aldehyde[36] (and eventually B.4313), and on 5-chlorothiophen-2-aldehyde yielded 4,5-dichlorothiophen-2-aldehyde[37] (for the alcohol[38] for B.4318).

Cyanoaldehydes were obtained from copper cyanide and the corresponding bromoaldehydes in refluxing dimethylformamide. 5-Cyanothiophen-2-aldehyde[39] and its 4-cyano isomer[40] then gave the 5-cyano and 4-cyano[41] alcohols, for B.4283 and B.4317 respectively.

Finally, 4-methoxythenyl alcohol[42] (for B.4300) was prepared as described from 2,3-dibromosuccinic acid and methyl thioglycollate, and ultimate reduction of the methyl ester (not aldehyde in this case) by lithium aluminium hydride and 2-chloro-4-picolyl alcohol[43] (for B.4321) by sodium borohydride reduction[44] of the corresponding acid chloride, made in turn from reaction[45] of phosphorus oxychloride/pentachloride on isonicotinic acid N-oxide.

By way of specific example, the preparation of $\underline{O}^6$-(4-bromothenyl)guanine (B.4280) will now be described.

Preparation of $\underline{O}^6$-(4-bromothenyl)guanine

A solution of 4-bromothenyl alcohol[28][4.63 g, 24 mmol; $R_f$ 0.38 in TLC(PhMe-MeOH, 4:1)] in DMSO (4 ml) was treated cautiously with sodium hydride (60% in oil; 0.64 g, 16 mmol). After 1 hour's stirring, 2-amino-N,N,N-trimethyl-1H-purin-6-aminium chloride (1.839, 8 mmol) was added. After 1 hour's further stirring, acetic acid (1.3 ml) followed by ether (240 ml) was added and the solid filtered off after 1–2 h. Removal of solvents and excess of alcohol (b.p. 85–90° C./0.4 mm) from the filtrate yielded a negligible second fraction (17 mg). The main crop was triturated with water (10 ml), affording substantially pure product (1.89 g, 73%) with $R_f$ 0.22 in TLC (PhMe-MeOH, 4:1). It was recrystallized by dissolving in hot methanol (100 ml) and then concentrating. Analytical data are given in Tables 8a and 8b.

The effect of the compounds of Table 8 in inactivating pure recombinant ATase in vitro is shown in Table 9. In the tests on these compounds, whose results are shown in Table 9 and in FIGS. 15 to 24, the Methods used were as described above. The following items are also to be noted:

Standard ATase Assay

ATase substrate DNA was prepared by incubation of purified calf thymes DNA with N-[$^3$H]-methyl-N-nitrosuourea (18.7 Ci/mmole, Amersham International). Cell or tissue extracts (see 4.4) were incubated with [$^3$H]-methylated-DNA substrate (100 μl containing 6.7 μg of DNA and 100 fmol of $O^6$-[$^3$H]methylguanine) at 37° C. for 60 mins. Following acid hydrolysis of the DNA as previously described[21] the [$^3$H]-methylated protein was recovered and quantitated by liquid scintillation counting.

Drug Treatment

Mice were treated with the inactivator as a suspension in corn oil by intraperitoneal injection (i.p.) or by oral gavage (p.o.) 60 mins prior to temozolomide (100 mg/kg in 20% DMSO in phosphate-buffered saline) which was always given by intraperitoneal injection: this schedule was repeated on days 1 to 5 inclusive. Controls received vehicle alone, inactivator alone or temozolomide alone.

Animals

The mice in the tests shown in FIGS. 17 and 18 were BALB-C derived athymic male mice (nu/nu athymic) from the in-house breeding colony at the Paterson Institute for Cancer Research as described above (Animal Services Unit-ASU Mice).

The mice in the tests shown in FIGS. 19–24 were Swiss mouse derived athymic male mice (u/nu athymic) from ZENECA Pharmaceuticals, Mereside, Alderley Park, Macclesfield, Cheshire SK10 4T6, England.

The mice in the tests shown in FIG. 25 werie $DBA_2$ mice from the in-house breeding colony of the Paterson Institute for Cancer Research (Animal Services Unit), originally from the Jackson Laboratory in 1970.

TABLE 8a

| Test No. | $O^6$-Substituent | Yield % (based on solvate) | Solvent for recrystn. | M.p. (decomp.) (° C.) | Formula | | Analysis C | H | N |
|---|---|---|---|---|---|---|---|---|---|
| B.4280 | 4-bromothenyl | 73 | MeOH | 204–205 | $C_{10}H_8BrN_5OS$ | Found | 36.7 | 2.45 | 21.46 |
| | | | | | | Req. | 36.82 | 2.47 | 21.47 |
| B.4281 | 5-chlorothenyl[a] | 39 | MeCN | 155–158 | $C_{10}H_8ClN_5OS$ | Found | 41.81 | 2.86 | 24.10 |
| | | | | | | Req. | 42.63 | 2.86 | 24.86 |
| B.4283 | 5-cyanothenyl[b] | 10 | MeOH | 200 upwards | $C_{11}H_8N_6OS.0.5\ H_2O$ | Found | 47.01 | 2.94 | 28.24 |
| | | | | | | Req. | 46.97 | 3.23 | 29.88 |
| B.4294 | 5-methylsulph-inylthenyl | 32 | MeOH | 200 upwards | $C_{11}H_{11}N_5O_2S_2$ | Found | 42.58 | 3.62 | 22.27 |
| | | | | | | Req | 42.71 | 3.58 | 22.64 |
| B.4298 | 4-chlorothenyl | 34 | MeCN | 194–198 | $C_{10}H_8ClN_5OS$ | Found | 42.70 | 2.94 | 24.84 |
| | | | | | | Req | 42.63 | 2.86 | 24.86 |
| B.4300 | 4-methoxythenyl | 44 | MeOH | 189–190 | $C_{11}H_{11}N_5O_2S$ | Found | 47.73 | 4.15 | 25.05 |
| | | | | | | Req | 47.64 | 4.00 | 25.26 |
| B.4313 | 5-bromo-3-thienylmethyl | 7.6 | MeCN | 190 upwards | $C_{10}H_8BrN_5OS$ | Found | 37.02 | 2.43 | 20.95 |
| | | | | | | Req | 36.82 | 2.47 | 21.47 |
| B.4317 | 4-cyanothenyl | 32 | MeOH | 213–216 | $C_{11}H_8N_6OS$ | Found | 48.50 | 2.84 | 30.66 |
| | | | | | | Req | 48.52 | 2.96 | 30.87 |
| B.4318 | 4,5-dichlorothenyl | 38 | MeOH | 210 upwards | $C_{10}H_7Cl_2N_5OS.1H_2O$ | Found | 35.94 | 2.67 | 20.96 |
| | | | | | | Req | 35.94 | 2.71 | 20.96 |

TABLE 8a-continued

| Test No. | $O^6$-Substituent | Yield % (based on solvate) | Solvent for recrystn. | M.p. (decomp.) (° C.) | Formula | Analysis | | C | H | N |
|---|---|---|---|---|---|---|---|---|---|---|
| B.4321 | 2-chloro-4-picolyl | 10 | MeOH | 234 upwards | $C_{11}H_9ClN_6O$ | Found | | 47.15 | 3.52 | 29.32 |
| | | | | | | Req | | 47.75 | 3.29 | 30.37 |
| B.4336 | 5-bromofurfuryl | 39 | MeOH | 180 upwards | $C_{10}H_8BrN_5O_2 \cdot 0.25\ H_2O$ | Found | | 38.22 | 2.71 | 21.93 |
| | | | | | | Req | | 38.18 | 2.72 | 22.26 |

[a]5.6 mmol alcohol per mmol quaternary salt used in synthesis.
[b]Dimethylformamide reaction solvent.

TABLE 8b

| Test No. | $O^6$-Substituent | $\lambda_{max}$ (nm)(MeOH) | $\delta_H$ [ppm from TMS; $(CD_3)_2SO$], J (Hz) |
|---|---|---|---|
| B.4280 | 4-bromothenyl | 238, 284 ($RCH_2OH$: 233). | 5.65(s), 6.40(s), 7.37(d), 7.71(d), 7.85(s), 12.49(s). |
| B.4281 | 5-chlorothenyl | 247, 284 ($RCH_2OH$: 245). | 5.59(s), 6.40(s), 7.06(d), 7.22(d), 7.87(s), 12.47(bs). |
| B.4283 | 5-cyanothenyl | 247, 272 | 5.73(s), 6.46(s), 7.49(d), 7.87(s), 7.92(d), 12.54(bs). |
| B.4294 | 5-methylsulphinylthenyl | 243, 284(sh) [$RCH_2OH$: 240, 274(sh)]. | 2.93(s), 5.73(s), 6.41(s), 7.40(d), 7.52(d), 7.88(s), 12.52(bs). |
| B.4298 | 4-chlorothenyl | 238, 284 ($RCH_2OH$: 240). | 5.64(s), 6.42(s), 7.34(d), 7.62(d), 7.86(s), 12.51(s). |
| B.4300 | 4-methoxythenyl | 245(sh), 282 ($RCH_2OH$: 258). | 3.75(s), 5.57(s), 6.37(s), 6.60(d), 7.01(d), 7.85(s), 12.48(s). |
| B.4313 | 5-bromo-3-thienylmethyl | 240, 284 ($RCH_2OH$: 236). | 5.42(s), 6.38(s), 7.40(d), 7.72(d), 7.85(s), 12.47(s). |
| B.4317 | 4-cyanothenyl | 244, 284 ($RCH_2OH$: 244). | 5.68(s), 6.44(s), 7.74(d), 7.86(s), 8.60(d), 12.50(s). |
| B.4318 | 4,5-dichlorothenyl | 243, 285 ($RCH_2OH$: 243). | 5.58(s), 6.45(s), 7.41(s), 7.87(s), 12.52(s). |
| B.4321 | 2-chloro-4-picolyl | 241, 272(sh), 285 [$RCH_2OH$: 262, 268(sh)]. | 5.58(s), 6.36(s), 7.51(bs), 7.61(bs), 7.91(bs), 8.44(bs), 12.56(bs). |
| B.4336 | 5-bromofurfuryl | 220, 284 ($RCH_2OH$: 223) | 5.42(s), 6.39(s), 6.64(d), 6.78(d), 7.85(s), 12.49(s). |

TABLE 9

| INACTIVATOR | M. Wt | $I_{50}$ ($\mu$m) |
|---|---|---|
| B.4280 $O^6$-(4-bromothenyl)guanine | 326 | 0.0034 |
| B.4281 $O^6$-(5-chlorothenyl)guanine | 281.7 | 0.004 |
| B.4283 $O^6$-(5-cyanothenyl)guanine | 281 | 0.005 |
| B.4294 $O^6$-(5-methylsulphinylthenyl)guanine | 309 | 0.03 |
| B.4298 $O^6$-(4-chlorothenyl)guanine | 281.7 | 0.008 |
| B.4300 $O^6$-(4-methoxythenyl)guanine | 277 | 0.0165 |
| B.4313 $O^6$-(5-bromo-3-thienylmethyl)guanine | 326 | 0.0065 |
| B.4317 $O^6$-(4-cyanothenyl)guanine | 272 | 0.0028 |
| B.4318 $O^6$-(4,5-dichlorothenyl)guanine | 334 | 0.015 |
| B.4321 $O^6$-(2-chloro-4-picolyl)guanine | 276.7 | 0.04 |
| B.4336 $O^6$-(5-bromofurfuryl)guanine | 314.6 | 0.02 |

Among the inactivators of Table 9, a preferred compound is B.4280 which is $\underline{O}^6$-(4-bromothenyl)guanine having the formula:

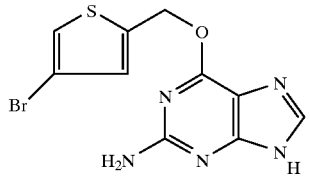

B.4280, which has its bromo substituent in a 1, 3-relationship with the methylene group attached to the guanine residue, was more efficient in inactivating ATase in vitro than its 5-bromo analogue B.4269, in which the bromo substituent is in a 1, 4-relationship with the methylene group. Both B.4280 and B.4269 were more efficient than the unsubstituted thenyl derivative B.4205.

Another preferred compound is B.4317 which is $\underline{O}^6$-(4-cyanothenyl)guanine. B.4317 is a more efficient inactivator in vitro than its 5-cyano analogue B.4283 or the unsubstituted thenyl derivative B.4205.

Typical ATase inactivation profiles for BeG and B.4205 and B.4280 are shown in FIG. 15.

The inactivation of ATase resulted in the sensitization of Raji cells to the growth inhibitory effects of temozolomide (FIG. 16). B.4280 was much more effective than either B.4205 or BeG in this respect. There was no evidence of toxicity of the inactivators themselves.

ATase in human melanoma xenografts was inactivated by BeG, B.4205 and B.4280 (FIG. 17) with some indication that the rates of recovery of ATase activity were different between the agents. B.4280 was the most effective in vivo inactivator at the doses examined.

B.4205 was able to inactivate ATase in most mouse tissues examined but there was less inactivation in brain than other tissues (FIG. 18). B.4280 was also able to inactivate ATase in most tissues as shown in Table 10. Thus, activity in brain, testis and bone marrow was near to control levels by 24 hours whereas lung and spleen activity had not completely recovered by 48 hours. Tumour activity was very low at 24 hours but had recovered completely by 48 hours. Differential recovery rates might be an important factor in the toxicity of ATase inactivators when used in combination with CNU or temozolomide.

Combinations of B.4205 or B.4280 and temozolomide given over three days were more effective in ATase inactivation in tumour xenografts than either agent alone (FIG. 19). Decreasing the dose of B.4205 had no major effect on the ability of the agent to inactivate ATase, 10 mg/kg being ag ettentive as 60 mg/kg. B.4280 was more effective than B.4205 at equivalent doses. As before (FIG. 17) there was some indicating that ATase recovery was more efficient in the liver than in the tumour xenograft (FIG. 20).

B.4205 (FIG. 21A) and B.4280 (FIG. 22A) were effective in sensitizing human melanonid xenografts to the growth inhibitory effects of temozolomide. A comparison of the two sets at data indicates that B.4280 was about twice as effective as B.4205 in this respect. At equi-effective doses for tumour growth inhibition. 9.4280 seems to be less toxic than B.4205 (FIGS. 21B and 22B).

In experiments using $DBA_2$ mice in combination with BCNU, B.4280 was considerably less acutely toxic than B.4205 or BeG as shown in Table 11. In an in vitro assay with four different patient samples, BeG sensitized human bone marrow granulocyte macrophage colony forming cells (GM-CFC) to the cytotoxic effects of temozolomide [see also ref 27] whereas sensitization by B.4205 only occurred in one patient (FIG. 23). Oral administration of H.4280 was shown to be almost as effective as i.p. administration in sensitizing human melanoma xenografts to the growth inhibitory effects of temozolomide (FIG. 24A). Furthermore the oral combination appeared to be marginally less toxic than the i.p. route (FIG. 24B).

At a dose of 20 mg/kg of inactivator in combination with temozolomide (TZ) in $DBA_2$ mice, B.4205 and B.4280 were shown to be less acutely toxic than BeG, with B.4280 being less acutely toxic than B.4205 (FIG. 25).

TABLE 10

ATASE ACTIVITY IN VARIOUS TISSUES OF NU/NU MICE AFTER TREATMENT WITH 10 mg/kg (IP) B.4280 MEAN ACTIVITY (fm/mg)

| Tissue | 24 h | 48 h | Control* |
|---|---|---|---|
| Tumour | 36 ± 7.79 | 140 ± 43.87 | 125 |
| Liver | 89.7 ± 10.14 | 100.7 ± 8.73 | 110** |
| Lung | 15.3 ± 2.05 | 24 ± 2.83 | 43 |
| Kidney | 24.3 ± 4.03 | 28.7 ± 4.11 | 33 |
| Spleen | 41 ± 5.35 | 68.3 ± 9.53 | 81 |
| Brain | 13.7 ± 2.05 | 16.3 ± 1.25 | 14 |

TABLE 10-continued

ATASE ACTIVITY IN VARIOUS TISSUES OF NU/NU MICE AFTER TREATMENT WITH 10 mg/kg (IP) B.4280 MEAN ACTIVITY (fm/mg)

| Tissue | 24 h | 48 h | Control* |
|---|---|---|---|
| Testis | 45 ± 7.48 | 44 ± 1.41 | 45 |
| Bone Marrow (pooled) | 42 | 61 | 30 |

*control values taken from a separate experiment
**mean of 2 control liver values
Table 9.
Effect of B.4280 on ATase activity in several tissues of nude mice. Animals were given a single dose of B.4280 (10 mg/kg i.p.) and sacrificed 24 or 48 hours later.

TABLE 11

TOXICITY OF INACTIVATORS IN COMBINATION WITH BCNU IN $DBA_2$ MICE

| INACTIVATOR (60 mg/kg) | % SURVIVAL AFTER 14 DAYS | | |
|---|---|---|---|
| | 20 mg/kg BCNU | 16 mg/kg BCNU | 12 mg/kg BCNU |
| $O^6$-benzylguanine | 33 (2/6) | 0 (0/6)* | 50 (3/6)** |
| B.4205 | 0 (0/6) | 50 (3/6)* | 100 (6/6)** |
| B.4280 | 93 (14/15) | 100 (15/15) | 100 (15/15) |

*15 mg/kg BCNU
**10 mg/kg BCNU
All agents were given as a single i.p. dose
Table 10
Effect of ATase inactivators on the acute toxicity of bis-chloroethylnitrosourea (BCNU) in $DBA_2$ mice.

References
1. W. N. Haworth and W. G. M. Jones, *J.Chem.Soc.*, 1944, 667
2. T. Reichstein, Helv.Chim.Acta, 9, 1926, 1066.
3. V. Bocchi, G. Casnati, A. Dossena and R. Marchelli, *Synthesis*, 1979, 961.
4. P. A. Finan, *J.Chem.Soc.*, 1963, 3917; J. A. Moore and J. E. Kelly, J. Polym.Sci., Polym.Chem.Ed., 22, 1984, 863.
5. J. Kiermayer, *Chemiker-Zeitung*, 19, 1895, 1004.
6. A. Carotti, F. Campagna and R. Ballini, *Synthesis*, 1979, 56.
7. A. J. Floyd, R. G. Kinsman, Y. Roshan-Ali and D. W. Brown, *Tetrahedron*, 39, 1983, 3881
8. V. T. Suu, N. P. Buu-Hoi and N. D. Xuong, *Bull.Soc.Chim.France*, 1962, 1875.
9. T. Reichstein and L. Reichstein *Helv.Chim.Acta*, 13, 1930, 1275.
10. H. Takeshita, H. Mametsuka and H. Motomura. *J. Heterocycl.Chim.*, 23, 1986, 1211.
11. F. J. Wolf and J. Weijlard, *Org.Synth.,Coll.Vol.*4, 1963, 124.
12. A. M. van Leusen, B. E. Hoogenboom and H. Siderius, *Tetrahedron Lett.*, 1972, 2369.
13. A. Maquestiau, R. Flammang and F. B. Abdelouahab, *Heterocycles*, 29, 1989, 103.
14. S. Fallab, *Helv.Chim.Acta*, 35, 1952, 215
15. A. S. Kende, K. Kawamura and R. J. DeVita, *J.Amer.Chem.Soc.*, 112, 1990, 4070.
16. S. Trofimenko, *J.Org.Chem.*, 28, 1963, 3243.
17. I. Sawhney and J. R. H. Wilson (Shell Internationale), EP. 395,174, 1989 (*Chem.Abs.*, 114, 143410s).
18. F. Dallacker, P. Fechter and V. Mues, *Z. Naturforsch.*, 34b, 1979, 1729.
19. P. Fournari, *Bull.Soc.Chim.France*, 1963, 488.
20. L. Grehn, *Chem.Scr.*, 16, 1980, 72.

21. Morten, J. E. N. & Margison, G. P. (1988) Carcinogenesis 9, 45–49
22. Scudiero, D. A., Shoemaker R. J., Paull K. D., Monks A., Tierney S., Nofziger T. H., Currens M. J., Seniff D, & Boyd M. R. (1988), Cancer Research 48, 4827–4833
23. Fan, C.-Y., Potter, P. M., Rafferty, J. A., Watson, A. J., Cawkwell, L., Searle, P. F., O'Connor, P. J. and Margison, G. P. (1991) Nucleic Acids Res. 18, 5723–5727
24. Carmichael J., DeGraff W. G., Gazdar A. F., Minna J. D., Mitchell J. B. (1987). Evaluation of a tetrazolium based semiautomated colorimetric assay: assessment of chemosensitivity testing. Cancer Res. 47 : 936–942.
25. Wilkinson, M. C., Potter, P. M., Cawkwell, L., Georgiadis, P., Patel, D., Swann, P. F. and Margison, G. P. (1989) Nucleic Acids Res. 17, 8475–8484.
26. Wilkinson, M. C., Cooper, D. P., Southan, C., Potter, P. M. & Margison, G. P. (1990) Nucleic Acids Res., 18, 13–16.
27. Fairbairn L., Watson.A. J., Rafferty J., Elder R. H., and Margison G. P., (1995) Exp. Haematol. 23, 112.
28. M. D. Dowle, R. Hayes, D. B. Judd and C. N. Williams, *Synthesis*, 1983, 73.
29. E. Campaigne and W. L. Archer, *J.Amer. Chem. Soc.*, 75, 1953, 989.
30. J. Cymerman-Craig and J. W. Loder, *J. Chem. Soc.*, 1954, 237.
31. C. R. Johnson and J. E. Keiser, *Org. Synth. Coll. Vol. 5*. 1973, 791.
32. T. L. Cairns and B. C. McKusick, *J. Org. Chem.*, 15, 1950, 790.
33. Z. N. Nazarova, *Zhur. Obshch. Khim.*, 24, 1954, 575 (*Chem. Abs.*, 49, 6214, 10261; 53, 15047).
34. W. J. Chute, W. M. Orchard and G. F. Wright, *J. Org. Chem.*, 6,1941, 157.
35. J. Iriarte, E. Martinez and J. M. Muchowski, *J. Heterocycl. Chem.*, 13, 1976, 393.
36. P. Fournari, R. Guilard and M. Person, *Bull. Soc. Chim. France*, 1967, 4115.
37. S. Conde, R. Madronero, M. P. Fernandez-Tome and J. del Rio, *J. Med. Chem.*, 21, 1978, 978.
38. E. Profft and D. Gerber, *J. Prakt. Chem.*, 16, 1962, 18.
39. Farbwerke Hoechst A. -G., *Brit. Pat.*1127,064 1968 (*Chem. Abs.*, 70, 47284f).
40. P. Dubus, B. Decroix, J. Morel and P. Pastour, *Bull. Soc. Chim. France*, 1976, 628.
41. P. J. Newcombe and R. K. Norris, *Austral. J. Chem.*, 34, 1981, 1879.
42. P. R. Huddleston, J. M. Barker, B. Stickland, M. L. Wood and L. H. M. Guindi, *J. Chem. Research*, 1988, (S) 240, (M) 1871.
43. M. Hamana and M. Yamazaki, *J. Pharm. Soc. Japan*, 81, 1961, 574 (*Chem. Abs.* 55, 24743).
44. F. E. Ziegler and J. G. Sweeny, *J. Org. Chem.*, 34, 1969, 3545.
45. C. R. de Wet and P. A. de Villiers, *Tydskr. Natuurwet.*, 14, 1974, 70 (*Chem. Abs.* 84, 30822w).

We claim:

1. $O^6$-alkylguanine derivatives of formula I:

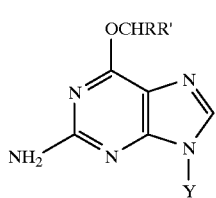

(I)

wherein
Y is H, ribosyl, deoxyribosyl, or

wherein X is O or S, R" and R'" are alkyl or substituted alkyl,
R' is H, or alkyl or hydroxyalkyl
R is
(i) a cyclic group having at least one 5- or 6-membered heterocyclic ring or a substituted 5- or 6-membered heterocyclic ring, optionally with a carbocyclic, substituted carbocyclic, heterocyclic or substituted heterocyclic ring fused thereto, the or each heterocyclic or substituted heterocyclic ring having at least one hetero atom chosen from O, N, or S, or
ii) naphthyl or a substituted naphthyl and pharmaceutically acceptable salts thereof, provided that R is not a cyclic group having a heterocyclic ring with more than one S atom in the ring.

2. A compound according to claim 1 wherein R is:
(a) a 5- or 6-membered heterocyclic ring,
(b) a benzo derivative thereof,
(c) a substituted 5- or 6-membered ring, or
(d) a substituted benzo derivative of a 5- or 6-membered heterocyclic ring the $O^6$-alkylguanine moiety being attached to R at either the heterocyclic, the substituted heterocyclic ring, the benzene ring, or the substituted benzene ring.

3. A compound according to claim 1 wherein R is a 5 membered heterocyclic ring, having one S atom therein, or a substituted 5 membered heterocyclic ring, having one S atom therein.

4. A compound according to claim 1 wherein R is a member selected from the group consisting of a thiophene ring, a substituted thiophene ring, a furan ring and a substituted furan ring.

5. A compound according to claim 1 wherein R is a cyclic group having at least one 5- or 6-membered heterocyclic ring, optionally with a carbocyclic or heterocyclic ring fused thereto, wherein the heterocyclic or carbocyclic ring is substituted by halo, haloalkyl, cyano, $SO_nR""$ where R"" is alkyl and n=0, 1 or 2, or —$COOR^5$ wherein $R^5$ is alkyl.

6. A compound according to claim 1 wherein R is a member selected from the group consisting of a thiophene ring, a bromo-substituted thiophene ring, a cyano-substituted thiophene ring, a furan ring, a bromo-substituted furan ring, and a cyano-substituted furan ring.

7. A compound according to claim 1 which is $O^6$-thenylguanine.

8. A compound according to claim 1 which is $O^6$-(5-bromothenyl)guanine.

9. A compound according to claim 1 which is a member selected from the group consisting of O⁶-(3-thienylmethyl)-guanine,
O⁶-piperonylguanine,
O⁶-furfurylguanine,
O⁶-(3-furylmethyl)-guanine,
O⁶-(2-benzo[b]thienylmethyl)-guanine,
O⁶-(2-benzofuranylmethyl)-guanine,
O⁶-(5-thiazolymethyl)-guanine,
O⁶-(5-methoxycarbonylfurfuryl)-guanine,
O⁶-(5-methoxycarbonylfurfuryl)-guanine,
O⁶-(3-cyanofurfuryl)-guanine,
O⁶-(2-benzo[b]thienylmethyl)-guanosine,
O⁶-(4-picolyl)-guanine, and
O⁶-(2-naphthylmethyl)-guanine.

10. A pharmaceutical composition comprising a compound according to claim 1 and a pharmaceutically acceptable excipient.

11. A pharmaceutical composition according to claim 10 further comprising an alkylating agent.

12. A composition according to claim 11 wherein the alkylating agent is a member selected from the group consisting of 1,3 bis (2-chloroethyl)-1-nitrosourea (BNCU) and temozolomide.

13. A method for depleting O⁶-alkylguanine-DNA alkyltransferase activity in a host comprising:
administering to the host an effective O⁶-alkylguanine-DNA alkyltransferase activity depleting amount of a composition according to claim 10.

14. A method according to claim 13 comprising:
administering to the host an effective O⁶-alkylguanine-DNA alkyltransferase activity depleting amount of a composition comprising O⁶-thenylguanine and a pharmaceutically acceptable excipient.

15. A method for treating tumour cells in a host comprising:
administering to the host a composition comprising an inactivator compound according to claim 1 in an amount effective to deplete O⁶-alkylguanine-DNA alkyltransferase activity sufficiently to enhance the effectiveness of a chemotherapeutic alkylating agent; and
administering to the host a composition comprising an alkylating agent in an amount which is effective in combination with the said inactivator compound for treating said tumour cells.

16. A method according to claim 15 wherein the said inactivator compound is O⁶-thenylguanine.

17. A process for preparing a compound of the formula I

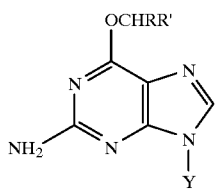

(I)

wherein Y, R' and R are as defined in claim 1 which comprises reacting sodium hydride with a solution of RR'CHOH in an organic solvent, adding 2-amino-N, N,N-trimethyl-1H-purin-6-aminium chloride or 2 amino-6-chloropurine riboside, treatment with weak acid and ether, and extracting the desired product.

18. A compound according to claim 1 wherein R' is H and R is selected from thiophene and furan rings with a chloro-, bromo- or cyano-substituent in a 1,3- or 1,4-relationship with the methylene group attached to the guanine residue.

19. O⁶-(4-bromothenyl)guanine.

20. A compound according to claim 2 which is a member selected from the group consisting of
O⁶-(5-chlorothenyl)guanine,
O⁶-(5-cyanothenyl)guanine,
O⁶-(5-methylsulphinylthenyl)guanine,
O⁶-(4-chlorothenyl)guanine,
O⁶-(4-methoxythenyl)guanine,
O⁶-(5-bromo-3-thienylmethyl)guanine,
O⁶-(4-cyanothenyl)guanine,
O⁶-(4,5-dichlorothenyl)guanine,
O⁶-(2-chloro-4-picolyl)guanine and
O⁶-(5-bromofurfuryl)guanine.

21. A pharmaceutical composition comprising O⁶-(4-bromothenyl)guanine and a pharmaceutically acceptable excipient.

22. The pharmaceutical composition according to claim 21 in a form which is suitable for oral administration.

23. A pharmaceutical composition according to claim 21 further comprising an alkylating agent.

24. A pharmaceutical composition according to claim 23 wherein the alkylating agent is a member selected from the group consisting of 1,3 bis (2-chloroethyl)-1-nitrosourea (BNCU) and temozolomide.

25. A method for depleting O⁶-alkylguanine-DNA alkyltransferase activity in a host comprising:
administering to the host an effective O⁶-alkylguanine-DNA alkyltransferase activity depleting amount of a composition comprising O⁶-(4-bromothenyl)guanine and a pharmaceutically acceptable excipient.

26. A method for treating tumour cells in a host comprising:
administering to the host a composition comprising O⁶-(4bromothenyl)guanine in an amount effective to deplete O⁶-alkylguanine-DNA alkyltransferase activity sufficiently to enhance the effectiveness of a chemotherapeutic alkylating agent; and
administering to the host a composition comprising an alkylating agent in an amount which is effective in combination with said composition comprising O⁶-(4bromothenyl)guanine for treating said tumour cells.

27. A compound according to claim 1 wherein R' is H and R is a thiophene ring or a halo-substituted thiophene ring.

28. A compound according to claim 27 wherein R' is H and R is a bromo-substituted thiophene ring.

29. A method for treating tumour cells in a host comprising:
administering to the host a composition comprising an inactivator compound according to claim 27 in an amount effective to deplete O⁶-alkylguanine-DNA alkyltransferase activity sufficiently to enhance the effectiveness of a chemotherapeutic alkylating agent; and
administering to the host a composition comprising an alkylating agent in an amount which is effective in combination with the said inactivator compound.

30. A method according to claim 29 wherein R' is H and R is a bromo-substituted thiophene ring.

31. A compound according to claim 1 wherein R' is H and R is a thiophene or furan ring with a substituent in a 1, 3 or 1, 4 relationship with the methylene group attached to the guanine residue, the substituent being a member which is selected from the group consisting of halo, cyano, azido, methoxy and SOR"", wherein R"" is alkyl.

32. O⁶-alkylguanine derivatives of the formula I:

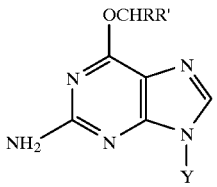

(I)

wherein

Y is H, ribosyl, deoxyribosyl, or

wherein X is O or S, R" and R''' are alkyl or substituted alkyl,

R' is H, or alkyl or hydroxyalkyl;

R is
- (i) a cyclic group having at least one 5- or 6-membered heterocyclic ring or a substituted 5- or 6-membered heterocyclic ring, optionally with a carbocyclic, substituted carbocyclic, heterocyclic or substituted heterocyclic ring fused thereto, the or each heterocyclic or substituted heterocyclic ring having at least one hetero atom chosen from O, N, or S, or
- ii) naphthyl or a substituted naphthyl and pharmaceutically acceptable salts thereof, provided that R is not a cyclic group having a heterocyclic ring with more than one S atom in the ring; and provided that when Y or R is substituted as aforesaid the compound has the ability to deplete O⁶alkylguanine-DNA alkyltransferase activity.

33. O⁶-alkylguanine derivatives of the formula I:

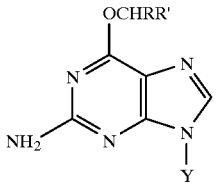

(I)

wherein

Y is H, ribosyl, deoxyribosyl, or

wherein X is O or S, R" and R''' are alkyl or suibstituted alkyl, having substitution by one or more of hydroxy, alkoxy, amino, alkylamino, amido or ureido;

R' is H or alkyl or hydroxyalkyl;

R is
- (i) a cyclic group having at least one 5- or 6-membered heterocyclic ring or a substituted 5- or 6-membered heterocyclic ring, optionally with a carbocyclic, substituted carbocyclic, heterocyclic or substituted heterocyclic ring fused thereto, the or each heterocyclic or substituted heterocyclic ring having at least one hetero atom chosen from O, N, or S, having substitution in the substituted heterocyclic ring(s) or substituted carbocyclic ring(s) by one or more of alkyl, alkenyl, alkynyl, halo, haloalkyl, nitro, cyano, hydroxyalkyl, azido, methoxy, $SO_nR''''$ where R"" is alkyl and n=0, 1 or 2, or a carboxyl or ester group of the formula —COOR⁵ wherein R⁵ is H or alkyl; or
- (ii) naphthyl or a naphthyl having substitution by one or more of alkyl, alkenyl, alkynyl, halo, haloalkyl, nitro, cyano, hydroxyalkyl, azido, methoxy, $SO_nR''''$ where R"" is alkyl and n=0, 1 or 2, or a carboxyl or ester group of tho formula —COOR⁵ wherein R⁵ is H or alkyl;

and pharmaceutically acceptable salts thereof, provided that R is not a cyclic group having a heterocyclic ring with more than one S atom in the ring.

34. A compound according to claim 33 wherein

Y is H, ribosyl, deoxyribosyl, or

wherein X is O or S, R" and R''' are alkyl or substituted alkyl, having substitution by one or more of hydroxy, amino, alkylamino, amido or ureido;

R' is H or alkyl or hydroxyalkyl;

R is
- (i) a cyclic group having at least one 5- or 6-membered heterocyclic ring or a substituted 5- or 6-membered heterocyclic ring, optionally with a carbocyclic, substituted carbocyclic heterocyclic or substituted heterocyclic ring fused thereto, the or each heterocyclic or substituted heterocyclic ring having at least one hetero atom chosen from O, N, or S, having substitution in the substituted heterocyclic ring(s) or substituted carbocyclic ring(s) by one or more of alkyl, alkenyl, alkynyl, halo, haloalkyl, nitro, cyano, hydroxyalkyl, $SO_nR''''$ where R"" is alkyl and n=0, 1 or 2; or
- (ii) naphthyl or a naphthyl having substitution by one or more of alkyl, alkenyl, alkynyl, halo, haloalkyl, nitro, cyano, hydroxyalkyl, $SO_nR''''$ where R"" is alkyl and n=0, 1 or 2;

and pharmaceutically acceptable salts thereof;

provided that R is not a cyclic group having a heterocyclic ring with more than one S atom in the ring.

35. A compound according to claim 33 wherein Y and R' are as defined in claim 33 and R is
- (i) a cyclic group having at least one 5- or 6-membered heterocyclic ring or a substituted 5- or 6-membered heterocyclic ring, optionally with a carbocyclic, substituted carbocyclic, heterocyclic or substituted heterocyclic ring fused thereto, the or each heterocyclic or substituted heterocyclic ring having at least one hetero atom chosen from O, N, or S, having substitution in the substituted heterocyclic ring(s) or substituted carbocyclic ring(s) by one or more of alkyl, alkenyl, alkynyl, halo, haloalkyl, nitro, cyano, hydroxyalkyl, $SO_nR''''$ where $R''''$ is alkyl and n=0, 1 or 2, or a carboxyl or ester group of the formula —$COOR^5$ wherein $R^5$ is H or alkyl; or (ii) naphthyl or a naphthyl having substitution by one or more of alkyl, alkenyl, alkynyl, halo, haloalkyl, nitro, cyano, hydroxyalkyl, $SO_nR''''$ where $R''''$ is alkyl and n=0, 1 or 2, or a carboxyl or ester group of the formula —$COOR^5$ wherein $R^5$ is H or alkyl;

and pharmaceutically acceptable salts thereof;

provided that R is not a cyclic group having a heterocyclic ring with more than one S atom in the ring.

* * * * *

UNITED STATES PATENT AND TRADEMARK OFFICE

CERTIFICATE OF CORRECTION

PATENT NO. : 6,043,228

DATED : March 28, 2000

INVENTOR(S) : McMurry, et al.

It is certified that an error appears in the above-identified patent and that said Letters Patent is hereby corrected as shown below:

IN THE TITLE PAGE:

In Section [75], please change the following information as follows:

Change "...; Robert Stanley McBlhinney;..." to --"...; Robert Stanley McElhinney;..."--

Signed and Sealed this

Third Day of April, 2001

*Attest:*

NICHOLAS P. GODICI

*Attesting Officer*   *Acting Director of the United States Patent and Trademark Office*